(12) United States Patent
Rawal et al.

(10) Patent No.: US 9,686,988 B2
(45) Date of Patent: Jun. 27, 2017

(54) PESTICIDAL COMPOUNDS BASED ON ARYLTHIOSULFONAMIDE DERIVATIVES

(71) Applicant: Syngenta Participations AG, Basel (CH)

(72) Inventors: Girish Rawal, Goa (IN); Rupesh Patre, Goa (IN); Guillaume Berthon, Stein (CH); Jerome Yves Cassayre, Stein (CH); Myriem El Qacemi, Stein (CH)

(73) Assignee: Syngenta Participations AG, Basel (CH)

( * ) Notice: Subject to any disclaimer, the term of this patent is extended or adjusted under 35 U.S.C. 154(b) by 103 days.

(21) Appl. No.: 14/442,699

(22) PCT Filed: Nov. 21, 2013

(86) PCT No.: PCT/EP2013/074398
§ 371 (c)(1),
(2) Date: May 13, 2015

(87) PCT Pub. No.: WO2014/079937
PCT Pub. Date: May 30, 2014

(65) Prior Publication Data
US 2016/0286808 A1    Oct. 6, 2016

(30) Foreign Application Priority Data

Nov. 21, 2012 (EP) .................................... 12193615
Nov. 21, 2012 (IN) ........................... 3577/DEL/2012

(51) Int. Cl.
| | | |
|---|---|---|
| A01N 43/80 | (2006.01) | |
| A01N 43/10 | (2006.01) | |
| C07D 261/04 | (2006.01) | |
| C07D 333/18 | (2006.01) | |
| C07D 413/12 | (2006.01) | |
| C07D 333/38 | (2006.01) | |

(52) U.S. Cl.
CPC ............. *A01N 43/80* (2013.01); *A01N 43/10* (2013.01); *C07D 261/04* (2013.01); *C07D 333/18* (2013.01); *C07D 333/38* (2013.01); *C07D 413/12* (2013.01)

(58) Field of Classification Search
None
See application file for complete search history.

(56) References Cited

U.S. PATENT DOCUMENTS

| | | |
|---|---|---|
| 3,862,184 A | 1/1975 | Goralski et al. |
| 3,895,010 A | 7/1975 | Goralski et al. |
| 3,925,468 A | 12/1975 | Goralski et al. |
| 3,946,007 A | 3/1976 | Goralski et al. |
| 3,987,095 A | 10/1976 | Goralski et al. |

FOREIGN PATENT DOCUMENTS

| | | |
|---|---|---|
| EP | 2172448 A1 | 4/2010 |
| JP | 2007/106756 A | 4/2007 |
| WO | 2012/156400 A1 | 11/2012 |

OTHER PUBLICATIONS

Christian T. Goralski et al: "1-(Arylthio)Methanesulfonamides", Journal of Chemical & Egineering Data, vol. 21, No. 2, Apr. 1, 1976, p. 237-239.
International Search Report for PCT/EP2013/074398 dated Jan. 2, 2014.

*Primary Examiner* — Michael Barker
(74) *Attorney, Agent, or Firm* — R. Kody Jones

(57) ABSTRACT

The present invention provides compounds of formula (I) wherein $R^1$, $R^2$, $R^3$, $R^4$, n, $A^1$, $A^2$, $A^3$, $Y^1$, $Y^2$, and $Y^3$ are as defined in the claims. The invention also relates to processes and intermediates for preparing these compounds, to insecticidal, acaricidal, nematicidal and molluscicidal compositions comprising these compounds and to methods of using these compounds to control insect, acarine, nematode and mollusc pests.

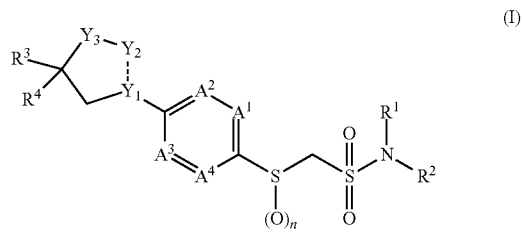

(I)

21 Claims, No Drawings

PESTICIDAL COMPOUNDS BASED ON ARYLTHIOSULFONAMIDE DERIVATIVES

RELATED APPLICATION INFORMATION

This application is a 371 of International Application No. PCT/EP2013/074398, filed 21 Nov. 2013, which claims priority to EP Patent Application No. 121936157.7 filed 21 Nov. 2012; and Indian Patent Application No. 3577/DEL/2012 filed 21 Nov. 2012, the contents of which are incorporated herein by reference herein.

The present invention relates to certain arylthiosulfonamides and derivatives thereof, to processes and intermediates for preparing these compounds, to insecticidal, acaricidal, nematicidal and molluscicidal compositions comprising these compounds and to methods of using these compounds to control insect, acarine, nematode and mollusc pests.

Certain compounds with insecticidal properties are disclosed, for example, in JP2007106756. However there is a continuing need to find new biologically active compounds as well as new biologically active compounds displaying superior properties for use as agrochemical active ingredients, for example greater biological activity, different spectrum of activity, increased safety profile, or increased biodegradability.

It has now surprisingly been found that certain orthosubstituted arylthiosulfonamides have highly potent insecticidal properties.

Accordingly in a first aspect the invention provides compounds of formula I

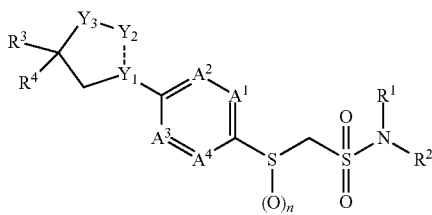

wherein
$A^1$ is C—$R^{5b}$;
$A^2$, $A^3$ and $A^4$ are independently of one another C—H, C—$R^{5a}$ or nitrogen;
$Y_1$—$Y_2$—$Y_3$ is —C=N—O—, —C=N—S—, —C=N—CH$_2$—, —C=CH—O— or —N—CH$_2$—CH$_2$—, —C=CH—S—;
n is 0, 1 or 2;
$R^1$ is hydrogen, $C_1$-$C_8$alkyl, $C_1$-$C_8$alkoxy, $C_1$-$C_8$alkylcarbonyl or $C_1$-$C_8$alkoxycarbonyl;
$R^2$ is hydrogen, $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, aryl-$C_1$-$C_4$alkylene or aryl-$C_1$-$C_4$alkylene wherein the aryl moiety is substituted by one to five $R^8$, heterocyclyl-$C_1$-$C_4$alkylene or heterocyclyl-$C_1$-$C_1$-$C_4$alkylene wherein the heterocyclyl moiety is substituted by one to five $R^8$, aryl or aryl substituted by one to five $R^8$, heterocyclyl or heterocyclyl substituted by one to five $R^8$; or $R^1$ and $R^2$ together with the nitrogen atom to which they are bound form a 4- to 7-membered cycle containing carbon atoms as ring members and optionally containing one oxygen atom or one sulfur atom optionally oxidised as a ring member and wherein the cycle is optionally substituted by 1 to 5 groups independently selected from halogen, $C_1$-$C_4$alkyl and $C_1$-$C_4$alkoxy;
$R^3$ is $C_1$-$C_8$haloalkyl;
$R^4$ is aryl or aryl substituted by one to five $R^9$, or heteroaryl or heteroaryl substituted by one to five $R^9$;
each $R^{5a}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-;
$R^{5b}$ is halogen, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl or $C_3$-$C_{10}$cycloalkyl substituted by one to five $R^7$,
or $R^{5a}$ and $R^{5b}$ on adjacent carbon atoms together form a —CH=CH—CH=CH— bridge or a —N=CH—CH=CH— bridge;
each $R^6$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;
each $R^7$ is independently halogen, cyano, $C_1$-$C_8$alkyl or $C_1$-$C_8$haloalkyl;
each $R^8$ and $R^9$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{10}$ or heterocyclyl or heterocyclyl substituted by one to five $R^{10}$;
each $R^{10}$ is independently halogen, cyano, nitro, $C_1$-$C_4$alkyl, $C_1$-$C_4$haloalkyl, $C_1$-$C_4$alkoxy or $C_1$-$C_4$haloalkoxy;
or a salt or N-oxide thereof.

In a further aspect the present invention relates to compounds of formula I

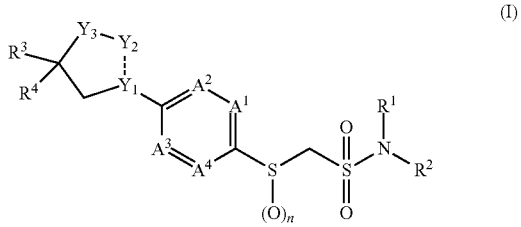

wherein
$A^1$ is C—$R^{5b}$;
$A^2$, $A^3$ and $A^4$ are independently of one another C—H, C—$R^{5a}$ or nitrogen;
$Y_1$—$Y_2$—$Y_3$ is —C=N—O—, —C=N—S—, —C=N—CH$_2$—, —C=CH—O— or —N—CH$_2$—CH$_2$—;
n is 0, 1 or 2;
$R^1$ is hydrogen, $C_1$-$C_8$alkyl, $C_1$-$C_8$alkoxy, $C_1$-$C_8$alkylcarbonyl or $C_1$-$C_8$alkoxycarbonyl;

$R^2$ is hydrogen, $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, aryl-$C_1$-$C_4$alkylene or aryl-$C_1$-$C_4$alkylene wherein the aryl moiety is substituted by one to five $R^8$, heterocyclyl-$C_1$-$C_4$alkylene or heterocyclyl-$C_1$-$C_4$alkylene wherein the heterocyclyl moiety is substituted by one to five $R^8$, aryl or aryl substituted by one to five $R^8$, heterocyclyl or heterocyclyl substituted by one to five $R^8$;

or $R^1$ and $R^2$ together with the nitrogen atom to which they are bound form a 4- to 7-membered cycle containing carbon atoms as ring members and optionally containing one oxygen atom or one sulfur atom optionally oxidised as a ring member and wherein the cycle is optionally substituted by 1 to 5 groups independently selected from halogen, $C_1$-$C_4$alkyl and $C_1$-$C_4$alkoxy;

$R^3$ is $C_1$-$C_8$haloalkyl;

$R^4$ is aryl or aryl substituted by one to five $R^9$, or heteroaryl or heteroaryl substituted by one to five $R^9$;

each $R^{5a}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-;

$R^{5b}$ is halogen, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl or $C_3$-$C_{10}$cycloalkyl substituted by one to five $R^7$, or $R^{5a}$ and $R^{5b}$ on adjacent carbon atoms together form a —CH=CH—CH=CH— bridge or a —N=CH—CH=CH— bridge;

each $R^6$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;

each $R^7$ is independently halogen, cyano, $C_1$-$C_8$alkyl or $C_1$-$C_8$haloalkyl;

each $R^8$ and $R^9$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{10}$ or heterocyclyl or heterocyclyl substituted by one to five $R^{10}$;

each $R^{10}$ is independently halogen, cyano, nitro, $C_1$-$C_4$alkyl, $C_1$-$C_4$haloalkyl, $C_1$-$C_4$alkoxy or $C_1$-$C_4$haloalkoxy;

or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, in the —CR³R⁴— group and may exist as enantiomers (or as pairs of diastereoisomers) or as mixtures of such. Further, where any group is SO, the compounds of the invention are sulfoxides, which can also exist in two enantiomeric forms.

Alkyl groups (either alone or as part of a larger group, such as alkoxy, alkylthio, alkylsulfinyl, alkylsulfonyl, alkylcarbonyl or alkoxycarbonyl) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, —CH₂—, —CH₂—CH₂—, —CH(CH₃)—, —CH₂—CH₂—CH₂—, —CH(CH₃)—CH₂— or —CH(CH₂CH₃)—. The alkylene groups are preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups. For the avoidance of doubt, alkenyl groups contain one or more carbon-carbon double bonds, each of which may be located at any point on the chain.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups. For the avoidance of doubt, alkynyl groups contain one or more carbon-carbon triple bonds, each of which may be located at any point on the chain.

Halogen is fluorine, chlorine, bromine or iodine.

Haloalkyl groups (either alone or as part of a larger group, such as haloalkoxy, haloalkylthio, haloalkylsulfinyl or haloalkylsulfonyl) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. 1.2.4 triazoyl), furanyl, thiophenyl, oxazolyl, isoxazolyl, oxadiazolyl, thiazolyl, isothiazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkylene) are defined to include heteroaryl groups and in addition their unsaturated or partially unsaturated analogues. Examples of monocyclic groups include isoxazolyl, thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Preferred values of $A^1$, $A^2$, $A^3$, $A^4$, n, $R^1$, $R^2$, $R^3$, $R^4$, $Y^1$, $Y^2$, $Y^3$, $R^{5a}$, $R^{5b}$, $R^6$, $R^7$, $R^8$, $R^9$, $R^{10}$ and $R^{12}$ are, in any combination, as set out below.

Preferably no more than two of $A^2$, $A^3$ and $A^4$ are nitrogen.

Preferably $A^2$ is C—H, C—$R^{5a}$ or N, more preferably $A^2$ is C—H or C—$R^{5a}$, most preferably $A^2$ is C—H.

Preferably $A^3$ is C—H or N, most preferably $A^3$ is C—H.

Preferably $A^4$ is C—H or N, most preferably $A^4$ is C—H.

In one group of compounds $A^2$, $A^3$ and $A^4$ are C—H or N, wherein no more than two of $A^2$, $A^3$ and $A^4$ are N and wherein $A^3$ and $A^4$ are not both N. Preferably $A^2$ is C—H and $A^3$ and $A^4$ are C—H or one of $A^3$ and $A^4$ is N. More preferably $A^2$, $A^3$ and $A^4$ are C—H.

Preferably $R^1$ is hydrogen, methyl, ethyl, methylcarbonyl or methoxycarbonyl, more preferably hydrogen, methyl or ethyl, even more preferably hydrogen or methyl, most preferably hydrogen.

Preferably, $R^2$ is $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, aryl-$C_1$-$C_4$alkylene or aryl-$C_1$-$C_4$alkylene wherein the aryl moiety is substituted by one to five $R^8$, heterocyclyl-$C_1$-$C_4$alkylene or heterocyclyl-$C_1$-$C_4$alkylene wherein the heterocyclyl moiety is substituted by one to five $R^8$, aryl or aryl substituted by one to five $R^8$, heterocyclyl or heterocyclyl substituted by one to five $R^8$, wherein each aryl group is a phenyl group and each heterocyclyl group is independently selected from pyridyl, pyridazinyl, pyrimidinyl, pyrazinyl, pyrrolyl, pyrazolyl, imidazolyl, triazolyl, tetrahydrothiophenyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxo-thietanyl, dioxo-thietanyl, pyrrolidinyl, tetrahydrofuranyl, [1,3]dioxolanyl, piperidinyl, piperazinyl, [1,4]dioxanyl, morpholinyl, 2,3-dihydro-benzofuranyl, benzo[1,3]dioxolanyl, and 2,3-dihydro-benzo-[1,4]dioxinyl.

More preferably $R^2$ is $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, phenyl-$C_1$-$C_4$alkylene or phenyl-$C_1$-$C_4$alkylene wherein the phenyl moiety is substituted by one to five $R^8$, phenyl or phenyl substituted by one to five $R^8$, pyridyl-$C_1$-$C_4$alkylene or pyridyl-$C_1$-$C_4$alkylene wherein the pyridyl moiety is substituted by one to four $R^8$, pyridyl or pyridyl substituted by one to four $R^8$, oxetanyl-$C_1$-$C_4$alkylene or oxetanyl-$C_1$-$C_4$alkylene wherein the oxetanyl moiety is substituted by one to five $R^8$, oxetanyl or oxetanyl substituted by one to five $R^8$, thietanyl-$C_1$-$C_4$alkylene or thietanyl-$C_1$-$C_4$alkylene wherein the thietanyl moiety is substituted by one to five $R^8$, thietanyl or thietanyl substituted by one to five $R^8$, oxo-thietanyl-$C_1$-$C_4$alkylene or oxo-thietanyl-$C_1$-$C_4$alkylene wherein the oxo-thietanyl moiety is substituted by one to five $R^8$, oxo-thietanyl or oxo-thietanyl substituted by one to five $R^8$, dioxo-thietanyl-$C_1$-$C_4$alkylene or dioxo-thietanyl-$C_1$-$C_4$alkylene wherein the dioxo-thietanyl moiety is substituted by one to five $R^8$, dioxo-thietanyl or dioxo-thietanyl substituted by one to five $R^8$, furanyl-$C_1$-$C_4$alkylene or furanyl-$C_1$-$C_4$alkylene wherein the furanyl moiety is substituted by one to four $R^8$, tetrahydrofuranyl or tetrahydrofuranyl substituted by one to five $R^8$.

More preferably $R^2$ is $C_1$-$C_4$alkyl or $C_1$-$C_4$alkyl substituted by one to five groups independently selected from halogen, cyano, $C_1$-$C_4$alkoxy and $C_1$-$C_4$alkylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_6$cycloalkyl or $C_3$-$C_6$cycloalkyl substituted by one to five groups independently selected from halogen, methyl and halomethyl, phenyl-$C_1$-$C_2$alkylene or phenyl-$C_1$-$C_2$alkylene wherein the phenyl moiety is optionally substituted by one to three substituents independently selected from halogen, cyano, $C_1$-$C_4$alkyl, $C_1$-$C_4$haloalkyl, $C_1$-$C_4$alkoxy and $C_1$-$C_4$haloalkoxy, pyridyl-$C_1$-$C_2$alkylene or pyridyl-$C_1$-$C_2$alkylene wherein the pyridyl moiety is optionally substituted by one to three substituents independently selected from halogen, cyano, $C_1$-$C_4$alkyl, $C_1$-$C_4$haloalkyl, $C_1$-$C_4$alkoxy and $C_1$-$C_4$haloalkoxy, thietanyl, oxo-thietanyl, dioxo-thietanyl, oxetanyl, tetrahydrofuranyl, thietanyl-methyl, oxo-thietanyl-methyl, dioxo-thietanyl-methyl, oxetanyl-methyl.

Even more preferably $R^2$ is $C_1$-$C_4$alkyl or $C_1$-$C_4$alkyl substituted by one to five groups independently selected from halogen, cyano, methoxy and methylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_4$cycloalkyl or $C_3$-$C_4$cycloalkyl substituted by one to five groups independently selected from halogen, methyl and halomethyl, pyridylmethyl or pyridylmethyl wherein the pyridyl moiety is substituted with one to four groups selected from halogen, cyano, methyl, halomethyl, methoxy and halomethoxy.

Most preferably $R^2$ is methyl, ethyl, propyl, butyl, fluoroethyl, fluoropropyl, fluorobutyl, difluoroethyl, difluoropropyl, difluorobutyl, trifluoroethyl, trifluoropropyl, trifluorobutyl, cyclopropyl, cyclobutyl, allyl, propargyl or pyridylmethyl.

In one embodiment $R^1$ and $R^2$ together with the nitrogen atom to which they are bound form a 4- to 7-membered cycle containing carbon atoms as ring members and optionally containing one oxygen atom or one sulfur atom optionally oxidized (e.g. —S(O)— or —S($O_2$)—) as a ring member and wherein the cycle is optionally substituted by 1 to 5 groups independently selected from halogen $C_1$-$C_4$alkyl and $C_1$-$C_4$alkoxy. Preferably $R^1$ and $R^2$ together with the nitrogen atom to which they are bound form a 4- to 7-membered cycle containing carbon atoms as ring members and optionally containing one oxygen atom as a ring member. Preferably $R^1$ and $R^2$ together with the nitrogen atom to which they are bound form a ring fragment selected from —$(CH_2)_3$—, —$(CH_2)_4$—, —$(CH_2)_5$—, and —$(CH_2)_2O(CH_2)_2$—.

Preferably $R^3$ is chlorodifluoromethyl or trifluoromethyl, most preferably trifluoromethyl.

Preferably $R^4$ is aryl or aryl substituted by one to three $R^9$, more preferably $R^4$ is phenyl or phenyl substituted by one to three $R^9$, even more preferably $R^4$ is phenyl substituted by one to three $R^9$, more preferably $R^4$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl, more preferably 3,5-dichlorophenyl-, 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl) phenyl-, 3,5-dibromophenyl-, or 3,4-dichlorophenyl-.In one group of componds $R^4$ is group A1

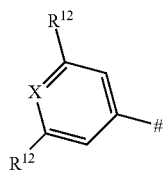

(A1)

wherein X is C—$R^{12}$ or nitrogen (preferably C—$R^{12}$) and each $R^{12}$ is independently hydrogen, halogen or trihalomethyl, wherein at least two $R^{12}$ are not hydrogen.

Preferably each $R^{5a}$ is independently halogen, cyano, nitro, $C_1$-$C_8$alkyl, $C_3$-$C_8$cycloalkyl, $C_1$-$C_8$haloalkyl, $C_2$-$C_8$alkenyl, more preferably halogen, cyano, nitro, $C_1$-$C_8$alkyl, $C_2$-$C_8$alkenyl, $C_3$-$C_8$cycloalkyl, $C_1$-$C_8$haloalkyl, even more preferably bromo, chloro, fluoro, cyano, nitro, methyl, ethyl, trifluoromethyl, cyclopropyl, vinyl, most preferably bromo, chloro, fluoro, cyclopropyl, trifluoromethyl, vinyl, methyl or ethyl.

Preferably $R^{5b}$ is halogen, $C_1$-$C_8$alkyl, $C_3$-$C_8$cycloalkyl, $C_1$-$C_8$haloalkyl, $C_2$-$C_8$alkenyl, more preferably bromo, chloro, fluoro, cyano, nitro, methyl, ethyl, trifluoromethyl, cyclopropyl, vinyl, even more preferably bromo, chloro, fluoro, cyclopropyl, trifluoromethyl, vinyl or methyl, most preferably halogen or methyl. In one group of compounds $R^{5b}$ is bromo. In one group of compounds $R^{5b}$ is chloro. In one group of compounds $R^{5b}$ is methyl. In one group of compounds $R^{5b}$ is chloro, bromo or methyl. In one group of compounds $R^{5b}$ is chloro or bromo.

Preferably each $R^6$ is independently halogen, nitro, cyano, $C_1$-$C_4$alkyl, $C_1$-$C_4$haloalkyl, $C_1$-$C_4$alkoxy, $C_1$-$C_4$haloalkoxy, $C_1$-$C_4$alkylthio, more preferably bromo, chloro, fluoro, cyano, nitro, methyl, ethyl, trifluoromethyl, methoxy, difluoromethoxy, trifluoromethoxy, methylthio, even more preferably chloro, fluoro, cyano, nitro, methyl, ethyl, trifluoromethyl, methoxy, trifluoromethoxy or methylthio, most preferably bromo, chloro, fluoro, or trifluoromethyl.

Preferably each $R^7$ is independently chloro, fluoro, cyano, methyl or halomethyl, most preferably fluoro or methyl.

Preferably each $R^8$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{10}$ or heterocyclyl or heterocyclyl substituted by one to five $R^{10}$, more preferably each $R^8$ is independently halogen, cyano, nitro, $C_1$-$C_8$alkyl, $C_1$-$C_8$haloalkyl, $C_1$-$C_8$alkoxy, $C_1$-$C_8$haloalkoxy or $C_1$-$C_8$alkylthio, more preferably halogen, cyano, $C_1$-$C_4$alkyl, $C_1$-$C_4$alkoxy, $C_1$-$C_4$haloalkyl or $C_1$-$C_4$haloalkoxy, even more preferably halogen, cyano, methyl, methoxy, halomethyl or halomethoxy, even more preferably halogen, cyano, methoxy, methyl, or trifluoromethyl, most preferably halogen, cyano, methoxy, or trifluoromethyl.

Preferably each $R^9$ is independently halogen, $C_1$-$C_8$alkyl, $C_1$-$C_8$haloalkyl, $C_1$-$C_8$alkoxy, $C_1$-$C_8$haloalkoxy, $C_1$-$C_8$alkylthio or $C_1$-$C_8$haloalkylthio, more preferably bromo, chloro, fluoro, trifluoromethyl, methoxy or methylthio, most preferably trifluoromethyl, bromo or chloro.

Preferably each $R^{10}$ is independently bromo, chloro, fluoro, cyano, nitro, methyl, ethyl, trifluoromethyl, methoxy, difluoromethoxy or trifluoromethoxy, more preferably bromo, chloro, fluoro, nitro or methyl, most preferably chloro, fluoro or methyl.

In one group of compounds n is 0. In another group of compounds n is 1. In another group of compounds n is 2.

In one group of compounds $R^ya$ and $R^{5b}$ on adjacent carbon atoms together form a —CH=CH—CH=CH— bridge or a —N=CH—CH=CH— bridge. In another group of compounds $R^{5a}$ and $R^{5b}$ on adjacent carbon atoms do not together form a —CH=CH—CH=CH— bridge or a —N=CH—CH=CH— bridge.

In one group of compounds the invention relates to compounds of formula IAa wherein $Y_1$—$Y_2$—$Y_3$ is —C=N—O—, and wherein the definitions of the other substituents and preferred definitions thereof are as defined above. A particularly preferred embodiment within this group of compounds is represented by compounds of formula IAb

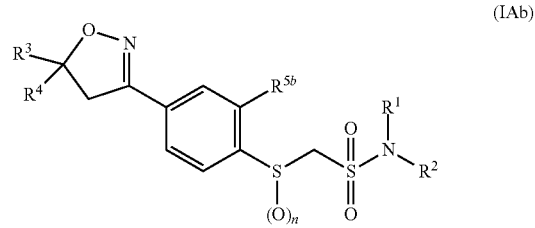

(IAb)

wherein $R^3$, $R^4$, $R^{5b}$, n, $R^1$ and $R^2$, including preferred definitions thereof, are as defined for compounds of formula I. Preferably $R^{5b}$ is bromo, chloro, fluoro, or methyl. In one group of compounds of formula IAb $R^{5b}$ is bromo or chloro.

In one group of compounds the invention relates to compounds of formula IBa wherein $Y_1$—$Y_2$—$Y_3$ is —C=N—CH$_2$—, and wherein the definitions of the other substituents and preferred definitions thereof are as defined above. A particularly preferred embodiment within this group of compounds is represented by compounds of formula IBb

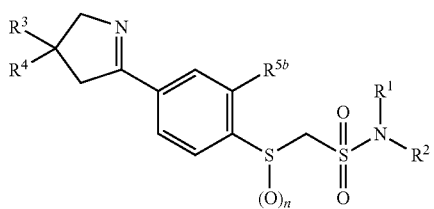

(IBb)

wherein $R^3$, $R^4$, $R^{5b}$, n, $R^1$ and $R^2$, including preferred definitions thereof, are as defined for compounds of formula I. Preferably $R^{5b}$ is bromo, chloro, fluoro, or methyl. In one group of compounds of formula IBb $R^{5b}$ is bromo or chloro.

In one group of compounds the invention relates to compounds of formula ICa wherein $Y_1$—$Y_2$—$Y_3$ is —C=CH—O—, and wherein the definitions of the other substituents and preferred definitions thereof are as defined above. A particularly preferred embodiment within this group of compounds is represented by compounds of formula ICb

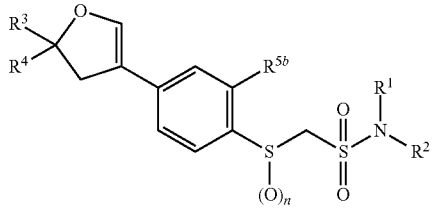

(ICb)

wherein $R^3$, $R^4$, $R^{5b}$, n, $R^1$ and $R^2$, including preferred definitions thereof, are as defined for compounds of formula I. Preferably $R^{5b}$ is bromo, chloro, fluoro, or methyl. In one group of compounds of formula ICb $R^{5b}$ is bromo or chloro.

In one group of compounds the invention relates to compounds of formula IDa wherein $Y_1$—$Y_2$—$Y_3$ is —N—CH$_2$—CH$_2$—, and wherein the definitions of the other substituents and preferred definitions thereof are as defined above. A particularly preferred embodiment within this group of compounds is represented by compounds of formula IDb

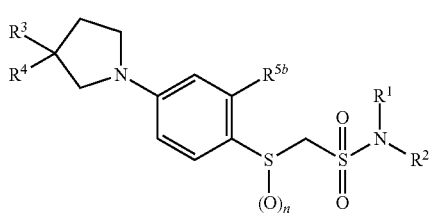

(IDb)

wherein $R^3$, $R^4$, $R^{5b}$, n, $R^1$ and $R^2$, including preferred definitions thereof, are as defined for compounds of formula I. Preferably $R^{5b}$ is bromo, chloro, fluoro, or methyl. In one group of compounds of formula IDb $R^{5b}$ is bromo or chloro.

In one group of compounds the invention relates to compounds of formula IEa wherein $Y_1$—$Y_2$—$Y_3$ is —C=N—S—, and wherein the definitions of the other substituents and preferred definitions thereof are as defined above. A particularly preferred embodiment within this group of compounds is represented by compounds of formula IEb

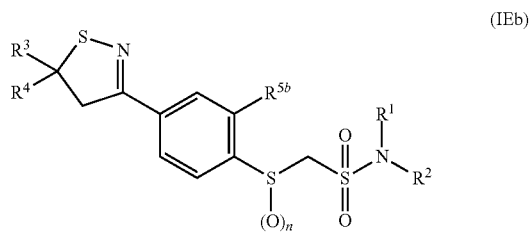

(IEb)

wherein $R^3$, $R^4$, $R^{5b}$, n, $R^1$ and $R^2$, including preferred definitions thereof, are as defined for compounds of formula I. Preferably $R^{5b}$ is bromo, chloro, fluoro, or methyl. In one group of compounds of formula IEb $R^{5b}$ is bromo or chloro.

In one group of compounds the invention relates to compounds of formula IFb

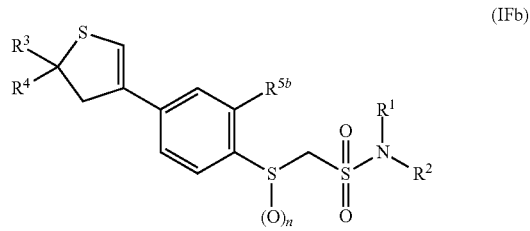

(IFb)

wherein $R^1$, $R^2$, $R^3$, $R^4$, $R^{5b}$ and n, including preferred definitions thereof, are as defined for compounds of formula I. Preferably $R^{5b}$ is bromo, chloro, fluoro, or methyl. In one group of compounds of formula Ia $R^{5b}$ is bromo or chloro.

Compounds in which $Y_1$—$Y_2$—$Y_3$ is —C=N—O— are preferred.

In one group of compounds $A^2$ is C—H and $A^3$ and $A^4$ are C—H or one of $A^3$ and $A^4$ is N; $R^3$ is chlorodifluoromethyl or trifluoromethyl; $R^4$ is 3,5-dibromo-phenyl, 3,5-dichlorophenyl, 3,5-bis-(trifluoromethyl)-phenyl,4-bromo-3,5-dichlorophenyl, 3,5-dichloro-4-fluoro, 3-bromo-5-(trifluoromethyl)phenyl- or 3,4,5-trichloro-phenyl.

In one group of compounds $A^2$ is C—H and $A^3$ and $A^4$ are C—H or one of $A^3$ and $A^4$ is N; $R^1$ is H, $R^3$ is chlorodifluoromethyl or trifluoromethyl; $R^4$ is 3,5-dibromo-phenyl, 3,5-dichloro-phenyl, 3,5-bis-(trifluoromethyl)-phenyl,4-bromo-3,5-dichlorophenyl, 3,5-dichloro-4-fluoro, 3-bromo-5-(trifluoromethyl)phenyl- or 3,4,5-trichloro-phenyl.

In one group of compounds $A^2$, $A^3$ and $A^4$ are C—H; $R^1$ is H, $R^3$ is chlorodifluoromethyl or trifluoromethyl; $R^4$ is 3,5-dibromo-phenyl, 3,5-dichloro-phenyl, 3,5-bis-(trifluoromethyl)-phenyl, 4-bromo-3,5-dichlorophenyl, 3,5-dichloro-4-fluoro, 3-bromo-5-(trifluoromethyl)phenyl- or 3,4,5-trichloro-phenyl.

In one group of compounds $A^2$, $A^3$ and $A^4$ are C—H; $R^1$ is H, $R^3$ is chlorodifluoromethyl or trifluoromethyl; $R^4$ is 3,5-dibromo-phenyl, 3,5-dichloro-phenyl, 3,5-bis-(trifluoromethyl)-phenyl, 4-bromo-3,5-dichlorophenyl, 3,5-dichloro-4-fluoro, 3-bromo-5-(trifluoromethyl)phenyl- or 3,4,5-trichloro-phenyl; $R^{5b}$ is bromo, chloro, fluoro, or methyl.

In one group of compounds $A^1$ is C—$R^{5b}$; $A^2$, $A^3$ and $A^4$ are C—H; $Y_1$—$Y_2$—$Y_3$ is —C=N—O—, —C=N—S—, —C=N—CH$_2$—, —C=CH—S— or —N—CH$_2$—CH$_2$—; $R^1$ is hydrogen; $R^2$ is $C_1$-$C_4$alkyl or $C_1$-$C_4$alkyl substituted by one to five groups independently selected from halogen, cyano, $C_1$-$C_4$alkoxy and $C_1$-$C_4$alkylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_6$cycloalkyl or $C_3$-$C_6$cycloalkyl substituted by one to five groups independently selected from halogen, methyl and halomethyl, phenyl-$C_1$-$C_2$alkylene or phenyl-$C_1$-$C_2$alkylene wherein the phenyl moiety is optionally substituted by one to three substituents independently selected from halogen, cyano, $C_1$-$C_4$alkoxy, $C_1$-$C_4$haloalkyl and $C_1$-$C_4$haloalkoxy, pyridyl-$C_1$-$C_2$alkylene or pyridyl-$C_1$-$C_2$alkylene wherein the pyridyl moiety is optionally substituted by one to three substituents independently selected from halogen, cyano, $C_1$-$C_4$alkoxy, $C_1$-$C_4$haloalkyl and $C_1$-$C_4$haloalkoxy, thietanyl, oxo-thietanyl, dioxo-thietanyl, oxetanyl, tetrahydrofuranyl, thietanyl-methyl, oxo-thietanyl, dioxo-thietanyl-methyl, oxetanyl-methyl; or $R^1$ and $R^2$ together with the nitrogen atom to which they are bound form a 4- to 7-membered cycle containing carbon atoms as ring members and optionally containing one oxygen atom as a ring member; $R^3$ is chlorodifluoromethyl or trifluoromethyl; $R^4$ is group A1

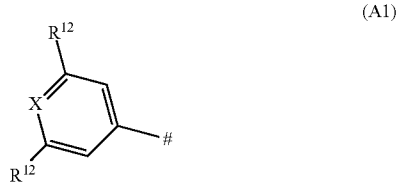

(A1)

wherein X is C—$R^{12}$ or nitrogen (preferably C—$R^{12}$) and each $R^{12}$ is independently hydrogen, halogen or trihalomethyl, wherein at least two $R^{12}$ are not hydrogen; $R^{5b}$ is chloro, bromo or methyl.

In one group of compounds $A^1$ is C—$R^{5b}$; $A^2$, $A^3$ and $A^4$ are C—H; $Y_1$—$Y_2$—$Y_3$ is —C=N—O; $R^1$ is hydrogen; $R^2$ is $C_1$-$C_4$alkyl or $C_1$-$C_4$alkyl substituted by one to five groups independently selected from halogen, cyano, $C_1$-$C_4$alkoxy and $C_1$-$C_4$alkylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_6$cycloalkyl or $C_3$-$C_6$cycloalkyl substituted by one to five groups independently selected from halogen, methyl and halomethyl, phenyl-$C_1$-$C_2$alkylene or phenyl-$C_1$-$C_2$alkylene wherein the phenyl moiety is optionally substituted by one to three substituents independently selected from halogen, cyano, $C_1$-$C_4$alkoxy, $C_1$-$C_4$haloalkyl and $C_1$-$C_4$haloalkoxy, pyridyl-$C_1$-$C_2$alkylene or pyridyl-$C_1$-$C_2$alkylene wherein the pyridyl moiety is optionally substituted by one to three substituents independently selected from halogen, cyano, $C_1$-$C_4$alkyl, $C_1$-$C_4$haloalkyl, $C_1$-$C_4$alkoxy and $C_1$-$C_4$haloalkoxy, thietanyl, oxo-thietanyl, dioxo-thietanyl, oxetanyl, tetrahydrofuranyl, thietanyl-methyl, oxo-thietanyl, dioxo-thietanyl-methyl, oxetanyl-methyl, or or $R^1$ and $R^2$ together with the nitrogen atom to which they are bound form a 4- to 7-membered cycle containing carbon atoms as ring members and optionally containing one oxygen atom as a ring member; $R^3$ is trifluoromethyl; $R^4$ is group A1 wherein X is C—$R^{12}$ or nitrogen (preferably C—$R^{12}$) and each $R^{12}$ is independently hydrogen, halogen or trihalomethyl, wherein at least two $R^{12}$ are not hydrogen; $R^{5b}$ is halogen or methyl.

In one group of compounds A is C—$R^{5b}$; $A^2$, $A^3$ and $A^4$ are C—H; $Y_1$—$Y_2$—$Y_3$ is —C=N—O—, —C=N—S—, —C=N—CH$_2$—, —C=CH—S— or —N—CH$_2$—CH$_2$—; $R^1$ is hydrogen; $R^2$ is $C_1$-$C_4$alkyl or $C_1$-$C_4$alkyl substituted by one to five groups independently selected from halogen, cyano, methoxy and methylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_4$cycloalkyl or $C_3$-$C_4$cycloalkyl substituted by one to five groups independently selected from halogen, methyl and halomethyl, pyridylmethyl or pyridylmethyl wherein the pyridyl moiety is substituted with one to four groups selected from halogen, cyano, methyl, halomethyl, methoxy and halomethoxy; or $R^1$ and $R^2$ together with the nitrogen atom to which they are bound form a 4- to 7-membered cycle containing carbon atoms as ring members and optionally containing one oxygen atom as a ring member; $R^3$ is trifluoromethyl; $R^4$ is group Al, wherein X is C—$R^{12}$ and each $R^{12}$ is independently hydrogen, halogen or trihalomethyl, wherein at least two $R^{12}$ are not hydrogen; $R^{5b}$ is halogen or methyl.

In one group of compounds $A^1$ is C—$R^{5b}$; $A^2$, $A^3$ and $A^4$ are C—H; $Y_1$—$Y_2$—$Y_3$ is —C=N—O—; $R^1$ is hydrogen; $R^2$ is $C_1$-$C_4$alkyl or $C_1$-$C_4$alkyl substituted by one to five groups independently selected from halogen, cyano, methoxy and methylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_4$cycloalkyl or $C_3$-$C_4$cycloalkyl substituted by one to five groups independently selected from halogen, methyl and halomethyl, pyridylmethyl or pyridylmethyl wherein the pyridyl moiety is substituted with one to four groups selected from halogen, cyano, methyl, halomethyl, methoxy and halomethoxy; or $R^1$ and $R^2$ together with the nitrogen atom to which they are bound form a 4- to 7-membered cycle containing carbon atoms as ring members and optionally containing one oxygen atom as a ring member; $R^3$ is trifluoromethyl; $R^4$ is group Al, wherein X is C—$R^{12}$ and each $R^{12}$ is independently hydrogen, halogen or trihalomethyl, wherein at least two $R^{12}$ are not hydrogen; $R^{5b}$ is halogen or methyl.

In one group of compounds $A^1$ is C—$R^{5b}$; $A^2$, $A^3$ and $A^4$ are C—H; $Y_1$—$Y_2$—$Y_3$ is —C=N—O—, —C=N—S—, —C=N—CH$_2$—, —C=CH—S— or —N—CH$_2$—CH$_2$—; $R^1$ is hydrogen; $R^2$ is $C_1$-$C_4$alkyl or $C_1$-$C_4$alkyl substituted by one to five groups independently selected from halogen, cyano, methoxy and methylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_4$cycloalkyl or $C_3$-$C_4$cycloalkyl substituted by one to five groups independently selected from halogen, methyl and halomethyl, pyridylmethyl or pyridylmethyl wherein the pyridyl moiety is substituted with one to four groups selected from halogen, cyano, methyl, halomethyl, methoxy and halomethoxy; $R^3$ is trifluoromethyl; $R^4$ is group Al, wherein X is C—$R^{12}$ and each $R^{12}$ is independently hydrogen, halogen or trihalomethyl, wherein at least two $R^{12}$ are not hydrogen; $R^{5b}$ is halogen or methyl.

In one group of compounds $A_1$ is —$CR^{5b}$; $A^2$, $A^3$ and $A^4$ are C—H; $Y_1$—$Y_2$—$Y_3$ is —C=N—O—; $R^1$ is hydrogen; $R^2$ is is $C_1$-$C_4$alkyl or $C_1$-$C_4$alkyl substituted by one to five groups independently selected from halogen, cyano, methoxy and methylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_4$cycloalkyl or $C_3$-$C_4$cycloalkyl substituted by one to five groups independently selected from halogen, methyl and halomethyl, pyridylmethyl or pyridylmethyl wherein the pyridyl moiety is substituted with one to four groups selected from halogen, cyano, methyl, halomethyl, methoxy and halomethoxy; $R^3$ is trifluoromethyl; $R^4$ is group A1, wherein X is C—$R^{12}$ and each $R^{12}$ is independently hydrogen, halogen or trihalomethyl, wherein at least two $R^{12}$ are not hydrogen; $R^{5b}$ is halogen or methyl.

In one group of compounds $A^1$ is C—$R^{5b}$; $A^2$, $A^3$ and $A^4$ are C—H; $Y_1$—$Y_2$—$Y_3$ is —C=N—O—, —C=N—S—, —C=N—$CH_2$—, —C=CH—S— or —N—$CH_2$—$CH_2$-; $R^1$ is hydrogen; $R^2$ is methyl, ethyl, propyl, butyl, fluoroethyl, fluoropropyl, fluorobutyl, difluoroethyl, difluoropropyl, difluorobutyl, trifluoroethyl, trifluoropropyl, trifluorobutyl, cyclopropyl, cyclobutyl, allyl, propargyl, pyridylmethyl; $R^3$ is trifluoromethyl; $R^4$ is group A1, wherein X is C—$R^{12}$ and each $R^{12}$ is independently hydrogen, halogen or trihalomethyl, wherein at least two $R^{12}$ are not hydrogen; $R^{5b}$ is chloro, bromo or methyl.

In one group of compounds $A^1$ is C—$R^{5b}$; $A^2$, $A^3$ and $A^4$ are C—H; $Y_1$—$Y_2$—$Y_3$ is —C=N—O—; $R^1$ is hydrogen; $R^2$ is methyl, ethyl, propyl, butyl, fluoroethyl, fluoropropyl, fluorobutyl, difluoroethyl, difluoropropyl, difluorobutyl, trifluoroethyl, trifluoropropyl, trifluorobutyl, cyclopropyl, cyclobutyl, allyl, propargyl, pyridylmethyl; $R^3$ is trifluoromethyl; $R^4$ is group A1, wherein X is C—$R^{12}$ and each $R^{12}$ is independently hydrogen, halogen or trihalomethyl, wherein at least two $R^{12}$ are not hydrogen; $R^{5b}$ is chloro, bromo or methyl.

In a preferred embodiment where or $R^1$ and $R^2$ together with the nitrogen atom to which they are bound form a saturated or partially unsaturated 4- to 7-membered cycle containing carbon atoms as ring members and optionally containing one oxygen atom or one sulfur atom optionally oxidised as a ring member and wherein the cycle is optionally substituted by 1 to 5 groups independently selected from halogen, $C_1$-$C_4$alkyl and $C_1$-$C_4$alkoxy;

Certain intermediates are novel and are also included as further aspects of the invention.

In a further aspect the invention provides compounds of formula Int-I

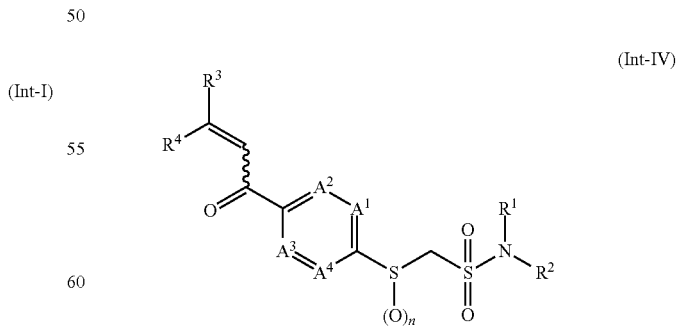

(Int-I)

wherein $Y_1$—$Y_2$—$Y_3$ is —C=N—O—, —C=N—S—, —C=N—$CH_2$—, —C=CH—S—, —C=CH—O—, or —N—$CH_2$—$CH_2$— and $A^1$, $A^2$, $A^3$, $A^4$, $R^3$, $R^4$ and n are as defined for the compound of formula I, and R is OH or halogen, or a salt of N-oxide thereof. Preferred definitions of $A^1$, $A^2$, $A^3$, $A^4$, $R^3$, $R^4$ and n are as defined for compounds of formula I. In one group of compounds of formula Int-I $Y_1$—$Y_2$—$Y_3$ is —C=N—O—. In another group of compounds of formula Int-I $Y_1$—$Y_2$—$Y_3$ is —C=N—$CH_2$. In another group of compounds of formula Int-I $Y_1$—$Y_2$—$Y_3$ is —C=CH—O—. In another group of compounds of formula Int-I $Y_1$—$Y_2$—$Y_3$ is —N—$CH_2$—$CH_2$—. In another group of compounds of formula Int-I $Y_1$—$Y_2$—$Y_3$ is —C=N—S—. In another group of compounds of formula Int-I $Y_1$—$Y_2$—$Y_3$ is —C=CH—S—, In a further aspect the invention provides compounds of formula Int-II

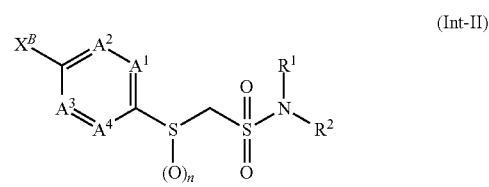

(Int-II)

wherein $A^1$, $A^2$, $A^3$, $A^4$, $R^1$, $R^2$ and n are as defined for the compound of formula I, and $X^B$ is a leaving group, e.g. halogen, such as bromo, or $X^B$ is cyano, formyl or acetyl, or a salt of N-oxide thereof. Preferred definitions of $A^1$, $A^2$, $A^3$, $A^4$, $R^1$, $R^2$ and n are as defined for compounds of formula I.

In a further aspect the invention provides compounds of formula Int-III

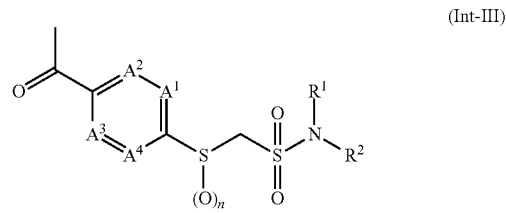

(Int-III)

wherein $A^1$, $A^2$, $A^3$, $A^4$, $R^1$, $R^2$, and n are as defined for the compound of formula I, or a salt of N-oxide thereof. Preferred definitions of $A^1$, $A^2$, $A^3$, $A^4$, $R^1$, $R^2$, and n are as defined for compounds of formula I.

In a further aspect the invention provides compounds of formula Int-IV (Int-IV)

wherein $A^1$, $A^2$, $A^3$, $A^4$, $R^1$, $R^2$, $R^3$, $R^4$ and n are as defined for the compound of formula I, or a salt of N-oxide thereof. Preferred definitions of $A^1$, $A^2$, $A^3$, $A^4$, $R^1$, $R^2$ and n are as defined for compounds of formula I.

A leaving group as referred to herein may be for example a halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. —$N_2^+Cl^-$, —$N_2^+BF_4^-$, —$N_2^+Br^-$, —$N_2^-PF_6^-$), phosphonate esters (e.g. —OP(O)(OR)$_2$, wherein R is methyl or ethyl), preferably bromo, iodo, chloro, trifluoromethylsulfoxy, p-toluenesulfoxy, diazonium chloride.

Tables 1 to 312 below illustrate compounds of the invention.

TABLE P

|  | R5b | n | R2 |
|---|---|---|---|
| 1 | methyl- | 0 | methyl- |
| 2 | chloro- | 0 | methyl- |
| 3 | bromo- | 0 | methyl- |
| 4 | trifluoromethyl- | 0 | methyl- |
| 5 | methyl- | 1 | methyl- |
| 6 | chloro- | 1 | methyl- |
| 7 | bromo- | 1 | methyl- |
| 8 | trifluoromethyl- | 1 | methyl- |
| 9 | methyl- | 2 | methyl- |
| 10 | chloro- | 2 | methyl- |
| 11 | bromo- | 2 | methyl- |
| 12 | trifluoromethyl- | 2 | methyl- |
| 13 | methyl- | 0 | ethyl- |
| 14 | chloro- | 0 | ethyl- |
| 15 | bromo- | 0 | ethyl- |
| 16 | trifluoromethyl- | 0 | ethyl- |
| 17 | methyl- | 1 | ethyl- |
| 18 | chloro- | 1 | ethyl- |
| 19 | bromo- | 1 | ethyl- |
| 20 | trifluoromethyl- | 1 | ethyl- |
| 21 | methyl- | 2 | ethyl- |
| 22 | chloro- | 2 | ethyl- |
| 23 | bromo- | 2 | ethyl- |
| 24 | trifluoromethyl- | 2 | ethyl- |
| 25 | methyl- | 0 | 2-propyl- |
| 26 | chloro- | 0 | 2-propyl- |
| 27 | bromo- | 0 | 2-propyl- |
| 28 | trifluoromethyl- | 0 | 2-propyl- |
| 29 | methyl- | 1 | 2-propyl- |
| 30 | chloro- | 1 | 2-propyl- |
| 31 | bromo- | 1 | 2-propyl- |
| 32 | trifluoromethyl- | 1 | 2-propyl- |
| 33 | methyl- | 2 | 2-propyl- |
| 34 | chloro- | 2 | 2-propyl- |
| 35 | bromo- | 2 | 2-propyl- |
| 36 | trifluoromethyl- | 2 | 2-propyl- |
| 37 | methyl- | 0 | n-propyl- |
| 38 | chloro- | 0 | n-propyl- |
| 39 | bromo- | 0 | n-propyl- |
| 40 | trifluoromethyl- | 0 | n-propyl- |
| 41 | methyl- | 1 | n-propyl- |
| 42 | chloro- | 1 | n-propyl- |
| 43 | bromo- | 1 | n-propyl- |
| 44 | trifluoromethyl- | 1 | n-propyl- |
| 45 | methyl- | 2 | n-propyl- |
| 46 | chloro- | 2 | n-propyl- |
| 47 | bromo- | 2 | n-propyl- |
| 48 | trifluoromethyl- | 2 | n-propyl- |
| 49 | methyl- | 0 | n-butyl- |
| 50 | chloro- | 0 | n-butyl- |
| 51 | bromo- | 0 | n-butyl- |
| 52 | trifluoromethyl- | 0 | n-butyl- |
| 53 | methyl- | 1 | n-butyl- |
| 54 | chloro- | 1 | n-butyl- |
| 55 | bromo- | 1 | n-butyl- |
| 56 | trifluoromethyl- | 1 | n-butyl- |
| 57 | methyl- | 2 | n-butyl- |
| 58 | chloro- | 2 | n-butyl- |
| 59 | bromo- | 2 | n-butyl- |
| 60 | trifluoromethyl- | 2 | n-butyl- |
| 61 | methyl- | 0 | s-butyl- |
| 62 | chloro- | 0 | s-butyl- |
| 63 | bromo- | 0 | s-butyl- |
| 64 | trifluoromethyl- | 0 | s-butyl- |
| 65 | methyl- | 1 | s-butyl- |
| 66 | chloro- | 1 | s-butyl- |
| 67 | bromo- | 1 | s-butyl- |
| 68 | trifluoromethyl- | 1 | s-butyl- |
| 69 | methyl- | 2 | s-butyl- |
| 70 | chloro- | 2 | s-butyl- |
| 71 | bromo- | 2 | s-butyl- |
| 72 | trifluoromethyl- | 2 | s-butyl- |
| 73 | methyl- | 0 | t-butyl |
| 74 | chloro- | 0 | t-butyl |
| 75 | bromo- | 0 | t-butyl |
| 76 | trifluoromethyl- | 0 | t-butyl |
| 77 | methyl- | 1 | t-butyl |
| 78 | chloro- | 1 | t-butyl |
| 79 | bromo- | 1 | t-butyl |
| 80 | trifluoromethyl- | 1 | t-butyl |
| 81 | methyl- | 2 | t-butyl |
| 82 | chloro- | 2 | t-butyl |
| 83 | bromo- | 2 | t-butyl |
| 84 | trifluoromethyl- | 2 | t-butyl |
| 85 | methyl- | 0 | 2,2,2-trifluoro-ethyl- |
| 86 | chloro- | 0 | 2,2,2-trifluoro-ethyl- |
| 87 | bromo- | 0 | 2,2,2-trifluoro-ethyl- |
| 88 | trifluoromethyl- | 0 | 2,2,2-trifluoro-ethyl- |
| 89 | methyl- | 1 | 2,2,2-trifluoro-ethyl- |
| 90 | chloro- | 1 | 2,2,2-trifluoro-ethyl- |
| 91 | bromo- | 1 | 2,2,2-trifluoro-ethyl- |
| 92 | trifluoromethyl- | 1 | 2,2,2-trifluoro-ethyl- |
| 93 | methyl- | 2 | 2,2,2-trifluoro-ethyl- |
| 94 | chloro- | 2 | 2,2,2-trifluoro-ethyl- |
| 95 | bromo- | 2 | 2,2,2-trifluoro-ethyl- |
| 96 | trifluoromethyl- | 2 | 2,2,2-trifluoro-ethyl- |
| 97 | methyl- | 0 | 2,2-difluoro-ethyl- |
| 98 | chloro- | 0 | 2,2-difluoro-ethyl- |
| 99 | bromo- | 0 | 2,2-difluoro-ethyl- |
| 100 | trifluoromethyl- | 0 | 2,2-difluoro-ethyl- |
| 101 | methyl- | 1 | 2,2-difluoro-ethyl- |
| 102 | chloro- | 1 | 2,2-difluoro-ethyl- |
| 103 | bromo- | 1 | 2,2-difluoro-ethyl- |
| 104 | trifluoromethyl- | 1 | 2,2-difluoro-ethyl- |
| 105 | methyl- | 2 | 2,2-difluoro-ethyl- |
| 106 | chloro- | 2 | 2,2-difluoro-ethyl- |
| 107 | bromo- | 2 | 2,2-difluoro-ethyl- |
| 108 | trifluoromethyl- | 2 | 2,2-difluoro-ethyl- |
| 109 | methyl- | 0 | 2-fluoro-ethyl- |
| 110 | chloro- | 0 | 2-fluoro-ethyl- |
| 111 | bromo- | 0 | 2-fluoro-ethyl- |
| 112 | trifluoromethyl- | 0 | 2-fluoro-ethyl- |
| 113 | methyl- | 1 | 2-fluoro-ethyl- |
| 114 | chloro- | 1 | 2-fluoro-ethyl- |
| 115 | bromo- | 1 | 2-fluoro-ethyl- |
| 116 | trifluoromethyl- | 1 | 2-fluoro-ethyl- |
| 117 | methyl- | 2 | 2-fluoro-ethyl- |
| 118 | chloro- | 2 | 2-fluoro-ethyl- |
| 119 | bromo- | 2 | 2-fluoro-ethyl- |
| 120 | trifluoromethyl- | 2 | 2-fluoro-ethyl- |
| 121 | methyl- | 0 | 2-fluoropropyl- |
| 122 | chloro- | 0 | 2-fluoropropyl- |
| 123 | bromo- | 0 | 2-fluoropropyl- |
| 124 | trifluoromethyl- | 0 | 2-fluoropropyl- |
| 125 | methyl- | 1 | 2-fluoropropyl- |
| 126 | chloro- | 1 | 2-fluoropropyl- |
| 127 | bromo- | 1 | 2-fluoropropyl- |
| 128 | trifluoromethyl- | 1 | 2-fluoropropyl- |
| 129 | methyl- | 2 | 2-fluoropropyl- |
| 130 | chloro- | 2 | 2-fluoropropyl- |
| 131 | bromo- | 2 | 2-fluoropropyl- |
| 132 | trifluoromethyl- | 2 | 2-fluoropropyl- |
| 133 | methyl- | 0 | 3,3,3-trifluoro-propyl- |
| 134 | chloro- | 0 | 3,3,3-trifluoro-propyl- |
| 135 | bromo- | 0 | 3,3,3-trifluoro-propyl- |
| 136 | trifluoromethyl- | 0 | 3,3,3-trifluoro-propyl- |
| 137 | methyl- | 1 | 3,3,3-trifluoro-propyl- |
| 138 | chloro- | 1 | 3,3,3-trifluoro-propyl- |
| 139 | bromo- | 1 | 3,3,3-trifluoro-propyl- |
| 140 | trifluoromethyl- | 1 | 3,3,3-trifluoro-propyl- |
| 141 | methyl- | 2 | 3,3,3-trifluoro-propyl- |

TABLE P-continued

| | R5b | n | R2 |
|---|---|---|---|
| 142 | chloro- | 2 | 3,3,3-trifluoro-propyl- |
| 143 | bromo- | 2 | 3,3,3-trifluoro-propyl- |
| 144 | trifluoromethyl- | 2 | 3,3,3-trifluoro-propyl- |
| 145 | methyl- | 0 | 3,3,3-trifluoro-butyl- |
| 146 | chloro- | 0 | 3,3,3-trifluoro-butyl- |
| 147 | bromo- | 0 | 3,3,3-trifluoro-butyl- |
| 148 | trifluoromethyl- | 0 | 3,3,3-trifluoro-butyl- |
| 149 | methyl- | 1 | 3,3,3-trifluoro-butyl- |
| 150 | chloro- | 1 | 3,3,3-trifluoro-butyl- |
| 151 | bromo- | 1 | 3,3,3-trifluoro-butyl- |
| 152 | trifluoromethyl- | 1 | 3,3,3-trifluoro-butyl- |
| 153 | methyl- | 2 | 3,3,3-trifluoro-butyl- |
| 154 | chloro- | 2 | 3,3,3-trifluoro-butyl- |
| 155 | bromo- | 2 | 3,3,3-trifluoro-butyl- |
| 156 | trifluoromethyl- | 2 | 3,3,3-trifluoro-butyl- |
| 157 | methyl- | 0 | 2-cyanoethyl- |
| 158 | chloro- | 0 | 2-cyanoethyl- |
| 159 | bromo- | 0 | 2-cyanoethyl- |
| 160 | trifluoromethyl- | 0 | 2-cyanoethyl- |
| 161 | methyl- | 1 | 2-cyanoethyl- |
| 162 | chloro- | 1 | 2-cyanoethyl- |
| 163 | bromo- | 1 | 2-cyanoethyl- |
| 164 | trifluoromethyl- | 1 | 2-cyanoethyl- |
| 165 | methyl- | 2 | 2-cyanoethyl- |
| 166 | chloro- | 2 | 2-cyanoethyl- |
| 167 | bromo- | 2 | 2-cyanoethyl- |
| 168 | trifluoromethyl- | 2 | 2-cyanoethyl- |
| 169 | methyl- | 0 | cyanomethyl- |
| 170 | chloro- | 0 | cyanomethyl- |
| 171 | bromo- | 0 | cyanomethyl- |
| 172 | trifluoromethyl- | 0 | cyanomethyl- |
| 173 | methyl- | 1 | cyanomethyl- |
| 174 | chloro- | 1 | cyanomethyl- |
| 175 | bromo- | 1 | cyanomethyl- |
| 176 | trifluoromethyl- | 1 | cyanomethyl- |
| 177 | methyl- | 2 | cyanomethyl- |
| 178 | chloro- | 2 | cyanomethyl- |
| 179 | bromo- | 2 | cyanomethyl- |
| 180 | trifluoromethyl- | 2 | cyanomethyl- |
| 181 | methyl- | 0 | 2-cyano-propan-2yl- |
| 182 | chloro- | 0 | 2-cyano-propan-2yl- |
| 183 | bromo- | 0 | 2-cyano-propan-2yl- |
| 184 | trifluoromethyl- | 0 | 2-cyano-propan-2yl- |
| 185 | methyl- | 1 | 2-cyano-propan-2yl- |
| 186 | chloro- | 1 | 2-cyano-propan-2yl- |
| 187 | bromo- | 1 | 2-cyano-propan-2yl- |
| 188 | trifluoromethyl- | 1 | 2-cyano-propan-2yl- |
| 189 | methyl- | 2 | 2-cyano-propan-2yl- |
| 190 | chloro- | 2 | 2-cyano-propan-2yl- |
| 191 | bromo- | 2 | 2-cyano-propan-2yl- |
| 192 | trifluoromethyl- | 2 | 2-cyano-propan-2yl- |
| 193 | methyl- | 0 | 1-methoxy-prop-2-yl- |
| 194 | chloro- | 0 | 1-methoxy-prop-2-yl- |
| 195 | bromo- | 0 | 1-methoxy-prop-2-yl- |
| 196 | trifluoromethyl- | 0 | 1-methoxy-prop-2-yl- |
| 197 | methyl- | 1 | 1-methoxy-prop-2-yl- |
| 198 | chloro- | 1 | 1-methoxy-prop-2-yl- |
| 199 | bromo- | 1 | 1-methoxy-prop-2-yl- |
| 200 | trifluoromethyl- | 1 | 1-methoxy-prop-2-yl- |
| 201 | methyl- | 2 | 1-methoxy-prop-2-yl- |
| 202 | chloro- | 2 | 1-methoxy-prop-2-yl- |
| 203 | bromo- | 2 | 1-methoxy-prop-2-yl- |
| 204 | trifluoromethyl- | 2 | 1-methoxy-prop-2-yl- |
| 205 | methyl- | 0 | 2-methylsulfanyl-ethyl- |
| 206 | chloro- | 0 | 2-methylsulfanyl-ethyl- |
| 207 | bromo- | 0 | 2-methylsulfanyl-ethyl- |
| 208 | trifluoromethyl- | 0 | 2-methylsulfanyl-ethyl- |
| 209 | methyl- | 1 | 2-methylsulfanyl-ethyl- |
| 210 | chloro- | 1 | 2-methylsulfanyl-ethyl- |
| 211 | bromo- | 1 | 2-methylsulfanyl-ethyl- |
| 212 | trifluoromethyl- | 1 | 2-methylsulfanyl-ethyl- |
| 213 | methyl- | 2 | 2-methylsulfanyl-ethyl- |
| 214 | chloro- | 2 | 2-methylsulfanyl-ethyl- |
| 215 | bromo- | 2 | 2-methylsulfanyl-ethyl- |
| 216 | trifluoromethyl- | 2 | 2-methylsulfanyl-ethyl- |
| 217 | methyl- | 0 | 2-methylsulfanyl-prop-3-yl- |
| 218 | chloro- | 0 | 2-methylsulfanyl-prop-3-yl- |
| 219 | bromo- | 0 | 2-methylsulfanyl-prop-3-yl- |
| 220 | trifluoromethyl- | 0 | 2-methylsulfanyl-prop-3-yl- |
| 221 | methyl- | 1 | 2-methylsulfanyl-prop-3-yl- |
| 222 | chloro- | 1 | 2-methylsulfanyl-prop-3-yl- |
| 223 | bromo- | 1 | 2-methylsulfanyl-prop-3-yl- |
| 224 | trifluoromethyl- | 1 | 2-methylsulfanyl-prop-3-yl- |
| 225 | methyl- | 2 | 2-methylsulfanyl-prop-3-yl- |
| 226 | chloro- | 2 | 2-methylsulfanyl-prop-3-yl- |
| 227 | bromo- | 2 | 2-methylsulfanyl-prop-3-yl- |
| 228 | trifluoromethyl- | 2 | 2-methylsulfanyl-prop-3-yl- |
| 229 | methyl- | 0 | allyl- |
| 230 | chloro- | 0 | allyl- |
| 231 | bromo- | 0 | allyl- |
| 232 | trifluoromethyl- | 0 | allyl- |
| 233 | methyl- | 1 | allyl- |
| 234 | chloro- | 1 | allyl- |
| 235 | bromo- | 1 | allyl- |
| 236 | trifluoromethyl- | 1 | allyl- |
| 237 | methyl- | 2 | allyl- |
| 238 | chloro- | 2 | allyl- |
| 239 | bromo- | 2 | allyl- |
| 240 | trifluoromethyl- | 2 | allyl- |
| 241 | methyl- | 0 | 3,3-dichloroallyl- |
| 242 | chloro- | 0 | 3,3-dichloroallyl- |
| 243 | bromo- | 0 | 3,3-dichloroallyl- |
| 244 | trifluoromethyl- | 0 | 3,3-dichloroallyl- |
| 245 | methyl- | 1 | 3,3-dichloroallyl- |
| 246 | chloro- | 1 | 3,3-dichloroallyl- |
| 247 | bromo- | 1 | 3,3-dichloroallyl- |
| 248 | trifluoromethyl- | 1 | 3,3-dichloroallyl- |
| 249 | methyl- | 2 | 3,3-dichloroallyl- |
| 250 | chloro- | 2 | 3,3-dichloroallyl- |
| 251 | bromo- | 2 | 3,3-dichloroallyl- |
| 252 | trifluoromethyl- | 2 | 3,3-dichloroallyl- |
| 253 | methyl- | 0 | 2-butenyl- |
| 254 | chloro- | 0 | 2-butenyl- |
| 255 | bromo- | 0 | 2-butenyl- |
| 256 | trifluoromethyl- | 0 | 2-butenyl- |
| 257 | methyl- | 1 | 2-butenyl- |
| 258 | chloro- | 1 | 2-butenyl- |
| 259 | bromo- | 1 | 2-butenyl- |
| 260 | trifluoromethyl- | 1 | 2-butenyl- |
| 261 | methyl- | 2 | 2-butenyl- |
| 262 | chloro- | 2 | 2-butenyl- |
| 263 | bromo- | 2 | 2-butenyl- |
| 264 | trifluoromethyl- | 2 | 2-butenyl- |
| 265 | methyl- | 0 | 2-chloroallyl- |
| 266 | chloro- | 0 | 2-chloroallyl- |
| 267 | bromo- | 0 | 2-chloroallyl- |
| 268 | trifluoromethyl- | 0 | 2-chloroallyl- |
| 269 | methyl- | 1 | 2-chloroallyl- |
| 270 | chloro- | 1 | 2-chloroallyl- |
| 271 | bromo- | 1 | 2-chloroallyl- |
| 272 | trifluoromethyl- | 1 | 2-chloroallyl- |
| 273 | methyl- | 2 | 2-chloroallyl- |
| 274 | chloro- | 2 | 2-chloroallyl- |
| 275 | bromo- | 2 | 2-chloroallyl- |
| 276 | trifluoromethyl- | 2 | 2-chloroallyl- |
| 277 | methyl- | 0 | propargyl- |
| 278 | chloro- | 0 | propargyl- |
| 279 | bromo- | 0 | propargyl- |
| 280 | trifluoromethyl- | 0 | propargyl- |
| 281 | methyl- | 1 | propargyl- |
| 282 | chloro- | 1 | propargyl- |
| 283 | bromo- | 1 | propargyl- |
| 284 | trifluoromethyl- | 1 | propargyl- |
| 285 | methyl- | 2 | propargyl- |
| 286 | chloro- | 2 | propargyl- |
| 287 | bromo- | 2 | propargyl- |
| 288 | trifluoromethyl- | 2 | propargyl- |
| 289 | methyl- | 0 | but-2-ynyl- |
| 290 | chloro- | 0 | but-2-ynyl- |
| 291 | bromo- | 0 | but-2-ynyl- |
| 292 | trifluoromethyl- | 0 | but-2-ynyl- |
| 293 | methyl- | 1 | but-2-ynyl- |
| 294 | chloro- | 1 | but-2-ynyl- |
| 295 | bromo- | 1 | but-2-ynyl- |
| 296 | trifluoromethyl- | 1 | but-2-ynyl- |
| 297 | methyl- | 2 | but-2-ynyl- |

TABLE P-continued

| | R5b | n | R2 |
|---|---|---|---|
| 298 | chloro- | 2 | but-2-ynyl- |
| 299 | bromo- | 2 | but-2-ynyl- |
| 300 | trifluoromethyl- | 2 | but-2-ynyl- |
| 301 | methyl- | 0 | but-3-ynyl- |
| 302 | chloro- | 0 | but-3-ynyl- |
| 303 | bromo- | 0 | but-3-ynyl- |
| 304 | trifluoromethyl- | 0 | but-3-ynyl- |
| 305 | methyl- | 1 | but-3-ynyl- |
| 306 | chloro- | 1 | but-3-ynyl- |
| 307 | bromo- | 1 | but-3-ynyl- |
| 308 | trifluoromethyl- | 1 | but-3-ynyl- |
| 309 | methyl- | 2 | but-3-ynyl- |
| 310 | chloro- | 2 | but-3-ynyl- |
| 311 | bromo- | 2 | but-3-ynyl- |
| 312 | trifluoromethyl- | 2 | but-3-ynyl- |
| 313 | methyl- | 0 | benzyl- |
| 314 | chloro- | 0 | benzyl- |
| 315 | bromo- | 0 | benzyl- |
| 316 | trifluoromethyl- | 0 | benzyl- |
| 317 | methyl- | 1 | benzyl- |
| 318 | chloro- | 1 | benzyl- |
| 319 | bromo- | 1 | benzyl- |
| 320 | trifluoromethyl- | 1 | benzyl- |
| 321 | methyl- | 2 | benzyl- |
| 322 | chloro- | 2 | benzyl- |
| 323 | bromo- | 2 | benzyl- |
| 324 | trifluoromethyl- | 2 | benzyl- |
| 325 | methyl- | 0 | cyclopropyl- |
| 326 | chloro- | 0 | cyclopropyl- |
| 327 | bromo- | 0 | cyclopropyl- |
| 328 | trifluoromethyl- | 0 | cyclopropyl- |
| 329 | methyl- | 1 | cyclopropyl- |
| 330 | chloro- | 1 | cyclopropyl- |
| 331 | bromo- | 1 | cyclopropyl- |
| 332 | trifluoromethyl- | 1 | cyclopropyl- |
| 333 | methyl- | 2 | cyclopropyl- |
| 334 | chloro- | 2 | cyclopropyl- |
| 335 | bromo- | 2 | cyclopropyl- |
| 336 | trifluoromethyl- | 2 | cyclopropyl- |
| 337 | methyl- | 0 | cyclobutyl- |
| 338 | chloro- | 0 | cyclobutyl- |
| 339 | bromo- | 0 | cyclobutyl- |
| 340 | trifluoromethyl- | 0 | cyclobutyl- |
| 341 | methyl- | 1 | cyclobutyl- |
| 342 | chloro- | 1 | cyclobutyl- |
| 343 | bromo- | 1 | cyclobutyl- |
| 344 | trifluoromethyl- | 1 | cyclobutyl- |
| 345 | methyl- | 2 | cyclobutyl- |
| 346 | chloro- | 2 | cyclobutyl- |
| 347 | bromo- | 2 | cyclobutyl- |
| 348 | trifluoromethyl- | 2 | cyclobutyl- |
| 349 | methyl- | 0 | cyclopentyl- |
| 350 | chloro- | 0 | cyclopentyl- |
| 351 | bromo- | 0 | cyclopentyl- |
| 352 | trifluoromethyl- | 0 | cyclopentyl- |
| 353 | methyl- | 1 | cyclopentyl- |
| 354 | chloro- | 1 | cyclopentyl- |
| 355 | bromo- | 1 | cyclopentyl- |
| 356 | trifluoromethyl- | 1 | cyclopentyl- |
| 357 | methyl- | 2 | cyclopentyl- |
| 358 | chloro- | 2 | cyclopentyl- |
| 359 | bromo- | 2 | cyclopentyl- |
| 360 | trifluoromethyl- | 2 | cyclopentyl- |
| 361 | methyl- | 0 | cyclopropyl-methyl- |
| 362 | chloro- | 0 | cyclopropyl-methyl- |
| 363 | bromo- | 0 | cyclopropyl-methyl- |
| 364 | trifluoromethyl- | 0 | cyclopropyl-methyl- |
| 365 | methyl- | 1 | cyclopropyl-methyl- |
| 366 | chloro- | 1 | cyclopropyl-methyl- |
| 367 | bromo- | 1 | cyclopropyl-methyl- |
| 368 | trifluoromethyl- | 1 | cyclopropyl-methyl- |
| 369 | methyl- | 2 | cyclopropyl-methyl- |
| 370 | chloro- | 2 | cyclopropyl-methyl- |
| 371 | bromo- | 2 | cyclopropyl-methyl- |
| 372 | trifluoromethyl- | 2 | cyclopropyl-methyl- |
| 373 | methyl- | 0 | cyclobutyl-methyl- |
| 374 | chloro- | 0 | cyclobutyl-methyl- |
| 375 | bromo- | 0 | cyclobutyl-methyl- |
| 376 | trifluoromethyl- | 0 | cyclobutyl-methyl- |
| 377 | methyl- | 1 | cyclobutyl-methyl- |
| 378 | chloro- | 1 | cyclobutyl-methyl- |
| 379 | bromo- | 1 | cyclobutyl-methyl- |
| 380 | trifluoromethyl- | 1 | cyclobutyl-methyl- |
| 381 | methyl- | 2 | cyclobutyl-methyl- |
| 382 | chloro- | 2 | cyclobutyl-methyl- |
| 383 | bromo- | 2 | cyclobutyl-methyl- |
| 384 | trifluoromethyl- | 2 | cyclobutyl-methyl- |
| 385 | methyl- | 0 | thietan-3-yl- |
| 386 | chloro- | 0 | thietan-3-yl- |
| 387 | bromo- | 0 | thietan-3-yl- |
| 388 | trifluoromethyl- | 0 | thietan-3-yl- |
| 389 | methyl- | 1 | thietan-3-yl- |
| 390 | chloro- | 1 | thietan-3-yl- |
| 391 | bromo- | 1 | thietan-3-yl- |
| 392 | trifluoromethyl- | 1 | thietan-3-yl- |
| 393 | methyl- | 2 | thietan-3-yl- |
| 394 | chloro- | 2 | thietan-3-yl- |
| 395 | bromo- | 2 | thietan-3-yl- |
| 396 | trifluoromethyl- | 2 | thietan-3-yl- |
| 397 | methyl- | 0 | 1-oxo-thietan-3-yl- |
| 398 | chloro- | 0 | 1-oxo-thietan-3-yl- |
| 399 | bromo- | 0 | 1-oxo-thietan-3-yl- |
| 400 | trifluoromethyl- | 0 | 1-oxo-thietan-3-yl- |
| 401 | methyl- | 1 | 1-oxo-thietan-3-yl- |
| 402 | chloro- | 1 | 1-oxo-thietan-3-yl- |
| 403 | bromo- | 1 | 1-oxo-thietan-3-yl- |
| 404 | trifluoromethyl- | 1 | 1-oxo-thietan-3-yl- |
| 405 | methyl- | 2 | 1-oxo-thietan-3-yl- |
| 406 | chloro- | 2 | 1-oxo-thietan-3-yl- |
| 407 | bromo- | 2 | 1-oxo-thietan-3-yl- |
| 408 | trifluoromethyl- | 2 | 1-oxo-thietan-3-yl- |
| 409 | methyl- | 0 | 1,1-dioxo-thietan-3-yl- |
| 410 | chloro- | 0 | 1,1-dioxo-thietan-3-yl- |
| 411 | bromo- | 0 | 1,1-dioxo-thietan-3-yl- |
| 412 | trifluoromethyl- | 0 | 1,1-dioxo-thietan-3-yl- |
| 413 | methyl- | 1 | 1,1-dioxo-thietan-3-yl- |
| 414 | chloro- | 1 | 1,1-dioxo-thietan-3-yl- |
| 415 | bromo- | 1 | 1,1-dioxo-thietan-3-yl- |
| 416 | trifluoromethyl- | 1 | 1,1-dioxo-thietan-3-yl- |
| 417 | methyl- | 2 | 1,1-dioxo-thietan-3-yl- |
| 418 | chloro- | 2 | 1,1-dioxo-thietan-3-yl- |
| 419 | bromo- | 2 | 1,1-dioxo-thietan-3-yl- |
| 420 | trifluoromethyl- | 2 | 1,1-dioxo-thietan-3-yl- |
| 421 | methyl- | 0 | 3-methyl-thietan-3-yl- |
| 422 | chloro- | 0 | 3-methyl-thietan-3-yl- |
| 423 | bromo- | 0 | 3-methyl-thietan-3-yl- |
| 424 | trifluoromethyl- | 0 | 3-methyl-thietan-3-yl- |
| 425 | methyl- | 1 | 3-methyl-thietan-3-yl- |
| 426 | chloro- | 1 | 3-methyl-thietan-3-yl- |
| 427 | bromo- | 1 | 3-methyl-thietan-3-yl- |
| 428 | trifluoromethyl- | 1 | 3-methyl-thietan-3-yl- |
| 429 | methyl- | 2 | 3-methyl-thietan-3-yl- |
| 430 | chloro- | 2 | 3-methyl-thietan-3-yl- |
| 431 | bromo- | 2 | 3-methyl-thietan-3-yl- |
| 432 | trifluoromethyl- | 2 | 3-methyl-thietan-3-yl- |
| 433 | methyl- | 0 | thietan-3-ylmethyl- |
| 434 | chloro- | 0 | thietan-3-ylmethyl- |
| 435 | bromo- | 0 | thietan-3-ylmethyl- |
| 436 | trifluoromethyl- | 0 | thietan-3-ylmethyl- |
| 437 | methyl- | 1 | thietan-3-ylmethyl- |
| 438 | chloro- | 1 | thietan-3-ylmethyl- |
| 439 | bromo- | 1 | thietan-3-ylmethyl- |
| 440 | trifluoromethyl- | 1 | thietan-3-ylmethyl- |
| 441 | methyl- | 2 | thietan-3-ylmethyl- |
| 442 | chloro- | 2 | thietan-3-ylmethyl- |
| 443 | bromo- | 2 | thietan-3-ylmethyl- |
| 444 | trifluoromethyl- | 2 | thietan-3-ylmethyl- |
| 445 | methyl- | 0 | (1,1-dioxothietan-3-yl)methyl- |
| 446 | chloro- | 0 | (1,1-dioxothietan-3-yl)methyl- |
| 447 | bromo- | 0 | (1,1-dioxothietan-3-yl)methyl- |
| 448 | trifluoromethyl- | 0 | (1,1-dioxothietan-3-yl)methyl- |
| 449 | methyl- | 1 | (1,1-dioxothietan-3-yl)methyl- |
| 450 | chloro- | 1 | (1,1-dioxothietan-3-yl)methyl- |
| 451 | bromo- | 1 | (1,1-dioxothietan-3-yl)methyl- |
| 452 | trifluoromethyl- | 1 | (1,1-dioxothietan-3-yl)methyl- |
| 453 | methyl- | 2 | (1,1-dioxothietan-3-yl)methyl- |

TABLE P-continued

|  | R5b | n | R2 |
|---|---|---|---|
| 454 | chloro- | 2 | (1,1-dioxothietan-3-yl)methyl- |
| 455 | bromo- | 2 | (1,1-dioxothietan-3-yl)methyl- |
| 456 | trifluoromethyl- | 2 | (1,1-dioxothietan-3-yl)methyl- |
| 457 | methyl- | 0 | (1-oxothietan-3-yl)methyl- |
| 458 | chloro- | 0 | (1-oxothietan-3-yl)methyl- |
| 459 | bromo- | 0 | (1-oxothietan-3-yl)methyl- |
| 460 | trifluoromethyl- | 0 | (1-oxothietan-3-yl)methyl- |
| 461 | methyl- | 1 | (1-oxothietan-3-yl)methyl- |
| 462 | chloro- | 1 | (1-oxothietan-3-yl)methyl- |
| 463 | bromo- | 1 | (1-oxothietan-3-yl)methyl- |
| 464 | trifluoromethyl- | 1 | (1-oxothietan-3-yl)methyl- |
| 465 | methyl- | 2 | (1-oxothietan-3-yl)methyl- |
| 466 | chloro- | 2 | (1-oxothietan-3-yl)methyl- |
| 467 | bromo- | 2 | (1-oxothietan-3-yl)methyl- |
| 468 | trifluoromethyl- | 2 | (1-oxothietan-3-yl)methyl- |
| 469 | methyl- | 0 | cis-1-oxo-thietan-3-yl- |
| 470 | chloro- | 0 | cis-1-oxo-thietan-3-yl- |
| 471 | bromo- | 0 | cis-1-oxo-thietan-3-yl- |
| 472 | trifluoromethyl- | 0 | cis-1-oxo-thietan-3-yl- |
| 473 | methyl- | 1 | cis-1-oxo-thietan-3-yl- |
| 474 | chloro- | 1 | cis-1-oxo-thietan-3-yl- |
| 475 | bromo- | 1 | cis-1-oxo-thietan-3-yl- |
| 476 | trifluoromethyl- | 1 | cis-1-oxo-thietan-3-yl- |
| 477 | methyl- | 2 | cis-1-oxo-thietan-3-yl- |
| 478 | chloro- | 2 | cis-1-oxo-thietan-3-yl- |
| 479 | bromo- | 2 | cis-1-oxo-thietan-3-yl- |
| 480 | trifluoromethyl- | 2 | cis-1-oxo-thietan-3-yl- |
| 481 | methyl- | 0 | cis-1-oxo-thietan-3-ylmethyl- |
| 482 | chloro- | 0 | cis-1-oxo-thietan-3-ylmethyl- |
| 483 | bromo- | 0 | cis-1-oxo-thietan-3-ylmethyl- |
| 484 | trifluoromethyl- | 0 | cis-1-oxo-thietan-3-ylmethyl- |
| 485 | methyl- | 1 | cis-1-oxo-thietan-3-ylmethyl- |
| 486 | chloro- | 1 | cis-1-oxo-thietan-3-ylmethyl- |
| 487 | bromo- | 1 | cis-1-oxo-thietan-3-ylmethyl- |
| 488 | trifluoromethyl- | 1 | cis-1-oxo-thietan-3-ylmethyl- |
| 489 | methyl- | 2 | cis-1-oxo-thietan-3-ylmethyl- |
| 490 | chloro- | 2 | cis-1-oxo-thietan-3-ylmethyl- |
| 491 | bromo- | 2 | cis-1-oxo-thietan-3-ylmethyl- |
| 492 | trifluoromethyl- | 2 | cis-1-oxo-thietan-3-ylmethyl- |
| 493 | methyl- | 0 | (pyrid-2-yl)-methyl- |
| 494 | chloro- | 0 | (pyrid-2-yl)-methyl- |
| 495 | bromo- | 0 | (pyrid-2-yl)-methyl- |
| 496 | trifluoromethyl- | 0 | (pyrid-2-yl)-methyl- |
| 497 | methyl- | 1 | (pyrid-2-yl)-methyl- |
| 498 | chloro- | 1 | (pyrid-2-yl)-methyl- |
| 499 | bromo- | 1 | (pyrid-2-yl)-methyl- |
| 500 | trifluoromethyl- | 1 | (pyrid-2-yl)-methyl- |
| 501 | methyl- | 2 | (pyrid-2-yl)-methyl- |
| 502 | chloro- | 2 | (pyrid-2-yl)-methyl- |
| 503 | bromo- | 2 | (pyrid-2-yl)-methyl- |
| 504 | trifluoromethyl- | 2 | (pyrid-2-yl)-methyl- |
| 505 | methyl- | 0 | (pyrid-3-yl)-methyl- |
| 506 | chloro- | 0 | (pyrid-3-yl)-methyl- |
| 507 | bromo- | 0 | (pyrid-3-yl)-methyl- |
| 508 | trifluoromethyl- | 0 | (pyrid-3-yl)-methyl- |
| 509 | methyl- | 1 | (pyrid-3-yl)-methyl- |
| 510 | chloro- | 1 | (pyrid-3-yl)-methyl- |
| 511 | bromo- | 1 | (pyrid-3-yl)-methyl- |
| 512 | trifluoromethyl- | 1 | (pyrid-3-yl)-methyl- |
| 513 | methyl- | 2 | (pyrid-3-yl)-methyl- |
| 514 | chloro- | 2 | (pyrid-3-yl)-methyl- |
| 515 | bromo- | 2 | (pyrid-3-yl)-methyl- |
| 516 | trifluoromethyl- | 2 | (pyrid-3-yl)-methyl- |
| 517 | methyl- | 0 | (pyrid-4-yl)-methyl- |
| 518 | chloro- | 0 | (pyrid-4-yl)-methyl- |
| 519 | bromo- | 0 | (pyrid-4-yl)-methyl- |
| 520 | trifluoromethyl- | 0 | (pyrid-4-yl)-methyl- |
| 521 | methyl- | 1 | (pyrid-4-yl)-methyl- |
| 522 | chloro- | 1 | (pyrid-4-yl)-methyl- |
| 523 | bromo- | 1 | (pyrid-4-yl)-methyl- |
| 524 | trifluoromethyl- | 1 | (pyrid-4-yl)-methyl- |
| 525 | methyl- | 2 | (pyrid-4-yl)-methyl- |
| 526 | chloro- | 2 | (pyrid-4-yl)-methyl- |
| 527 | bromo- | 2 | (pyrid-4-yl)-methyl- |
| 528 | trifluoromethyl- | 2 | (pyrid-4-yl)-methyl- |
| 529 | methyl- | 0 | oxetan-3yl- |
| 530 | chloro- | 0 | oxetan-3yl- |
| 531 | bromo- | 0 | oxetan-3yl- |
| 532 | trifluoromethyl- | 0 | oxetan-3yl- |
| 533 | methyl- | 1 | oxetan-3yl- |
| 534 | chloro- | 1 | oxetan-3yl- |
| 535 | bromo- | 1 | oxetan-3yl- |
| 536 | trifluoromethyl- | 1 | oxetan-3yl- |
| 537 | methyl- | 2 | oxetan-3yl- |
| 538 | chloro- | 2 | oxetan-3yl- |
| 539 | bromo- | 2 | oxetan-3yl- |
| 540 | trifluoromethyl- | 2 | oxetan-3yl- |
| 541 | methyl- | 0 | oxetan-3ylmethyl |
| 542 | chloro- | 0 | oxetan-3ylmethyl |
| 543 | bromo- | 0 | oxetan-3ylmethyl |
| 544 | trifluoromethyl- | 0 | oxetan-3ylmethyl |
| 545 | methyl- | 1 | oxetan-3ylmethyl |
| 546 | chloro- | 1 | oxetan-3ylmethyl |
| 547 | bromo- | 1 | oxetan-3ylmethyl |
| 548 | trifluoromethyl- | 1 | oxetan-3ylmethyl |
| 549 | methyl- | 2 | oxetan-3ylmethyl |
| 550 | chloro- | 2 | oxetan-3ylmethyl |
| 551 | bromo- | 2 | oxetan-3ylmethyl |
| 552 | trifluoromethyl- | 2 | oxetan-3ylmethyl |
| 553 | methyl- | 0 | (tetrahydrofuran-2-yl)-methyl- |
| 554 | chloro- | 0 | (tetrahydrofuran-2-yl)-methyl- |
| 555 | bromo- | 0 | (tetrahydrofuran-2-yl)-methyl- |
| 556 | trifluoromethyl- | 0 | (tetrahydrofuran-2-yl)-methyl- |
| 557 | methyl- | 1 | (tetrahydrofuran-2-yl)-methyl- |
| 558 | chloro- | 1 | (tetrahydrofuran-2-yl)-methyl- |
| 559 | bromo- | 1 | (tetrahydrofuran-2-yl)-methyl- |
| 560 | trifluoromethyl- | 1 | (tetrahydrofuran-2-yl)-methyl- |
| 561 | methyl- | 2 | (tetrahydrofuran-2-yl)-methyl- |
| 562 | chloro- | 2 | (tetrahydrofuran-2-yl)-methyl- |
| 563 | bromo- | 2 | (tetrahydrofuran-2-yl)-methyl- |
| 564 | trifluoromethyl- | 2 | (tetrahydrofuran-2-yl)-methyl- |
| 565 | methyl- | 0 | (tetrahydrofuran-3-yl)-methyl- |
| 566 | chloro- | 0 | (tetrahydrofuran-3-yl)-methyl- |
| 567 | bromo- | 0 | (tetrahydrofuran-3-yl)-methyl- |
| 568 | trifluoromethyl- | 0 | (tetrahydrofuran-3-yl)-methyl- |
| 569 | methyl- | 1 | (tetrahydrofuran-3-yl)-methyl- |
| 570 | chloro- | 1 | (tetrahydrofuran-3-yl)-methyl- |
| 571 | bromo- | 1 | (tetrahydrofuran-3-yl)-methyl- |
| 572 | trifluoromethyl- | 1 | (tetrahydrofuran-3-yl)-methyl- |
| 573 | methyl- | 2 | (tetrahydrofuran-3-yl)-methyl- |
| 574 | chloro- | 2 | (tetrahydrofuran-3-yl)-methyl- |
| 575 | bromo- | 2 | (tetrahydrofuran-3-yl)-methyl- |
| 576 | trifluoromethyl- | 2 | (tetrahydrofuran-3-yl)-methyl- |
| 577 | methyl- | 0 | (4-fluorophenyl)-methyl- |
| 578 | chloro- | 0 | (4-fluorophenyl)-methyl- |
| 579 | bromo- | 0 | (4-fluorophenyl)-methyl- |
| 580 | trifluoromethyl- | 0 | (4-fluorophenyl)-methyl- |
| 581 | methyl- | 1 | (4-fluorophenyl)-methyl- |
| 582 | chloro- | 1 | (4-fluorophenyl)-methyl- |
| 583 | bromo- | 1 | (4-fluorophenyl)-methyl- |
| 584 | trifluoromethyl- | 1 | (4-fluorophenyl)-methyl- |
| 585 | methyl- | 2 | (4-fluorophenyl)-methyl- |
| 586 | chloro- | 2 | (4-fluorophenyl)-methyl- |
| 587 | bromo- | 2 | (4-fluorophenyl)-methyl- |
| 588 | trifluoromethyl- | 2 | (4-fluorophenyl)-methyl- |
| 589 | methyl- | 0 | (4-chlorophenyl)-methyl- |
| 590 | chloro- | 0 | (4-chlorophenyl)-methyl- |
| 591 | bromo- | 0 | (4-chlorophenyl)-methyl- |
| 592 | trifluoromethyl- | 0 | (4-chlorophenyl)-methyl- |
| 593 | methyl- | 1 | (4-chlorophenyl)-methyl- |
| 594 | chloro- | 1 | (4-chlorophenyl)-methyl- |
| 595 | bromo- | 1 | (4-chlorophenyl)-methyl- |
| 596 | trifluoromethyl- | 1 | (4-chlorophenyl)-methyl- |
| 597 | methyl- | 2 | (4-chlorophenyl)-methyl- |
| 598 | chloro- | 2 | (4-chlorophenyl)-methyl- |
| 599 | bromo- | 2 | (4-chlorophenyl)-methyl- |
| 600 | trifluoromethyl- | 2 | (4-chlorophenyl)-methyl- |
| 601 | methyl- | 0 | 4-fluorophenyl- |
| 602 | chloro- | 0 | 4-fluorophenyl- |
| 603 | bromo- | 0 | 4-fluorophenyl- |
| 604 | trifluoromethyl- | 0 | 4-fluorophenyl- |
| 605 | methyl- | 1 | 4-fluorophenyl- |
| 606 | chloro- | 1 | 4-fluorophenyl- |
| 607 | bromo- | 1 | 4-fluorophenyl- |
| 608 | trifluoromethyl- | 1 | 4-fluorophenyl- |
| 609 | methyl- | 2 | 4-fluorophenyl- |

TABLE P-continued

|     | R5b             | n | R2                          |
|-----|-----------------|---|-----------------------------|
| 610 | chloro-         | 2 | 4-fluorophenyl-             |
| 611 | bromo-          | 2 | 4-fluorophenyl-             |
| 612 | trifluoromethyl-| 2 | 4-fluorophenyl-             |
| 613 | methyl-         | 0 | 4-chlorophenyl-             |
| 614 | chloro-         | 0 | 4-chlorophenyl-             |
| 615 | bromo-          | 0 | 4-chlorophenyl-             |
| 616 | trifluoromethyl-| 0 | 4-chlorophenyl-             |
| 617 | methyl-         | 1 | 4-chlorophenyl-             |
| 618 | chloro-         | 1 | 4-chlorophenyl-             |
| 619 | bromo-          | 1 | 4-chlorophenyl-             |
| 620 | trifluoromethyl-| 1 | 4-chlorophenyl-             |
| 621 | methyl-         | 2 | 4-chlorophenyl-             |
| 622 | chloro-         | 2 | 4-chlorophenyl-             |
| 623 | bromo-          | 2 | 4-chlorophenyl-             |
| 624 | trifluoromethyl-| 2 | 4-chlorophenyl-             |
| 625 | methyl-         | 0 | 2-furylmethyl-              |
| 626 | chloro-         | 0 | 2-furylmethyl-              |
| 627 | bromo-          | 0 | 2-furylmethyl-              |
| 628 | trifluoromethyl-| 0 | 2-furylmethyl-              |
| 629 | methyl-         | 1 | 2-furylmethyl-              |
| 630 | chloro-         | 1 | 2-furylmethyl-              |
| 631 | bromo-          | 1 | 2-furylmethyl-              |
| 632 | trifluoromethyl-| 1 | 2-furylmethyl-              |
| 633 | methyl-         | 2 | 2-furylmethyl-              |
| 634 | chloro-         | 2 | 2-furylmethyl-              |
| 635 | bromo-          | 2 | 2-furylmethyl-              |
| 636 | trifluoromethyl-| 2 | 2-furylmethyl-              |
| 637 | methyl-         | 0 | (4-chloro-pyrid-2-yl)-methyl-|
| 638 | chloro-         | 0 | (4-chloro-pyrid-2-yl)-methyl-|
| 639 | bromo-          | 0 | (4-chloro-pyrid-2-yl)-methyl-|
| 640 | trifluoromethyl-| 0 | (4-chloro-pyrid-2-yl)-methyl-|
| 641 | methyl-         | 1 | (4-chloro-pyrid-2-yl)-methyl-|
| 642 | chloro-         | 1 | (4-chloro-pyrid-2-yl)-methyl-|
| 643 | bromo-          | 1 | (4-chloro-pyrid-2-yl)-methyl-|
| 644 | trifluoromethyl-| 1 | (4-chloro-pyrid-2-yl)-methyl-|
| 645 | methyl-         | 2 | (4-chloro-pyrid-2-yl)-methyl-|
| 646 | chloro-         | 2 | (4-chloro-pyrid-2-yl)-methyl-|
| 647 | bromo-          | 2 | (4-chloro-pyrid-2-yl)-methyl-|
| 648 | trifluoromethyl-| 2 | (4-chloro-pyrid-2-yl)-methyl-|
| 649 | methyl-         | 0 | (4-chloro-pyrid-3-yl)-methyl-|
| 650 | chloro-         | 0 | (4-chloro-pyrid-3-yl)-methyl-|
| 651 | bromo-          | 0 | (4-chloro-pyrid-3-yl)-methyl-|
| 652 | trifluoromethyl-| 0 | (4-chloro-pyrid-3-yl)-methyl-|
| 653 | methyl-         | 1 | (4-chloro-pyrid-3-yl)-methyl-|
| 654 | chloro-         | 1 | (4-chloro-pyrid-3-yl)-methyl-|
| 655 | bromo-          | 1 | (4-chloro-pyrid-3-yl)-methyl-|
| 656 | trifluoromethyl-| 1 | (4-chloro-pyrid-3-yl)-methyl-|
| 657 | methyl-         | 2 | (4-chloro-pyrid-3-yl)-methyl-|
| 658 | chloro-         | 2 | (4-chloro-pyrid-3-yl)-methyl-|
| 659 | bromo-          | 2 | (4-chloro-pyrid-3-yl)-methyl-|
| 660 | trifluoromethyl-| 2 | (4-chloro-pyrid-3-yl)-methyl-|
| 661 | methyl-         | 0 | (3-chloro-pyrid-4-yl)-methyl-|
| 662 | chloro-         | 0 | (3-chloro-pyrid-4-yl)-methyl-|
| 663 | bromo-          | 0 | (3-chloro-pyrid-4-yl)-methyl-|
| 664 | trifluoromethyl-| 0 | (3-chloro-pyrid-4-yl)-methyl-|
| 665 | methyl-         | 1 | (3-chloro-pyrid-4-yl)-methyl-|
| 666 | chloro-         | 1 | (3-chloro-pyrid-4-yl)-methyl-|
| 667 | bromo-          | 1 | (3-chloro-pyrid-4-yl)-methyl-|
| 668 | trifluoromethyl-| 1 | (3-chloro-pyrid-4-yl)-methyl-|
| 669 | methyl-         | 2 | (3-chloro-pyrid-4-yl)-methyl-|
| 670 | chloro-         | 2 | (3-chloro-pyrid-4-yl)-methyl-|
| 671 | bromo-          | 2 | (3-chloro-pyrid-4-yl)-methyl-|
| 672 | trifluoromethyl-| 2 | (3-chloro-pyrid-4-yl)-methyl-|
| 673 | methyl-         | 0 | 2-cyano-ethyl                |
| 674 | chloro-         | 0 | 2-cyano-ethyl                |
| 675 | bromo-          | 0 | 2-cyano-ethyl                |
| 676 | trifluoromethyl-| 0 | 2-cyano-ethyl                |
| 677 | methyl-         | 1 | 2-cyano-ethyl                |
| 678 | chloro-         | 1 | 2-cyano-ethyl                |
| 679 | bromo-          | 1 | 2-cyano-ethyl                |
| 680 | trifluoromethyl-| 1 | 2-cyano-ethyl                |
| 681 | methyl-         | 2 | 2-cyano-ethyl                |
| 682 | chloro-         | 2 | 2-cyano-ethyl                |
| 683 | bromo-          | 2 | 2-cyano-ethyl                |
| 684 | trifluoromethyl-| 2 | 2-cyano-ethyl                |
| 685 | methyl-         | 0 | 2-methoxy-ethyl-             |
| 686 | chloro-         | 0 | 2-methoxy-ethyl-             |
| 687 | bromo-          | 0 | 2-methoxy-ethyl-             |
| 688 | trifluoromethyl-| 0 | 2-methoxy-ethyl-             |
| 689 | methyl-         | 1 | 2-methoxy-ethyl-             |
| 690 | chloro-         | 1 | 2-methoxy-ethyl-             |
| 691 | bromo-          | 1 | 2-methoxy-ethyl-             |
| 692 | trifluoromethyl-| 1 | 2-methoxy-ethyl-             |
| 693 | methyl-         | 2 | 2-methoxy-ethyl-             |
| 694 | chloro-         | 2 | 2-methoxy-ethyl-             |
| 695 | bromo-          | 2 | 2-methoxy-ethyl-             |
| 696 | trifluoromethyl-| 2 | 2-methoxy-ethyl-             |
| 697 | methyl-         | 0 | 1-methylthio-prop-2-yl-      |
| 698 | chloro-         | 0 | 1-methylthio-prop-2-yl-      |
| 699 | bromo-          | 0 | 1-methylthio-prop-2-yl-      |
| 700 | trifluoromethyl-| 0 | 1-methylthio-prop-2-yl-      |
| 701 | methyl-         | 1 | 1-methylthio-prop-2-yl-      |
| 702 | chloro-         | 1 | 1-methylthio-prop-2-yl-      |
| 703 | bromo-          | 1 | 1-methylthio-prop-2-yl-      |
| 704 | trifluoromethyl-| 1 | 1-methylthio-prop-2-yl-      |
| 705 | methyl-         | 2 | 1-methylthio-prop-2-yl-      |
| 706 | chloro-         | 2 | 1-methylthio-prop-2-yl-      |
| 707 | bromo-          | 2 | 1-methylthio-prop-2-yl-      |
| 708 | trifluoromethyl-| 2 | 1-methylthio-prop-2-yl-      |
| 709 | methyl-         | 0 | 2-methylthio-ethyl-          |
| 710 | chloro-         | 0 | 2-methylthio-ethyl-          |
| 711 | bromo-          | 0 | 2-methylthio-ethyl-          |
| 712 | trifluoromethyl-| 0 | 2-methylthio-ethyl-          |
| 713 | methyl-         | 1 | 2-methylthio-ethyl-          |
| 714 | chloro-         | 1 | 2-methylthio-ethyl-          |
| 715 | bromo-          | 1 | 2-methylthio-ethyl-          |
| 716 | trifluoromethyl-| 1 | 2-methylthio-ethyl-          |
| 717 | methyl-         | 2 | 2-methylthio-ethyl-          |
| 718 | chloro-         | 2 | 2-methylthio-ethyl-          |
| 719 | bromo-          | 2 | 2-methylthio-ethyl-          |
| 720 | trifluoromethyl-| 2 | 2-methylthio-ethyl-          |

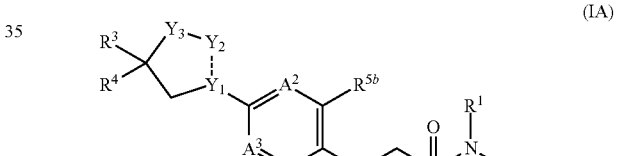

(IA)

Table 1

Table 1 provides 720 compounds of formula IA wherein R1 is hydrogen, R3 is trifluoromethyl-, R4 is 3,5-dichlorophenyl-, Y1-Y2-Y3 is —C═N—O—, A2 is CH, A3 is CH, A4 is CH, and R5b, n and R2 are as defined in Table P.

Table 2

Table 2 provides 720 compounds of formula IA wherein R1 is methyl-, R3 is trifluoromethyl-, R4 is 3,5-dichlorophenyl-, Y1-Y2-Y3 is —C═N—O—, A2 is CH, A3 is CH, A4 is CH, and R5b, n and R2 are as defined in Table P.

Table 3

Table 3 provides 720 compounds of formula IA wherein R1 is ethyl-, R3 is trifluoromethyl-, R4 is 3,5-dichlorophenyl-, Y1-Y2-Y3 is —C═N—O—, A2 is CH, A3 is CH, A4 is CH, and R5b, n and R2 are as defined in Table P.

Table 4

Table 4 provides 720 compounds of formula IA wherein R1 is hydrogen, R3 is dichloromethyl-, R4 is 3,5-dichlorophenyl-, Y1-Y2-Y3 is —C═N—O—, A2 is CH, A3 is CH, A4 is CH, and R5b, n and R2 are as defined in Table P.

Table 5

Table 5 provides 720 compounds of formula IA wherein R1 is methyl-, R3 is dichloromethyl-, R4 is 3,5-dichlorophenyl-, Y1-Y2-Y3 is —C=N—O—, A2 is CH, A3 is CH, A4 is CH, and R5b, n and R2 are as defined in Table P.

Table 6

Table 6 provides 720 compounds of formula IA wherein R1 is ethyl-, R3 is dichloromethyl-, R4 is 3,5-dichlorophenyl-, Y1-Y2-Y3 is —C=N—O—, A2 is CH, A3 is CH, A4 is CH, and R5b, n and R2 are as defined in Table P.

Table 7

Table 7 provides 720 compounds of formula IA wherein R1 is hydrogen, R3 is trifluoromethyl-, R4 is 3,4-dichlorophenyl-, Y1-Y2-Y3 is —C=N—O—, A2 is CH, A3 is CH, A4 is CH, and R5b, n and R2 are as defined in Table P.

Table 8

Table 8 provides 720 compounds of formula IA wherein R1 is methyl-, R3 is trifluoromethyl-, R4 is 3,4-dichlorophenyl-, Y1-Y2-Y3 is —C=N—O—, A2 is CH, A3 is CH, A4 is CH, and R5b, n and R2 are as defined in Table P.

Table 9

Table 9 provides 720 compounds of formula IA wherein R1 is ethyl-, R3 is trifluoromethyl-, R4 is 3,4-dichlorophenyl-, Y1-Y2-Y3 is —C=N—O—, A2 is CH, A3 is CH, A4 is CH, and R5b, n and R2 are as defined in Table P.

Table 10

Table 10 provides 720 compounds of formula IA wherein R1 is hydrogen, R3 is dichloromethyl-, R4 is 3,4-dichlorophenyl-, Y1-Y2-Y3 is —C=N—O—, A2 is CH, A3 is CH, A4 is CH, and R5b, n and R2 are as defined in Table P.

Table 11

Table 11 provides 720 compounds of formula IA wherein R1 is methyl-, R3 is dichloromethyl-, R4 is 3,4-dichlorophenyl-, Y1-Y2-Y3 is —C=N—O—, A2 is CH, A3 is CH, A4 is CH, and R5b, n and R2 are as defined in Table P.

Table 12

Table 12 provides 720 compounds of formula IA wherein R1 is ethyl-, R3 is dichloromethyl-, R4 is 3,4-dichlorophenyl-, Y1-Y2-Y3 is —C=N—O—, A2 is CH, A3 is CH, A4 is CH, and R5b, n and R2 are as defined in Table P.

Table 13

Table 13 provides 720 compounds of formula IA wherein R1 is hydrogen, R3 is trifluoromethyl-, R4 is 3,5-dichloro-4-fluorophenyl-, Y1-Y2-Y3 is —C=N—O—, A2 is CH, A3 is CH, A4 is CH, and R5b, n and R2 are as defined in Table P.

Table 14

Table 14 provides 720 compounds of formula IA wherein R1 is methyl-, R3 is trifluoromethyl-, R4 is 3,5-dichloro-4-fluorophenyl-, Y1-Y2-Y3 is —C=N—O—, A2 is CH, A3 is CH, A4 is CH, and R5b, n and R2 are as defined in Table P.

Table 15

Table 15 provides 720 compounds of formula IA wherein R1 is ethyl-, R3 is trifluoromethyl-, R4 is 3,5-dichloro-4-fluorophenyl-, Y1-Y2-Y3 is —C=N—O—, A2 is CH, A3 is CH, A4 is CH, and R5b, n and R2 are as defined in Table P.

Table 16

Table 16 provides 720 compounds of formula IA wherein R1 is hydrogen, R3 is dichloromethyl-, R4 is 3,5-dichloro-4-fluorophenyl-, Y1-Y2-Y3 is —C=N—O—, A2 is CH, A3 is CH, A4 is CH, and R5b, n and R2 are as defined in Table P.

Table 17

Table 17 provides 720 compounds of formula IA wherein R1 is methyl-, R3 is dichloromethyl-, R4 is 3,5-dichloro-4-fluorophenyl-, Y1-Y2-Y3 is —C=N—O—, A2 is CH, A3 is CH, A4 is CH, and R5b, n and R2 are as defined in Table P.

Table 18

Table 18 provides 720 compounds of formula IA wherein R1 is ethyl-, R3 is dichloromethyl-, R4 is 3,5-dichloro-4-fluorophenyl-, Y1-Y2-Y3 is —C=N—O—, A2 is CH, A3 is CH, A4 is CH, and R5b, n and R2 are as defined in Table P.

Table 19

Table 19 provides 720 compounds of formula IA wherein R1 is hydrogen, R3 is trifluoromethyl-, R4 is 3,4,5-trichlorophenyl-, Y1-Y2-Y3 is —C=N—O—, A2 is CH, A3 is CH, A4 is CH, and R5b, n and R2 are as defined in Table P.

Table 20

Table 20 provides 720 compounds of formula IA wherein R1 is methyl-, R3 is trifluoromethyl-, R4 is 3,4,5-trichlorophenyl-, Y1-Y2-Y3 is —C=N—O—, A2 is CH, A3 is CH, A4 is CH, and R5b, n and R2 are as defined in Table P.

Table 21

Table 21 provides 720 compounds of formula IA wherein R1 is ethyl-, R3 is trifluoromethyl-, R4 is 3,4,5-trichlorophenyl-, Y1-Y2-Y3 is —C=N—O—, A2 is CH, A3 is CH, A4 is CH, and R5b, n and R2 are as defined in Table P.

Table 22

Table 22 provides 720 compounds of formula IA wherein R1 is hydrogen, R3 is dichloromethyl-, R4 is 3,4,5-trichlorophenyl-, Y1-Y2-Y3 is —C=N—O—, A2 is CH, A3 is CH, A4 is CH, and R5b, n and R2 are as defined in Table P.

Table 23

Table 23 provides 720 compounds of formula IA wherein R1 is methyl-, R3 is dichloromethyl-, R4 is 3,4,5-trichlorophenyl-, Y1-Y2-Y3 is —C=N—O—, A2 is CH, A3 is CH, A4 is CH, and R5b, n and R2 are as defined in Table P.

Table 24

Table 24 provides 720 compounds of formula IA wherein R1 is ethyl-, R3 is dichloromethyl-, R4 is 3,4,5-trichlorophenyl-, Y1-Y2-Y3 is —C=N—O—, A2 is CH, A3 is CH, A4 is CH, and R5b, n and R2 are as defined in Table P.

Table 25

Table 25 provides 720 compounds of formula IA wherein R1 is hydrogen, R3 is trifluoromethyl-, R4 is 3-chloro-5-fluorophenyl-, Y1-Y2-Y3 is —C=N—O—, A2 is CH, A3 is CH, A4 is CH, and R5b, n and R2 are as defined in Table P.

Table 26

Table 26 provides 720 compounds of formula IA wherein R1 is methyl-, R3 is trifluoromethyl-, R4 is 3-chloro-5-fluorophenyl-, Y1-Y2-Y3 is —C=N—O—, A2 is CH, A3 is CH, A4 is CH, and R5b, n and R2 are as defined in Table P.

Table 27

Table 27 provides 720 compounds of formula IA wherein R1 is ethyl-, R3 is trifluoromethyl-, R4 is 3-chloro-5-fluorophenyl-, Y1-Y2-Y3 is —C=N—O—, A2 is CH, A3 is CH, A4 is CH, and R5b, n and R2 are as defined in Table P.

Table 28

Table 28 provides 720 compounds of formula IA wherein R1 is hydrogen, R3 is dichloromethyl-, R4 is 3-chloro-5- fluorophenyl-, Y1-Y2-Y3 is —C═N—O—, A2 is CH, A3 is CH, A4 is CH, and R5b, n and R2 are as defined in Table P.

Table 29

Table 29 provides 720 compounds of formula IA wherein R1 is methyl-, R3 is dichloromethyl-, R4 is 3-chloro-5-fluorophenyl-, Y1-Y2-Y3 is —C═N—O—, A2 is CH, A3 is CH, A4 is CH, and R5b, n and R2 are as defined in Table P.

Table 30

Table 30 provides 720 compounds of formula IA wherein R1 is ethyl-, R3 is dichloromethyl-, R4 is 3-chloro-5-fluorophenyl-, Y1-Y2-Y3 is —C═N—O—, A2 is CH, A3 is CH, A4 is CH, and R5b, n and R2 are as defined in Table P.

Table 31

Table 31 provides 720 compounds of formula IA wherein R1 is hydrogen, R3 is trifluoromethyl-, R4 is 3-chloro-5-(trifluoromethyl)phenyl-, Y1-Y2-Y3 is —C═N—O—, A2 is CH, A3 is CH, A4 is CH, and R5b, n and R2 are as defined in Table P.

Table 32

Table 32 provides 720 compounds of formula IA wherein R1 is methyl-, R3 is trifluoromethyl-, R4 is 3-chloro-5-(trifluoromethyl)phenyl-, Y1-Y2-Y3 is —C═N—O—, A2 is CH, A3 is CH, A4 is CH, and R5b, n and R2 are as defined in Table P.

Table 33

Table 33 provides 720 compounds of formula IA wherein R1 is ethyl-, R3 is trifluoromethyl-, R4 is 3-chloro-5-(trifluoromethyl)phenyl-, Y1-Y2-Y3 is —C═N—O—, A2 is CH, A3 is CH, A4 is CH, and R5b, n and R2 are as defined in Table P.

Table 34

Table 34 provides 720 compounds of formula IA wherein R1 is hydrogen, R3 is dichloromethyl-, R4 is 3-chloro-5-(trifluoromethyl)phenyl-, Y1-Y2-Y3 is —C═N—O—, A2 is CH, A3 is CH, A4 is CH, and R5b, n and R2 are as defined in Table P.

Table 35

Table 35 provides 720 compounds of formula IA wherein R1 is methyl-, R3 is dichloromethyl-, R4 is 3-chloro-5-(trifluoromethyl)phenyl-, Y1-Y2-Y3 is —C═N—O—, A2 is CH, A3 is CH, A4 is CH, and R5b, n and R2 are as defined in Table P.

Table 36

Table 36 provides 720 compounds of formula IA wherein R1 is ethyl-, R3 is dichloromethyl-, R4 is 3-chloro-5-(trifluoromethyl)phenyl-, Y1-Y2-Y3 is —C═N—O—, A2 is CH, A3 is CH, A4 is CH, and R5b, n and R2 are as defined in Table P.

Table 37

Table 37 provides 720 compounds of formula IA wherein R1 is hydrogen, R3 is trifluoromethyl-, R4 is 3,5-bis(trifluoromethyl)phenyl-, Y1-Y2-Y3 is —C═N—O—, A2 is CH, A3 is CH, A4 is CH, and R5b, n and R2 are as defined in Table P.

Table 38

Table 38 provides 720 compounds of formula IA wherein R1 is methyl-, R3 is trifluoromethyl-, R4 is 3,5-bis(trifluoromethyl)phenyl-, Y1-Y2-Y3 is —C═N—O—, A2 is CH, A3 is CH, A4 is CH, and R5b, n and R2 are as defined in Table P.

Table 39

Table 39 provides 720 compounds of formula IA wherein R1 is ethyl-, R3 is trifluoromethyl-, R4 is 3,5-bis(trifluoromethyl)phenyl-, Y1-Y2-Y3 is —C═N—O—, A2 is CH, A3 is CH, A4 is CH, and R5b, n and R2 are as defined in Table P.

Table 40

Table 40 provides 720 compounds of formula IA wherein R1 is hydrogen, R3 is dichloromethyl-, R4 is 3,5-bis(trifluoromethyl)phenyl-, Y1-Y2-Y3 is —C═N—O—, A2 is CH, A3 is CH, A4 is CH, and R5b, n and R2 are as defined in Table P.

Table 41

Table 41 provides 720 compounds of formula IA wherein R1 is methyl-, R3 is dichloromethyl-, R4 is 3,5-bis(trifluoromethyl)phenyl-, Y1-Y2-Y3 is —C═N—O—, A2 is CH, A3 is CH, A4 is CH, and R5b, n and R2 are as defined in Table P.

Table 42

Table 42 provides 720 compounds of formula IA wherein R1 is ethyl-, R3 is dichloromethyl-, R4 is 3,5-bis(trifluoromethyl)phenyl-, Y1-Y2-Y3 is —C═N—O—, A2 is CH, A3 is CH, A4 is CH, and R5b, n and R2 are as defined in Table P.

Table 43

Table 43 provides 720 compounds of formula IA wherein R1 is hydrogen, R3 is trifluoromethyl-, R4 is 3-(trifluoromethyl)phenyl-, Y1-Y2-Y3 is —C═N—O—, A2 is CH, A3 is CH, A4 is CH, and R5b, n and R2 are as defined in Table P.

Table 44

Table 44 provides 720 compounds of formula IA wherein R1 is methyl-, R3 is trifluoromethyl-, R4 is 3-(trifluoromethyl)phenyl-, Y1-Y2-Y3 is —C═N—O—, A2 is CH, A3 is CH, A4 is CH, and R5b, n and R2 are as defined in Table P.

Table 45

Table 45 provides 720 compounds of formula IA wherein R1 is ethyl-, R3 is trifluoromethyl-, R4 is 3-(trifluoromethyl)phenyl-, Y1-Y2-Y3 is —C═N—O—, A2 is CH, A3 is CH, A4 is CH, and R5b, n and R2 are as defined in Table P.

Table 46

Table 46 provides 720 compounds of formula IA wherein R1 is hydrogen, R3 is dichloromethyl-, R4 is 3-(trifluoromethyl)phenyl-, Y1-Y2-Y3 is —C═N—O—, A2 is CH, A3 is CH, A4 is CH, and R5b, n and R2 are as defined in Table P.

Table 47

Table 47 provides 720 compounds of formula IA wherein R1 is methyl-, R3 is dichloromethyl-, R4 is 3-(trifluoromethyl)phenyl-, Y1-Y2-Y3 is —C═N—O—, A2 is CH, A3 is CH, A4 is CH, and R5b, n and R2 are as defined in Table P.

Table 48

Table 48 provides 720 compounds of formula IA wherein R1 is ethyl-, R3 is dichloromethyl-, R4 is 3-(trifluoromethyl)phenyl-, Y1-Y2-Y3 is —C═N—O—, A2 is CH, A3 is CH, A4 is CH, and R5b, n and R2 are as defined in Table P.

Table 49

Table 49 provides 720 compounds of formula IA wherein R1 is hydrogen, R3 is trifluoromethyl-, R4 is 3,5-dichlorophenyl-, Y1-Y2-Y3 is —C═N—CH2—, A2 is CH, A3 is CH, A4 is CH, and R5b, n and R2 are as defined in Table P.

Table 50

Table 50 provides 720 compounds of formula IA wherein R1 is methyl-, R3 is trifluoromethyl-, R4 is 3,5-dichlorophenyl-, Y1-Y2-Y3 is —C=N—CH2-, A2 is CH, A3 is CH, A4 is CH, and R5b, n and R2 are as defined in Table P.

Table 51

Table 51 provides 720 compounds of formula IA wherein R1 is ethyl-, R3 is trifluoromethyl-, R4 is 3,5-dichlorophenyl-, Y1-Y2-Y3 is —C=N—CH2-, A2 is CH, A3 is CH, A4 is CH, and R5b, n and R2 are as defined in Table P.

Table 52

Table 52 provides 720 compounds of formula IA wherein R1 is hydrogen, R3 is dichloromethyl-, R4 is 3,5-dichlorophenyl-, Y1-Y2-Y3 is —C=N—CH2-, A2 is CH, A3 is CH, A4 is CH, and R5b, n and R2 are as defined in Table P.

Table 53

Table 53 provides 720 compounds of formula IA wherein R1 is methyl-, R3 is dichloromethyl-, R4 is 3,5-dichlorophenyl-, Y1-Y2-Y3 is —C=N—CH2-, A2 is CH, A3 is CH, A4 is CH, and R5b, n and R2 are as defined in Table P.

Table 54

Table 54 provides 720 compounds of formula IA wherein R1 is ethyl-, R3 is dichloromethyl-, R4 is 3,5-dichlorophenyl-, Y1-Y2-Y3 is —C=N—CH2-, A2 is CH, A3 is CH, A4 is CH, and R5b, n and R2 are as defined in Table P.

Table 55

Table 55 provides 720 compounds of formula IA wherein R1 is hydrogen, R3 is trifluoromethyl-, R4 is 3,4-dichlorophenyl-, Y1-Y2-Y3 is —C=N—CH2-, A2 is CH, A3 is CH, A4 is CH, and R5b, n and R2 are as defined in Table P.

Table 56

Table 56 provides 720 compounds of formula IA wherein R1 is methyl-, R3 is trifluoromethyl-, R4 is 3,4-dichlorophenyl-, Y1-Y2-Y3 is —C=N—CH2-, A2 is CH, A3 is CH, A4 is CH, and R5b, n and R2 are as defined in Table P.

Table 57

Table 57 provides 720 compounds of formula IA wherein R1 is ethyl-, R3 is trifluoromethyl-, R4 is 3,4-dichlorophenyl-, Y1-Y2-Y3 is —C=N—CH2-, A2 is CH, A3 is CH, A4 is CH, and R5b, n and R2 are as defined in Table P.

Table 58

Table 58 provides 720 compounds of formula IA wherein R1 is hydrogen, R3 is dichloromethyl-, R4 is 3,4-dichlorophenyl-, Y1-Y2-Y3 is —C=N—CH2-, A2 is CH, A3 is CH, A4 is CH, and R5b, n and R2 are as defined in Table P.

Table 59

Table 59 provides 720 compounds of formula IA wherein R1 is methyl-, R3 is dichloromethyl-, R4 is 3,4-dichlorophenyl-, Y1-Y2-Y3 is —C=N—CH2-, A2 is CH, A3 is CH, A4 is CH, and R5b, n and R2 are as defined in Table P.

Table 60

Table 60 provides 720 compounds of formula IA wherein R1 is ethyl-, R3 is dichloromethyl-, R4 is 3,4-dichlorophenyl-, Y1-Y2-Y3 is —C=N—CH2-, A2 is CH, A3 is CH, A4 is CH, and R5b, n and R2 are as defined in Table P.

Table 61

Table 61 provides 720 compounds of formula IA wherein R1 is hydrogen, R3 is trifluoromethyl-, R4 is 3,5-dichloro-4-fluorophenyl-, Y1-Y2-Y3 is —C=N—CH2-, A2 is CH, A3 is CH, A4 is CH, and R5b, n and R2 are as defined in Table P.

Table 62

Table 62 provides 720 compounds of formula IA wherein R1 is methyl-, R3 is trifluoromethyl-, R4 is 3,5-dichloro-4-fluorophenyl-, Y1-Y2-Y3 is —C=N—CH2-, A2 is CH, A3 is CH, A4 is CH, and R5b, n and R2 are as defined in Table P.

Table 63

Table 63 provides 720 compounds of formula IA wherein R1 is ethyl-, R3 is trifluoromethyl-, R4 is 3,5-dichloro-4-fluorophenyl-, Y1-Y2-Y3 is —C=N—CH2-, A2 is CH, A3 is CH, A4 is CH, and R5b, n and R2 are as defined in Table P.

Table 64

Table 64 provides 720 compounds of formula IA wherein R1 is hydrogen, R3 is dichloromethyl-, R4 is 3,5-dichloro-4-fluorophenyl-, Y1-Y2-Y3 is —C=N—CH2-, A2 is CH, A3 is CH, A4 is CH, and R5b, n and R2 are as defined in Table P.

Table 65

Table 65 provides 720 compounds of formula IA wherein R1 is methyl-, R3 is dichloromethyl-, R4 is 3,5-dichloro-4-fluorophenyl-, Y1-Y2-Y3 is —C=N—CH2-, A2 is CH, A3 is CH, A4 is CH, and R5b, n and R2 are as defined in Table P.

Table 66

Table 66 provides 720 compounds of formula IA wherein R1 is ethyl-, R3 is dichloromethyl-, R4 is 3,5-dichloro-4-fluorophenyl-, Y1-Y2-Y3 is —C=N—CH2-, A2 is CH, A3 is CH, A4 is CH, and R5b, n and R2 are as defined in Table P.

Table 67

Table 67 provides 720 compounds of formula IA wherein R1 is hydrogen, R3 is trifluoromethyl-, R4 is 3,4,5-trichlorophenyl-, Y1-Y2-Y3 is —C=N—CH2-, A2 is CH, A3 is CH, A4 is CH, and R5b, n and R2 are as defined in Table P.

Table 68

Table 68 provides 720 compounds of formula IA wherein R1 is methyl-, R3 is trifluoromethyl-, R4 is 3,4,5-trichlorophenyl-, Y1-Y2-Y3 is —C=N—CH2-, A2 is CH, A3 is CH, A4 is CH, and R5b, n and R2 are as defined in Table P.

Table 69

Table 69 provides 720 compounds of formula IA wherein R1 is ethyl-, R3 is trifluoromethyl-, R4 is 3,4,5-trichlorophenyl-, Y1-Y2-Y3 is —C=N—CH2-, A2 is CH, A3 is CH, A4 is CH, and R5b, n and R2 are as defined in Table P.

Table 70

Table 70 provides 720 compounds of formula IA wherein R1 is hydrogen, R3 is dichloromethyl-, R4 is 3,4,5-trichlorophenyl-, Y1-Y2-Y3 is —C=N—CH2-, A2 is CH, A3 is CH, A4 is CH, and R5b, n and R2 are as defined in Table P.

Table 71

Table 71 provides 720 compounds of formula IA wherein R1 is methyl-, R3 is dichloromethyl-, R4 is 3,4,5-trichlorophenyl-, Y1-Y2-Y3 is —C=N—CH2-, A2 is CH, A3 is CH, A4 is CH, and R5b, n and R2 are as defined in Table P.

Table 72

Table 72 provides 720 compounds of formula IA wherein R1 is ethyl-, R3 is dichloromethyl-, R4 is 3,4,5-trichlorophenyl-, Y1-Y2-Y3 is —C=N—CH2-, A2 is CH, A3 is CH, A4 is CH, and R5b, n and R2 are as defined in Table P.

Table 73

Table 73 provides 720 compounds of formula IA wherein R1 is hydrogen, R3 is trifluoromethyl-, R4 is 3-chloro-5-fluorophenyl-, Y1-Y2-Y3 is —C=N—CH2-, A2 is CH, A3 is CH, A4 is CH, and R5b, n and R2 are as defined in Table P.

Table 74

Table 74 provides 720 compounds of formula IA wherein R1 is methyl-, R3 is trifluoromethyl-, R4 is 3-chloro-5- fluorophenyl-, Y1-Y2-Y3 is —C=N—CH2-, A2 is CH, A3 is CH, A4 is CH, and R5b, n and R2 are as defined in Table P.

Table 75

Table 75 provides 720 compounds of formula IA wherein R1 is ethyl-, R3 is trifluoromethyl-, R4 is 3-chloro-5-fluorophenyl-, Y1-Y2-Y3 is —C=N—CH2-, A2 is CH, A3 is CH, A4 is CH, and R5b, n and R2 are as defined in Table P.

Table 76

Table 76 provides 720 compounds of formula IA wherein R1 is hydrogen, R3 is dichloromethyl-, R4 is 3-chloro-5-fluorophenyl-, Y1-Y2-Y3 is —C=N—CH2-, A2 is CH, A3 is CH, A4 is CH, and R5b, n and R2 are as defined in Table P.

Table 77

Table 77 provides 720 compounds of formula IA wherein R1 is methyl-, R3 is dichloromethyl-, R4 is 3-chloro-5-fluorophenyl-, Y1-Y2-Y3 is —C=N—CH2-, A2 is CH, A3 is CH, A4 is CH, and R5b, n and R2 are as defined in Table P.

Table 78

Table 78 provides 720 compounds of formula IA wherein R1 is ethyl-, R3 is dichloromethyl-, R4 is 3-chloro-5-fluorophenyl-, Y1-Y2-Y3 is —C=N—CH2-, A2 is CH, A3 is CH, A4 is CH, and R5b, n and R2 are as defined in Table P.

Table 79

Table 79 provides 720 compounds of formula IA wherein R1 is hydrogen, R3 is trifluoromethyl-, R4 is 3-chloro-5-(trifluoromethyl)phenyl-, Y1-Y2-Y3 is —C=N—CH2-, A2 is CH, A3 is CH, A4 is CH, and R5b, n and R2 are as defined in Table P.

Table 80

Table 80 provides 720 compounds of formula IA wherein R1 is methyl-, R3 is trifluoromethyl-, R4 is 3-chloro-5-(trifluoromethyl)phenyl-, Y1-Y2-Y3 is —C=N—CH2-, A2 is CH, A3 is CH, A4 is CH, and R5b, n and R2 are as defined in Table P.

Table 81

Table 81 provides 720 compounds of formula IA wherein R1 is ethyl-, R3 is trifluoromethyl-, R4 is 3-chloro-5-(trifluoromethyl)phenyl-, Y1-Y2-Y3 is —C=N—CH2-, A2 is CH, A3 is CH, A4 is CH, and R5b, n and R2 are as defined in Table P.

Table 82

Table 82 provides 720 compounds of formula IA wherein R1 is hydrogen, R3 is dichloromethyl-, R4 is 3-chloro-5-(trifluoromethyl)phenyl-, Y1-Y2-Y3 is —C=N—CH2-, A2 is CH, A3 is CH, A4 is CH, and R5b, n and R2 are as defined in Table P.

Table 83

Table 83 provides 720 compounds of formula IA wherein R1 is methyl-, R3 is dichloromethyl-, R4 is 3-chloro-5-(trifluoromethyl)phenyl-, Y1-Y2-Y3 is —C=N—CH2-, A2 is CH, A3 is CH, A4 is CH, and R5b, n and R2 are as defined in Table P.

Table 84

Table 84 provides 720 compounds of formula IA wherein R1 is ethyl-, R3 is dichloromethyl-, R4 is 3-chloro-5-(trifluoromethyl)phenyl-, Y1-Y2-Y3 is —C=N—CH2-, A2 is CH, A3 is CH, A4 is CH, and R5b, n and R2 are as defined in Table P.

Table 85

Table 85 provides 720 compounds of formula IA wherein R1 is hydrogen, R3 is trifluoromethyl-, R4 is 3,5-bis(trifluoromethyl)phenyl-, Y1-Y2-Y3 is —C=N—CH2-, A2 is CH, A3 is CH, A4 is CH, and R5b, n and R2 are as defined in Table P.

Table 86

Table 86 provides 720 compounds of formula IA wherein R1 is methyl-, R3 is trifluoromethyl-, R4 is 3,5-bis(trifluoromethyl)phenyl-, Y1-Y2-Y3 is —C=N—CH2-, A2 is CH, A3 is CH, A4 is CH, and R5b, n and R2 are as defined in Table P.

Table 87

Table 87 provides 720 compounds of formula IA wherein R1 is ethyl-, R3 is trifluoromethyl-, R4 is 3,5-bis(trifluoromethyl)phenyl-, Y1-Y2-Y3 is —C=N—CH2-, A2 is CH, A3 is CH, A4 is CH, and R5b, n and R2 are as defined in Table P.

Table 88

Table 88 provides 720 compounds of formula IA wherein R1 is hydrogen, R3 is dichloromethyl-, R4 is 3,5-bis(trifluoromethyl)phenyl-, Y1-Y2-Y3 is —C=N—CH2-, A2 is CH, A3 is CH, A4 is CH, and R5b, n and R2 are as defined in Table P.

Table 89

Table 89 provides 720 compounds of formula IA wherein R1 is methyl-, R3 is dichloromethyl-, R4 is 3,5-bis(trifluoromethyl)phenyl-, Y1-Y2-Y3 is —C=N—CH2-, A2 is CH, A3 is CH, A4 is CH, and R5b, n and R2 are as defined in Table P.

Table 90

Table 90 provides 720 compounds of formula IA wherein R1 is ethyl-, R3 is dichloromethyl-, R4 is 3,5-bis(trifluoromethyl)phenyl-, Y1-Y2-Y3 is —C=N—CH2-, A2 is CH, A3 is CH, A4 is CH, and R5b, n and R2 are as defined in Table P.

Table 91

Table 91 provides 720 compounds of formula IA wherein R1 is hydrogen, R3 is trifluoromethyl-, R4 is 3-(trifluoromethyl)phenyl-, Y1-Y2-Y3 is —C=N—CH2-, A2 is CH, A3 is CH, A4 is CH, and R5b, n and R2 are as defined in Table P.

Table 92

Table 92 provides 720 compounds of formula IA wherein R1 is methyl-, R3 is trifluoromethyl-, R4 is 3-(trifluoromethyl)phenyl-, Y1-Y2-Y3 is —C=N—CH2-, A2 is CH, A3 is CH, A4 is CH, and R5b, n and R2 are as defined in Table P.

Table 93

Table 93 provides 720 compounds of formula IA wherein R1 is ethyl-, R3 is trifluoromethyl-, R4 is 3-(trifluoromethyl)phenyl-, Y1-Y2-Y3 is —C=N—CH2-, A2 is CH, A3 is CH, A4 is CH, and R5b, n and R2 are as defined in Table P.

Table 94

Table 94 provides 720 compounds of formula IA wherein R1 is hydrogen, R3 is dichloromethyl-, R4 is 3-(trifluoromethyl)phenyl-, Y1-Y2-Y3 is —C=N—CH2-, A2 is CH, A3 is CH, A4 is CH, and R5b, n and R2 are as defined in Table P.

Table 95

Table 95 provides 720 compounds of formula IA wherein R1 is methyl-, R3 is dichloromethyl-, R4 is 3-(trifluoromethyl)phenyl-, Y1-Y2-Y3 is —C=N—CH2-, A2 is CH, A3 is CH, A4 is CH, and R5b, n and R2 are as defined in Table P.

Table 96

Table 96 provides 720 compounds of formula IA wherein R1 is ethyl-, R3 is dichloromethyl-, R4 is 3-(trifluoromethyl)

phenyl-, Y1-Y2-Y3 is —C=N—CH2-, A2 is CH, A3 is CH, A4 is CH, and R5b, n and R2 are as defined in Table P.

Table 97

Table 97 provides 720 compounds of formula IA wherein R1 is hydrogen, R3 is trifluoromethyl-, R4 is 3,5-dichlorophenyl-, Y1-Y2-Y3 is —N—CH2-CH2-, A2 is CH, A3 is CH, A4 is CH, and R5b, n and R2 are as defined in Table P.

Table 98

Table 98 provides 720 compounds of formula IA wherein R1 is methyl-, R3 is trifluoromethyl-, R4 is 3,5-dichlorophenyl-, Y1-Y2-Y3 is —N—CH2-CH2-, A2 is CH, A3 is CH, A4 is CH, and R5b, n and R2 are as defined in Table P.

Table 99

Table 99 provides 720 compounds of formula IA wherein R1 is ethyl-, R3 is trifluoromethyl-, R4 is 3,5-dichlorophenyl-, Y1-Y2-Y3 is —N—CH2-CH2-, A2 is CH, A3 is CH, A4 is CH, and R5b, n and R2 are as defined in Table P.

Table 100

Table 100 provides 720 compounds of formula IA wherein R1 is hydrogen, R3 is dichloromethyl-, R4 is 3,5-dichlorophenyl-, Y1-Y2-Y3 is —N—CH2-CH2-, A2 is CH, A3 is CH, A4 is CH, and R5b, n and R2 are as defined in Table P.

Table 101

Table 101 provides 720 compounds of formula IA wherein R1 is methyl-, R3 is dichloromethyl-, R4 is 3,5-dichlorophenyl-, Y1-Y2-Y3 is —N—CH2-CH2-, A2 is CH, A3 is CH, A4 is CH, and R5b, n and R2 are as defined in Table P.

Table 102

Table 102 provides 720 compounds of formula IA wherein R1 is ethyl-, R3 is dichloromethyl-, R4 is 3,5-dichlorophenyl-, Y1-Y2-Y3 is —N—CH2-CH2-, A2 is CH, A3 is CH, A4 is CH, and R5b, n and R2 are as defined in Table P.

Table 103

Table 103 provides 720 compounds of formula IA wherein R1 is hydrogen, R3 is trifluoromethyl-, R4 is 3,4-dichlorophenyl-, Y1-Y2-Y3 is —N—CH2-CH2-, A2 is CH, A3 is CH, A4 is CH, and R5b, n and R2 are as defined in Table P.

Table 104

Table 104 provides 720 compounds of formula IA wherein R1 is methyl-, R3 is trifluoromethyl-, R4 is 3,4-dichlorophenyl-, Y1-Y2-Y3 is —N—CH2-CH2-, A2 is CH, A3 is CH, A4 is CH, and R5b, n and R2 are as defined in Table P.

Table 105

Table 105 provides 720 compounds of formula IA wherein R1 is ethyl-, R3 is trifluoromethyl-, R4 is 3,4-dichlorophenyl-, Y1-Y2-Y3 is —N—CH2-CH2-, A2 is CH, A3 is CH, A4 is CH, and R5b, n and R2 are as defined in Table P.

Table 106

Table 106 provides 720 compounds of formula IA wherein R1 is hydrogen, R3 is dichloromethyl-, R4 is 3,4-dichlorophenyl-, Y1-Y2-Y3 is —N—CH2-CH2-, A2 is CH, A3 is CH, A4 is CH, and R5b, n and R2 are as defined in Table P.

Table 107

Table 107 provides 720 compounds of formula IA wherein R1 is methyl-, R3 is dichloromethyl-, R4 is 3,4-dichlorophenyl-, Y1-Y2-Y3 is —N—CH2-CH2-, A2 is CH, A3 is CH, A4 is CH, and R5b, n and R2 are as defined in Table P.

Table 108

Table 108 provides 720 compounds of formula IA wherein R1 is ethyl-, R3 is dichloromethyl-, R4 is 3,4-dichlorophenyl-, Y1-Y2-Y3 is —N—CH2-CH2-, A2 is CH, A3 is CH, A4 is CH, and R5b, n and R2 are as defined in Table P.

Table 109

Table 109 provides 720 compounds of formula IA wherein R1 is hydrogen, R3 is trifluoromethyl-, R4 is 3,5-dichloro-4-fluorophenyl-, Y1-Y2-Y3 is —N—CH2-CH2-, A2 is CH, A3 is CH, A4 is CH, and R5b, n and R2 are as defined in Table P.

Table 110

Table 110 provides 720 compounds of formula IA wherein R1 is methyl-, R3 is trifluoromethyl-, R4 is 3,5-dichloro-4-fluorophenyl-, Y1-Y2-Y3 is —N—CH2-CH2-, A2 is CH, A3 is CH, A4 is CH, and R5b, n and R2 are as defined in Table P.

Table 111

Table 111 provides 720 compounds of formula IA wherein R1 is ethyl-, R3 is trifluoromethyl-, R4 is 3,5-dichloro-4-fluorophenyl-, Y1-Y2-Y3 is —N—CH2-CH2-, A2 is CH, A3 is CH, A4 is CH, and R5b, n and R2 are as defined in Table P.

Table 112

Table 112 provides 720 compounds of formula IA wherein R1 is hydrogen, R3 is dichloromethyl-, R4 is 3,5-dichloro-4-fluorophenyl-, Y1-Y2-Y3 is —N—CH2-CH2-, A2 is CH, A3 is CH, A4 is CH, and R5b, n and R2 are as defined in Table P.

Table 113

Table 113 provides 720 compounds of formula IA wherein R1 is methyl-, R3 is dichloromethyl-, R4 is 3,5-dichloro-4-fluorophenyl-, Y1-Y2-Y3 is —N—CH2-CH2-, A2 is CH, A3 is CH, A4 is CH, and R5b, n and R2 are as defined in Table P.

Table 114

Table 114 provides 720 compounds of formula IA wherein R1 is ethyl-, R3 is dichloromethyl-, R4 is 3,5-dichloro-4-fluorophenyl-, Y1-Y2-Y3 is —N—CH2-CH2-, A2 is CH, A3 is CH, A4 is CH, and R5b, n and R2 are as defined in Table P.

Table 115

Table 115 provides 720 compounds of formula IA wherein R1 is hydrogen, R3 is trifluoromethyl-, R4 is 3,4,5-trichlorophenyl-, Y1-Y2-Y3 is —N—CH2-CH2-, A2 is CH, A3 is CH, A4 is CH, and R5b, n and R2 are as defined in Table P.

Table 116

Table 116 provides 720 compounds of formula IA wherein R1 is methyl-, R3 is trifluoromethyl-, R4 is 3,4,5-trichlorophenyl-, Y1-Y2-Y3 is —N—CH2-CH2-, A2 is CH, A3 is CH, A4 is CH, and R5b, n and R2 are as defined in Table P.

Table 117

Table 117 provides 720 compounds of formula IA wherein R1 is ethyl-, R3 is trifluoromethyl-, R4 is 3,4,5-trichlorophenyl-, Y1-Y2-Y3 is —N—CH2-CH2-, A2 is CH, A3 is CH, A4 is CH, and R5b, n and R2 are as defined in Table P.

Table 118

Table 118 provides 720 compounds of formula IA wherein R1 is hydrogen, R3 is dichloromethyl-, R4 is 3,4,5-trichlorophenyl-, Y1-Y2-Y3 is —N—CH2-CH2-, A2 is CH, A3 is CH, A4 is CH, and R5b, n and R2 are as defined in Table P.

Table 119

Table 119 provides 720 compounds of formula IA wherein R1 is methyl-, R3 is dichloromethyl-, R4 is 3,4,5-trichlorophenyl-, Y1-Y2-Y3 is —N—CH2-CH2-, A2 is CH, A3 is CH, A4 is CH, and R5b, n and R2 are as defined in Table P.

Table 120

Table 120 provides 720 compounds of formula IA wherein R1 is ethyl-, R3 is dichloromethyl-, R4 is 3,4,5-trichlorophenyl-, Y1-Y2-Y3 is —N—CH2-CH2-, A2 is CH, A3 is CH, A4 is CH, and R5b, n and R2 are as defined in Table P.

Table 121

Table 121 provides 720 compounds of formula IA wherein R1 is hydrogen, R3 is trifluoromethyl-, R4 is 3-chloro-5-fluorophenyl-, Y1-Y2-Y3 is —N—CH2-CH2-, A2 is CH, A3 is CH, A4 is CH, and R5b, n and R2 are as defined in Table P.

Table 122

Table 122 provides 720 compounds of formula IA wherein R1 is methyl-, R3 is trifluoromethyl-, R4 is 3-chloro-5-fluorophenyl-, Y1-Y2-Y3 is —N—CH2-CH2-, A2 is CH, A3 is CH, A4 is CH, and R5b, n and R2 are as defined in Table P.

Table 123

Table 123 provides 720 compounds of formula IA wherein R1 is ethyl-, R3 is trifluoromethyl-, R4 is 3-chloro-5-fluorophenyl-, Y1-Y2-Y3 is —N—CH2-CH2-, A2 is CH, A3 is CH, A4 is CH, and R5b, n and R2 are as defined in Table P.

Table 124

Table 124 provides 720 compounds of formula IA wherein R1 is hydrogen, R3 is dichloromethyl-, R4 is 3-chloro-5-fluorophenyl-, Y1-Y2-Y3 is —N—CH2-CH2-, A2 is CH, A3 is CH, A4 is CH, and R5b, n and R2 are as defined in Table P.

Table 125

Table 125 provides 720 compounds of formula IA wherein R1 is methyl-, R3 is dichloromethyl-, R4 is 3-chloro-5-fluorophenyl-, Y1-Y2-Y3 is —N—CH2-CH2-, A2 is CH, A3 is CH, A4 is CH, and R5b, n and R2 are as defined in Table P.

Table 126

Table 126 provides 720 compounds of formula IA wherein R1 is ethyl-, R3 is dichloromethyl-, R4 is 3-chloro-5-fluorophenyl-, Y1-Y2-Y3 is —N—CH2-CH2-, A2 is CH, A3 is CH, A4 is CH, and R5b, n and R2 are as defined in Table P.

Table 127

Table 127 provides 720 compounds of formula IA wherein R1 is hydrogen, R3 is trifluoromethyl-, R4 is 3-chloro-5-(trifluoromethyl)phenyl-, Y1-Y2-Y3 is —N—CH2-CH2-, A2 is CH, A3 is CH, A4 is CH, and R5b, n and R2 are as defined in Table P.

Table 128

Table 128 provides 720 compounds of formula IA wherein R1 is methyl-, R3 is trifluoromethyl-, R4 is 3-chloro-5-(trifluoromethyl)phenyl-, Y1-Y2-Y3 is —N—CH2-CH2-, A2 is CH, A3 is CH, A4 is CH, and R5b, n and R2 are as defined in Table P.

Table 129

Table 129 provides 720 compounds of formula IA wherein R1 is ethyl-, R3 is trifluoromethyl-, R4 is 3-chloro-5-(trifluoromethyl)phenyl-, Y1-Y2-Y3 is —N—CH2-CH2-, A2 is CH, A3 is CH, A4 is CH, and R5b, n and R2 are as defined in Table P.

Table 130

Table 130 provides 720 compounds of formula IA wherein R1 is hydrogen, R3 is dichloromethyl-, R4 is 3-chloro-5-(trifluoromethyl)phenyl-, Y1-Y2-Y3 is —N—CH2-CH2-, A2 is CH, A3 is CH, A4 is CH, and R5b, n and R2 are as defined in Table P.

Table 131

Table 131 provides 720 compounds of formula IA wherein R1 is methyl-, R3 is dichloromethyl-, R4 is 3-chloro-5-(trifluoromethyl)phenyl-, Y1-Y2-Y3 is —N—CH2-CH2-, A2 is CH, A3 is CH, A4 is CH, and R5b, n and R2 are as defined in Table P.

Table 132

Table 132 provides 720 compounds of formula IA wherein R1 is ethyl-, R3 is dichloromethyl-, R4 is 3-chloro-5-(trifluoromethyl)phenyl-, Y1-Y2-Y3 is —N—CH2-CH2-, A2 is CH, A3 is CH, A4 is CH, and R5b, n and R2 are as defined in Table P.

Table 133

Table 133 provides 720 compounds of formula IA wherein R1 is hydrogen, R3 is trifluoromethyl-, R4 is 3,5-bis(trifluoromethyl)phenyl-, Y1-Y2-Y3 is —N—CH2-CH2-, A2 is CH, A3 is CH, A4 is CH, and R5b, n and R2 are as defined in Table P.

Table 134

Table 134 provides 720 compounds of formula IA wherein R1 is methyl-, R3 is trifluoromethyl-, R4 is 3,5-bis(trifluoromethyl)phenyl-, Y1-Y2-Y3 is —N—CH2-CH2-, A2 is CH, A3 is CH, A4 is CH, and R5b, n and R2 are as defined in Table P.

Table 135

Table 135 provides 720 compounds of formula IA wherein R1 is ethyl-, R3 is trifluoromethyl-, R4 is 3,5-bis(trifluoromethyl)phenyl-, Y1-Y2-Y3 is —N—CH2-CH2-, A2 is CH, A3 is CH, A4 is CH, and R5b, n and R2 are as defined in Table P.

Table 136

Table 136 provides 720 compounds of formula IA wherein R1 is hydrogen, R3 is dichloromethyl-, R4 is 3,5-bis(trifluoromethyl)phenyl-, Y1-Y2-Y3 is —N—CH2-CH2-, A2 is CH, A3 is CH, A4 is CH, and R5b, n and R2 are as defined in Table P.

Table 137

Table 137 provides 720 compounds of formula IA wherein R1 is methyl-, R3 is dichloromethyl-, R4 is 3,5-bis(trifluoromethyl)phenyl-, Y1-Y2-Y3 is —N—CH2-CH2-, A2 is CH, A3 is CH, A4 is CH, and R5b, n and R2 are as defined in Table P.

Table 138

Table 138 provides 720 compounds of formula IA wherein R1 is ethyl-, R3 is dichloromethyl-, R4 is 3,5-bis(trifluoromethyl)phenyl-, Y1-Y2-Y3 is —N—CH2-CH2-, A2 is CH, A3 is CH, A4 is CH, and R5b, n and R2 are as defined in Table P.

Table 139

Table 139 provides 720 compounds of formula IA wherein R1 is hydrogen, R3 is trifluoromethyl-, R4 is 3-(trifluoromethyl)phenyl-, Y1-Y2-Y3 is —N—CH2-CH2-, A2 is CH, A3 is CH, A4 is CH, and R5b, n and R2 are as defined in Table P.

Table 140

Table 140 provides 720 compounds of formula IA wherein R1 is methyl-, R3 is trifluoromethyl-, R4 is 3-(trifluoromethyl)phenyl-, Y1-Y2-Y3 is —N—CH2-CH2-, A2 is CH, A3 is CH, A4 is CH, and R5b, n and R2 are as defined in Table P.

Table 141

Table 141 provides 720 compounds of formula IA wherein R1 is ethyl-, R3 is trifluoromethyl-, R4 is 3-(trifluoromethyl)phenyl-, Y1-Y2-Y3 is —N—CH2-CH2-, A2 is CH, A3 is CH, A4 is CH, and R5b, n and R2 are as defined in Table P.

Table 142

Table 142 provides 720 compounds of formula IA wherein R1 is hydrogen, R3 is dichloromethyl-, R4 is 3-(trifluoromethyl)phenyl-, Y1-Y2-Y3 is —N—CH2-CH2-, A2 is CH, A3 is CH, A4 is CH, and R5b, n and R2 are as defined in Table P.

Table 143

Table 143 provides 720 compounds of formula IA wherein R1 is methyl-, R3 is dichloromethyl-, R4 is 3-(trifluoromethyl)phenyl-, Y1-Y2-Y3 is —N—CH2-CH2-, A2 is CH, A3 is CH, A4 is CH, and R5b, n and R2 are as defined in Table P.

Table 144

Table 144 provides 720 compounds of formula IA wherein R1 is ethyl-, R3 is dichloromethyl-, R4 is 3-(trifluoromethyl)phenyl-, Y1-Y2-Y3 is —N—CH2-CH2-, A2 is CH, A3 is CH, A4 is CH, and R5b, n and R2 are as defined in Table P.

Table 145

Table 145 provides 720 compounds of formula IA wherein R1 is hydrogen, R3 is trifluoromethyl-, R4 is 3,5-dichlorophenyl-, Y1-Y2-Y3 is —C═CH—O—, A2 is CH, A3 is CH, A4 is CH, and R5b, n and R2 are as defined in Table P.

Table 146

Table 146 provides 720 compounds of formula IA wherein R1 is methyl-, R3 is trifluoromethyl-, R4 is 3,5-dichlorophenyl-, Y1-Y2-Y3 is —C═CH—O—, A2 is CH, A3 is CH, A4 is CH, and R5b, n and R2 are as defined in Table P.

Table 147

Table 147 provides 720 compounds of formula IA wherein R1 is ethyl-, R3 is trifluoromethyl-, R4 is 3,5-dichlorophenyl-, Y1-Y2-Y3 is —C═CH—O—, A2 is CH, A3 is CH, A4 is CH, and R5b, n and R2 are as defined in Table P.

Table 148

Table 148 provides 720 compounds of formula IA wherein R1 is hydrogen, R3 is dichloromethyl-, R4 is 3,5-dichlorophenyl-, Y1-Y2-Y3 is —C═CH—O—, A2 is CH, A3 is CH, A4 is CH, and R5b, n and R2 are as defined in Table P.

Table 149

Table 149 provides 720 compounds of formula IA wherein R1 is methyl-, R3 is dichloromethyl-, R4 is 3,5-dichlorophenyl-, Y1-Y2-Y3 is —C═CH—O—, A2 is CH, A3 is CH, A4 is CH, and R5b, n and R2 are as defined in Table P.

Table 150

Table 150 provides 720 compounds of formula IA wherein R1 is ethyl-, R3 is dichloromethyl-, R4 is 3,5-dichlorophenyl-, Y1-Y2-Y3 is —C═CH—O—, A2 is CH, A3 is CH, A4 is CH, and R5b, n and R2 are as defined in Table P.

Table 151

Table 151 provides 720 compounds of formula IA wherein R1 is hydrogen, R3 is trifluoromethyl-, R4 is 3,4-dichlorophenyl-, Y1-Y2-Y3 is —C═CH—O—, A2 is CH, A3 is CH, A4 is CH, and R5b, n and R2 are as defined in Table P.

Table 152

Table 152 provides 720 compounds of formula IA wherein R1 is methyl-, R3 is trifluoromethyl-, R4 is 3,4-dichlorophenyl-, Y1-Y2-Y3 is —C═CH—O—, A2 is CH, A3 is CH, A4 is CH, and R5b, n and R2 are as defined in Table P.

Table 153

Table 153 provides 720 compounds of formula IA wherein R1 is ethyl-, R3 is trifluoromethyl-, R4 is 3,4-dichlorophenyl-, Y1-Y2-Y3 is —C═CH—O—, A2 is CH, A3 is CH, A4 is CH, and R5b, n and R2 are as defined in Table P.

Table 154

Table 154 provides 720 compounds of formula IA wherein R1 is hydrogen, R3 is dichloromethyl-, R4 is 3,4-dichlorophenyl-, Y1-Y2-Y3 is —C═CH—O—, A2 is CH, A3 is CH, A4 is CH, and R5b, n and R2 are as defined in Table P.

Table 155

Table 155 provides 720 compounds of formula IA wherein R1 is methyl-, R3 is dichloromethyl-, R4 is 3,4-dichlorophenyl-, Y1-Y2-Y3 is —C═CH—O—, A2 is CH, A3 is CH, A4 is CH, and R5b, n and R2 are as defined in Table P.

Table 156

Table 156 provides 720 compounds of formula IA wherein R1 is ethyl-, R3 is dichloromethyl-, R4 is 3,4-dichlorophenyl-, Y1-Y2-Y3 is —C═CH—O—, A2 is CH, A3 is CH, A4 is CH, and R5b, n and R2 are as defined in Table P.

Table 157

Table 157 provides 720 compounds of formula IA wherein R1 is hydrogen, R3 is trifluoromethyl-, R4 is 3,5-dichloro-4-fluorophenyl-, Y1-Y2-Y3 is —C═CH—O—, A2 is CH, A3 is CH, A4 is CH, and R5b, n and R2 are as defined in Table P.

Table 158

Table 158 provides 720 compounds of formula IA wherein R1 is methyl-, R3 is trifluoromethyl-, R4 is 3,5-dichloro-4-fluorophenyl-, Y1-Y2-Y3 is —C═CH—O—, A2 is CH, A3 is CH, A4 is CH, and R5b, n and R2 are as defined in Table P.

Table 159

Table 159 provides 720 compounds of formula IA wherein R1 is ethyl-, R3 is trifluoromethyl-, R4 is 3,5-dichloro-4-fluorophenyl-, Y1-Y2-Y3 is —C═CH—O—, A2 is CH, A3 is CH, A4 is CH, and R5b, n and R2 are as defined in Table P.

Table 160

Table 160 provides 720 compounds of formula IA wherein R1 is hydrogen, R3 is dichloromethyl-, R4 is 3,5-dichloro-4-fluorophenyl-, Y1-Y2-Y3 is —C═CH—O—, A2 is CH, A3 is CH, A4 is CH, and R5b, n and R2 are as defined in Table P.

Table 161

Table 161 provides 720 compounds of formula IA wherein R1 is methyl-, R3 is dichloromethyl-, R4 is 3,5-dichloro-4-fluorophenyl-, Y1-Y2-Y3 is —C═CH—O—, A2 is CH, A3 is CH, A4 is CH, and R5b, n and R2 are as defined in Table P.

Table 162

Table 162 provides 720 compounds of formula IA wherein R1 is ethyl-, R3 is dichloromethyl-, R4 is 3,5-dichloro-4-fluorophenyl-, Y1-Y2-Y3 is —C═CH—O—, A2 is CH, A3 is CH, A4 is CH, and R5b, n and R2 are as defined in Table P.

Table 163

Table 163 provides 720 compounds of formula IA wherein R1 is hydrogen, R3 is trifluoromethyl-, R4 is 3,4,5-trichlorophenyl-, Y1-Y2-Y3 is —C═CH—O—, A2 is CH, A3 is CH, A4 is CH, and R5b, n and R2 are as defined in Table P.

Table 164

Table 164 provides 720 compounds of formula IA wherein R1 is methyl-, R3 is trifluoromethyl-, R4 is 3,4,5-trichlorophenyl-, Y1-Y2-Y3 is —C═CH—O—, A2 is CH, A3 is CH, A4 is CH, and R5b, n and R2 are as defined in Table P.

Table 165

Table 165 provides 720 compounds of formula IA wherein R1 is ethyl-, R3 is trifluoromethyl-, R4 is 3,4,5-trichlorophenyl-, Y1-Y2-Y3 is —C═CH—O—, A2 is CH, A3 is CH, A4 is CH, and R5b, n and R2 are as defined in Table P.

Table 166

Table 166 provides 720 compounds of formula IA wherein R1 is hydrogen, R3 is dichloromethyl-, R4 is 3,4,5-trichlorophenyl-, Y1-Y2-Y3 is —C═CH—O—, A2 is CH, A3 is CH, A4 is CH, and R5b, n and R2 are as defined in Table P.

Table 167

Table 167 provides 720 compounds of formula IA wherein R1 is methyl-, R3 is dichloromethyl-, R4 is 3,4,5-trichlorophenyl-, Y1-Y2-Y3 is —C═CH—O—, A2 is CH, A3 is CH, A4 is CH, and R5b, n and R2 are as defined in Table P.

Table 168

Table 168 provides 720 compounds of formula IA wherein R1 is ethyl-, R3 is dichloromethyl-, R4 is 3,4,5-trichlorophenyl-, Y1-Y2-Y3 is —C═CH—O—, A2 is CH, A3 is CH, A4 is CH, and R5b, n and R2 are as defined in Table P.

Table 169

Table 169 provides 720 compounds of formula IA wherein R1 is hydrogen, R3 is trifluoromethyl-, R4 is 3-chloro-5-fluorophenyl-, Y1-Y2-Y3 is —C═CH—O—, A2 is CH, A3 is CH, A4 is CH, and R5b, n and R2 are as defined in Table P.

Table 170

Table 170 provides 720 compounds of formula IA wherein R1 is methyl-, R3 is trifluoromethyl-, R4 is 3-chloro-5-fluorophenyl-, Y1-Y2-Y3 is —C═CH—O—, A2 is CH, A3 is CH, A4 is CH, and R5b, n and R2 are as defined in Table P.

Table 171

Table 171 provides 720 compounds of formula IA wherein R1 is ethyl-, R3 is trifluoromethyl-, R4 is 3-chloro-5-fluorophenyl-, Y1-Y2-Y3 is —C═CH—O—, A2 is CH, A3 is CH, A4 is CH, and R5b, n and R2 are as defined in Table P.

Table 172

Table 172 provides 720 compounds of formula IA wherein R1 is hydrogen, R3 is dichloromethyl-, R4 is 3-chloro-5-fluorophenyl-, Y1-Y2-Y3 is —C═CH—O—, A2 is CH, A3 is CH, A4 is CH, and R5b, n and R2 are as defined in Table P.

Table 173

Table 173 provides 720 compounds of formula IA wherein R1 is methyl-, R3 is dichloromethyl-, R4 is 3-chloro-5-fluorophenyl-, Y1-Y2-Y3 is —C═CH—O—, A2 is CH, A3 is CH, A4 is CH, and R5b, n and R2 are as defined in Table P.

Table 174

Table 174 provides 720 compounds of formula IA wherein R1 is ethyl-, R3 is dichloromethyl-, R4 is 3-chloro-5-fluorophenyl-, Y1-Y2-Y3 is —C═CH—O—, A2 is CH, A3 is CH, A4 is CH, and R5b, n and R2 are as defined in Table P.

Table 175

Table 175 provides 720 compounds of formula IA wherein R1 is hydrogen, R3 is trifluoromethyl-, R4 is 3-chloro-5-(trifluoromethyl)phenyl-, Y1-Y2-Y3 is —C═CH—O—, A2 is CH, A3 is CH, A4 is CH, and R5b, n and R2 are as defined in Table P.

Table 176

Table 176 provides 720 compounds of formula IA wherein R1 is methyl-, R3 is trifluoromethyl-, R4 is 3-chloro-5-(trifluoromethyl)phenyl-, Y1-Y2-Y3 is —C═CH—O—, A2 is CH, A3 is CH, A4 is CH, and R5b, n and R2 are as defined in Table P.

Table 177

Table 177 provides 720 compounds of formula IA wherein R1 is ethyl-, R3 is trifluoromethyl-, R4 is 3-chloro-5-(trifluoromethyl)phenyl-, Y1-Y2-Y3 is —C═CH—O—, A2 is CH, A3 is CH, A4 is CH, and R5b, n and R2 are as defined in Table P.

Table 178

Table 178 provides 720 compounds of formula IA wherein R1 is hydrogen, R3 is dichloromethyl-, R4 is 3-chloro-5-(trifluoromethyl)phenyl-, Y1-Y2-Y3 is —C═CH—O—, A2 is CH, A3 is CH, A4 is CH, and R5b, n and R2 are as defined in Table P.

Table 179

Table 179 provides 720 compounds of formula IA wherein R1 is methyl-, R3 is dichloromethyl-, R4 is 3-chloro-5-(trifluoromethyl)phenyl-, Y1-Y2-Y3 is —C═CH—O—, A2 is CH, A3 is CH, A4 is CH, and R5b, n and R2 are as defined in Table P.

Table 180

Table 180 provides 720 compounds of formula IA wherein R1 is ethyl-, R3 is dichloromethyl-, R4 is 3-chloro-5-(trifluoromethyl)phenyl-, Y1-Y2-Y3 is —C═CH—O—, A2 is CH, A3 is CH, A4 is CH, and R5b, n and R2 are as defined in Table P.

Table 181

Table 181 provides 720 compounds of formula IA wherein R1 is hydrogen, R3 is trifluoromethyl-, R4 is 3,5-bis(trifluoromethyl)phenyl-, Y1-Y2-Y3 is —C═CH—O—, A2 is CH, A3 is CH, A4 is CH, and R5b, n and R2 are as defined in Table P.

Table 182

Table 182 provides 720 compounds of formula IA wherein R1 is methyl-, R3 is trifluoromethyl-, R4 is 3,5-bis(trifluoromethyl)phenyl-, Y1-Y2-Y3 is —C═CH—O—, A2 is CH, A3 is CH, A4 is CH, and R5b, n and R2 are as defined in Table P.

Table 183

Table 183 provides 720 compounds of formula IA wherein R1 is ethyl-, R3 is trifluoromethyl-, R4 is 3,5-bis(trifluoromethyl)phenyl-, Y1-Y2-Y3 is —C═CH—O—, A2 is CH, A3 is CH, A4 is CH, and R5b, n and R2 are as defined in Table P.

Table 184

Table 184 provides 720 compounds of formula IA wherein R1 is hydrogen, R3 is dichloromethyl-, R4 is 3,5-bis(trifluoromethyl)phenyl-, Y1-Y2-Y3 is —C═CH—O—, A2 is CH, A3 is CH, A4 is CH, and R5b, n and R2 are as defined in Table P.

Table 185

Table 185 provides 720 compounds of formula IA wherein R1 is methyl-, R3 is dichloromethyl-, R4 is 3,5-bis(trifluoromethyl)phenyl-, Y1-Y2-Y3 is —C=CH—O—, A2 is CH, A3 is CH, A4 is CH, and R5b, n and R2 are as defined in Table P.

Table 186

Table 186 provides 720 compounds of formula IA wherein R1 is ethyl-, R3 is dichloromethyl-, R4 is 3,5-bis(trifluoromethyl)phenyl-, Y1-Y2-Y3 is —C=CH—O—, A2 is CH, A3 is CH, A4 is CH, and R5b, n and R2 are as defined in Table P.

Table 187

Table 187 provides 720 compounds of formula IA wherein R1 is hydrogen, R3 is trifluoromethyl-, R4 is 3-(trifluoromethyl)phenyl-, Y1-Y2-Y3 is —C=CH—O—, A2 is CH, A3 is CH, A4 is CH, and R5b, n and R2 are as defined in Table P.

Table 188

Table 188 provides 720 compounds of formula IA wherein R1 is methyl-, R3 is trifluoromethyl-, R4 is 3-(trifluoromethyl)phenyl-, Y1-Y2-Y3 is —C=CH—O—, A2 is CH, A3 is CH, A4 is CH, and R5b, n and R2 are as defined in Table P.

Table 189

Table 189 provides 720 compounds of formula IA wherein R1 is ethyl-, R3 is trifluoromethyl-, R4 is 3-(trifluoromethyl)phenyl-, Y1-Y2-Y3 is —C=CH—O—, A2 is CH, A3 is CH, A4 is CH, and R5b, n and R2 are as defined in Table P.

Table 190

Table 190 provides 720 compounds of formula IA wherein R1 is hydrogen, R3 is dichloromethyl-, R4 is 3-(trifluoromethyl)phenyl-, Y1-Y2-Y3 is —C=CH—O—, A2 is CH, A3 is CH, A4 is CH, and R5b, n and R2 are as defined in Table P.

Table 191

Table 191 provides 720 compounds of formula IA wherein R1 is methyl-, R3 is dichloromethyl-, R4 is 3-(trifluoromethyl)phenyl-, Y1-Y2-Y3 is —C=CH—O—, A2 is CH, A3 is CH, A4 is CH, and R5b, n and R2 are as defined in Table P.

Table 192

Table 192 provides 720 compounds of formula IA wherein R1 is ethyl-, R3 is dichloromethyl-, R4 is 3-(trifluoromethyl)phenyl-, Y1-Y2-Y3 is —C=CH—O—, A2 is CH, A3 is CH, A4 is CH, and R5b, n and R2 are as defined in Table P.

Table 193

Table 193 provides 720 compounds of formula IA wherein R1 is hydrogen, R3 is trifluoromethyl-, R4 is 3,5-dichlorophenyl-, Y1-Y2-Y3 is —C=N—S—, A2 is CH, A3 is CH, A4 is CH, and R5b, n and R2 are as defined in Table P.

Table 194

Table 194 provides 720 compounds of formula IA wherein R1 is methyl-, R3 is trifluoromethyl-, R4 is 3,5-dichlorophenyl-, Y1-Y2-Y3 is —C=N—S—, A2 is CH, A3 is CH, A4 is CH, and R5b, n and R2 are as defined in Table P.

Table 195

Table 195 provides 720 compounds of formula IA wherein R1 is ethyl-, R3 is trifluoromethyl-, R4 is 3,5-dichlorophenyl-, Y1-Y2-Y3 is —C=N—S—, A2 is CH, A3 is CH, A4 is CH, and R5b, n and R2 are as defined in Table P.

Table 196

Table 196 provides 720 compounds of formula IA wherein R1 is hydrogen, R3 is dichloromethyl-, R4 is 3,5-dichlorophenyl-, Y1-Y2-Y3 is —C=N—S—, A2 is CH, A3 is CH, A4 is CH, and R5b, n and R2 are as defined in Table P.

Table 197

Table 197 provides 720 compounds of formula IA wherein R1 is methyl-, R3 is dichloromethyl-, R4 is 3,5-dichlorophenyl-, Y1-Y2-Y3 is —C=N—S—, A2 is CH, A3 is CH, A4 is CH, and R5b, n and R2 are as defined in Table P.

Table 198

Table 198 provides 720 compounds of formula IA wherein R1 is ethyl-, R3 is dichloromethyl-, R4 is 3,5-dichlorophenyl-, Y1-Y2-Y3 is —C=N—S—, A2 is CH, A3 is CH, A4 is CH, and R5b, n and R2 are as defined in Table P.

Table 199

Table 199 provides 720 compounds of formula IA wherein R1 is hydrogen, R3 is trifluoromethyl-, R4 is 3,4-dichlorophenyl-, Y1-Y2-Y3 is —C=N—S—, A2 is CH, A3 is CH, A4 is CH, and R5b, n and R2 are as defined in Table P.

Table 200

Table 200 provides 720 compounds of formula IA wherein R1 is methyl-, R3 is trifluoromethyl-, R4 is 3,4-dichlorophenyl-, Y1-Y2-Y3 is —C=N—S—, A2 is CH, A3 is CH, A4 is CH, and R5b, n and R2 are as defined in Table P.

Table 201

Table 201 provides 720 compounds of formula IA wherein R1 is ethyl-, R3 is trifluoromethyl-, R4 is 3,4-dichlorophenyl-, Y1-Y2-Y3 is —C=N—S—, A2 is CH, A3 is CH, A4 is CH, and R5b, n and R2 are as defined in Table P.

Table 202

Table 202 provides 720 compounds of formula IA wherein R1 is hydrogen, R3 is dichloromethyl-, R4 is 3,4-dichlorophenyl-, Y1-Y2-Y3 is —C=N—S—, A2 is CH, A3 is CH, A4 is CH, and R5b, n and R2 are as defined in Table P.

Table 203

Table 203 provides 720 compounds of formula IA wherein R1 is methyl-, R3 is dichloromethyl-, R4 is 3,4-dichlorophenyl-, Y1-Y2-Y3 is —C=N—S—, A2 is CH, A3 is CH, A4 is CH, and R5b, n and R2 are as defined in Table P.

Table 204

Table 204 provides 720 compounds of formula IA wherein R1 is ethyl-, R3 is dichloromethyl-, R4 is 3,4-dichlorophenyl-, Y1-Y2-Y3 is —C=N—S—, A2 is CH, A3 is CH, A4 is CH, and R5b, n and R2 are as defined in Table P.

Table 205

Table 205 provides 720 compounds of formula IA wherein R1 is hydrogen, R3 is trifluoromethyl-, R4 is 3,5-dichloro-4-fluorophenyl-, Y1-Y2-Y3 is —C=N—S—, A2 is CH, A3 is CH, A4 is CH, and R5b, n and R2 are as defined in Table P.

Table 206

Table 206 provides 720 compounds of formula IA wherein R1 is methyl-, R3 is trifluoromethyl-, R4 is 3,5-dichloro-4-fluorophenyl-, Y1-Y2-Y3 is —C=N—S—, A2 is CH, A3 is CH, A4 is CH, and R5b, n and R2 are as defined in Table P.

Table 207
Table 207 provides 720 compounds of formula IA wherein R1 is ethyl-, R3 is trifluoromethyl-, R4 is 3,5-dichloro-4-fluorophenyl-, Y1-Y2-Y3 is —C═N—S—, A2 is CH, A3 is CH, A4 is CH, and R5b, n and R2 are as defined in Table P.

Table 208
Table 208 provides 720 compounds of formula IA wherein R1 is hydrogen, R3 is dichloromethyl-, R4 is 3,5-dichloro-4-fluorophenyl-, Y1-Y2-Y3 is —C═N—S—, A2 is CH, A3 is CH, A4 is CH, and R5b, n and R2 are as defined in Table P.

Table 209
Table 209 provides 720 compounds of formula IA wherein R1 is methyl-, R3 is dichloromethyl-, R4 is 3,5-dichloro-4-fluorophenyl-, Y1-Y2-Y3 is —C═N—S—, A2 is CH, A3 is CH, A4 is CH, and R5b, n and R2 are as defined in Table P.

Table 210
Table 210 provides 720 compounds of formula IA wherein R1 is ethyl-, R3 is dichloromethyl-, R4 is 3,5-dichloro-4-fluorophenyl-, Y1-Y2-Y3 is —C═N—S—, A2 is CH, A3 is CH, A4 is CH, and R5b, n and R2 are as defined in Table P.

Table 211
Table 211 provides 720 compounds of formula IA wherein R1 is hydrogen, R3 is trifluoromethyl-, R4 is 3,4,5-trichlorophenyl-, Y1-Y2-Y3 is —C═N—S—, A2 is CH, A3 is CH, A4 is CH, and R5b, n and R2 are as defined in Table P.

Table 212
Table 212 provides 720 compounds of formula IA wherein R1 is methyl-, R3 is trifluoromethyl-, R4 is 3,4,5-trichlorophenyl-, Y1-Y2-Y3 is —C═N—S—, A2 is CH, A3 is CH, A4 is CH, and R5b, n and R2 are as defined in Table P.

Table 213
Table 213 provides 720 compounds of formula IA wherein R1 is ethyl-, R3 is trifluoromethyl-, R4 is 3,4,5-trichlorophenyl-, Y1-Y2-Y3 is —C═N—S—, A2 is CH, A3 is CH, A4 is CH, and R5b, n and R2 are as defined in Table P.

Table 214
Table 214 provides 720 compounds of formula IA wherein R1 is hydrogen, R3 is dichloromethyl-, R4 is 3,4,5-trichlorophenyl-, Y1-Y2-Y3 is —C═N—S—, A2 is CH, A3 is CH, A4 is CH, and R5b, n and R2 are as defined in Table P.

Table 215
Table 215 provides 720 compounds of formula IA wherein R1 is methyl-, R3 is dichloromethyl-, R4 is 3,4,5-trichlorophenyl-, Y1-Y2-Y3 is —C═N—S—, A2 is CH, A3 is CH, A4 is CH, and R5b, n and R2 are as defined in Table P.

Table 216
Table 216 provides 720 compounds of formula IA wherein R1 is ethyl-, R3 is dichloromethyl-, R4 is 3,4,5-trichlorophenyl-, Y1-Y2-Y3 is —C═N—S—, A2 is CH, A3 is CH, A4 is CH, and R5b, n and R2 are as defined in Table P.

Table 217
Table 217 provides 720 compounds of formula IA wherein R1 is hydrogen, R3 is trifluoromethyl-, R4 is 3-chloro-5-fluorophenyl-, Y1-Y2-Y3 is —C═N—S—, A2 is CH, A3 is CH, A4 is CH, and R5b, n and R2 are as defined in Table P.

Table 218
Table 218 provides 720 compounds of formula IA wherein R1 is methyl-, R3 is trifluoromethyl-, R4 is 3-chloro-5-fluorophenyl-, Y1-Y2-Y3 is —C═N—S—, A2 is CH, A3 is CH, A4 is CH, and R5b, n and R2 are as defined in Table P.

Table 219
Table 219 provides 720 compounds of formula IA wherein R1 is ethyl-, R3 is trifluoromethyl-, R4 is 3-chloro-5-fluorophenyl-, Y1-Y2-Y3 is —C═N—S—, A2 is CH, A3 is CH, A4 is CH, and R5b, n and R2 are as defined in Table P.

Table 220
Table 220 provides 720 compounds of formula IA wherein R1 is hydrogen, R3 is dichloromethyl-, R4 is 3-chloro-5-fluorophenyl-, Y1-Y2-Y3 is —C═N—S—, A2 is CH, A3 is CH, A4 is CH, and R5b, n and R2 are as defined in Table P.

Table 221
Table 221 provides 720 compounds of formula IA wherein R1 is methyl-, R3 is dichloromethyl-, R4 is 3-chloro-5-fluorophenyl-, Y1-Y2-Y3 is —C═N—S—, A2 is CH, A3 is CH, A4 is CH, and R5b, n and R2 are as defined in Table P.

Table 222
Table 222 provides 720 compounds of formula IA wherein R1 is ethyl-, R3 is dichloromethyl-, R4 is 3-chloro-5-fluorophenyl-, Y1-Y2-Y3 is —C═N—S—, A2 is CH, A3 is CH, A4 is CH, and R5b, n and R2 are as defined in Table P.

Table 223
Table 223 provides 720 compounds of formula IA wherein R1 is hydrogen, R3 is trifluoromethyl-, R4 is 3-chloro-5-(trifluoromethyl)phenyl-, Y1-Y2-Y3 is —C═N—S—, A2 is CH, A3 is CH, A4 is CH, and R5b, n and R2 are as defined in Table P.

Table 224
Table 224 provides 720 compounds of formula IA wherein R1 is methyl-, R3 is trifluoromethyl-, R4 is 3-chloro-5-(trifluoromethyl)phenyl-, Y1-Y2-Y3 is —C═N—S—, A2 is CH, A3 is CH, A4 is CH, and R5b, n and R2 are as defined in Table P.

Table 225
Table 225 provides 720 compounds of formula IA wherein R1 is ethyl-, R3 is trifluoromethyl-, R4 is 3-chloro-5-(trifluoromethyl)phenyl-, Y1-Y2-Y3 is —C═N—S—, A2 is CH, A3 is CH, A4 is CH, and R5b, n and R2 are as defined in Table P.

Table 226
Table 226 provides 720 compounds of formula IA wherein R1 is hydrogen, R3 is dichloromethyl-, R4 is 3-chloro-5-(trifluoromethyl)phenyl-, Y1-Y2-Y3 is —C═N—S—, A2 is CH, A3 is CH, A4 is CH, and R5b, n and R2 are as defined in Table P.

Table 227
Table 227 provides 720 compounds of formula IA wherein R1 is methyl-, R3 is dichloromethyl-, R4 is 3-chloro-5-(trifluoromethyl)phenyl-, Y1-Y2-Y3 is —C═N—S—, A2 is CH, A3 is CH, A4 is CH, and R5b, n and R2 are as defined in Table P.

Table 228
Table 228 provides 720 compounds of formula IA wherein R1 is ethyl-, R3 is dichloromethyl-, R4 is 3-chloro-5-(trifluoromethyl)phenyl-, Y1-Y2-Y3 is —C═N—S—, A2 is CH, A3 is CH, A4 is CH, and R5b, n and R2 are as defined in Table P.

Table 229
Table 229 provides 720 compounds of formula IA wherein R1 is hydrogen, R3 is trifluoromethyl-, R4 is 3,5-bis(trifluoromethyl)phenyl-, Y1-Y2-Y3 is —C═N—S—, A2 is CH, A3 is CH, A4 is CH, and R5b, n and R2 are as defined in Table P.

Table 230
Table 230 provides 720 compounds of formula IA wherein R1 is methyl-, R3 is trifluoromethyl-, R4 is 3,5-bis(trifluoromethyl)phenyl-, Y1-Y2-Y3 is —C═N—S—, A2 is CH, A3 is CH, A4 is CH, and R5b, n and R2 are as defined in Table P.

Table 231
Table 231 provides 720 compounds of formula IA wherein R1 is ethyl-, R3 is trifluoromethyl-, R4 is 3,5-bis(trifluoromethyl)phenyl-, Y1-Y2-Y3 is —C═N—S—, A2 is CH, A3 is CH, A4 is CH, and R5b, n and R2 are as defined in Table P.

Table 232
Table 232 provides 720 compounds of formula IA wherein R1 is hydrogen, R3 is dichloromethyl-, R4 is 3,5-bis(trifluoromethyl)phenyl-, Y1-Y2-Y3 is —C═N—S—, A2 is CH, A3 is CH, A4 is CH, and R5b, n and R2 are as defined in Table P.

Table 233
Table 233 provides 720 compounds of formula IA wherein R1 is methyl-, R3 is dichloromethyl-, R4 is 3,5-bis(trifluoromethyl)phenyl-, Y1-Y2-Y3 is —C═N—S—, A2 is CH, A3 is CH, A4 is CH, and R5b, n and R2 are as defined in Table P.

Table 234
Table 234 provides 720 compounds of formula IA wherein R1 is ethyl-, R3 is dichloromethyl-, R4 is 3,5-bis(trifluoromethyl)phenyl-, Y1-Y2-Y3 is —C═N—S—, A2 is CH, A3 is CH, A4 is CH, and R5b, n and R2 are as defined in Table P.

Table 235
Table 235 provides 720 compounds of formula IA wherein R1 is hydrogen, R3 is trifluoromethyl-, R4 is 3-(trifluoromethyl)phenyl-, Y1-Y2-Y3 is —C═N—S—, A2 is CH, A3 is CH, A4 is CH, and R5b, n and R2 are as defined in Table P.

Table 236
Table 236 provides 720 compounds of formula IA wherein R1 is methyl-, R3 is trifluoromethyl-, R4 is 3-(trifluoromethyl)phenyl-, Y1-Y2-Y3 is —C═N—S—, A2 is CH, A3 is CH, A4 is CH, and R5b, n and R2 are as defined in Table P.

Table 237
Table 237 provides 720 compounds of formula IA wherein R1 is ethyl-, R3 is trifluoromethyl-, R4 is 3-(trifluoromethyl)phenyl-, Y1-Y2-Y3 is —C═N—S—, A2 is CH, A3 is CH, A4 is CH, and R5b, n and R2 are as defined in Table P.

Table 238
Table 238 provides 720 compounds of formula IA wherein R1 is hydrogen, R3 is dichloromethyl-, R4 is 3-(trifluoromethyl)phenyl-, Y1-Y2-Y3 is —C═N—S—, A2 is CH, A3 is CH, A4 is CH, and R5b, n and R2 are as defined in Table P.

Table 239
Table 239 provides 720 compounds of formula IA wherein R1 is methyl-, R3 is dichloromethyl-, R4 is 3-(trifluoromethyl)phenyl-, Y1-Y2-Y3 is —C═N—S—, A2 is CH, A3 is CH, A4 is CH, and R5b, n and R2 are as defined in Table P.

Table 240
Table 240 provides 720 compounds of formula IA wherein R1 is ethyl-, R3 is dichloromethyl-, R4 is 3-(trifluoromethyl)phenyl-, Y1-Y2-Y3 is —C═N—S—, A2 is CH, A3 is CH, A4 is CH, and R5b, n and R2 are as defined in Table P.

Table 241
Table 241 provides 720 compounds of formula IA wherein R1 is hydrogen, R3 is trifluoromethyl-, R4 is 3,5-dichlorophenyl-, Y1-Y2-Y3 is —C═CH—S—, A2 is CH, A3 is CH, A4 is CH, and R5b, n and R2 are as defined in Table P.

Table 242
Table 242 provides 720 compounds of formula IA wherein R1 is methyl-, R3 is trifluoromethyl-, R4 is 3,5-dichlorophenyl-, Y1-Y2-Y3 is —C═CH—S—, A2 is CH, A3 is CH, A4 is CH, and R5b, n and R2 are as defined in Table P.

Table 243
Table 243 provides 720 compounds of formula IA wherein R1 is ethyl-, R3 is trifluoromethyl-, R4 is 3,5-dichlorophenyl-, Y1-Y2-Y3 is —C═CH—S—, A2 is CH, A3 is CH, A4 is CH, and R5b, n and R2 are as defined in Table P.

Table 244
Table 244 provides 720 compounds of formula IA wherein R1 is hydrogen, R3 is dichloromethyl-, R4 is 3,5-dichlorophenyl-, Y1-Y2-Y3 is —C═CH—S—, A2 is CH, A3 is CH, A4 is CH, and R5b, n and R2 are as defined in Table P.

Table 245
Table 245 provides 720 compounds of formula IA wherein R1 is methyl-, R3 is dichloromethyl-, R4 is 3,5-dichlorophenyl-, Y1-Y2-Y3 is —C═CH—S—, A2 is CH, A3 is CH, A4 is CH, and R5b, n and R2 are as defined in Table P.

Table 246
Table 246 provides 720 compounds of formula IA wherein R1 is ethyl-, R3 is dichloromethyl-, R4 is 3,5-dichlorophenyl-, Y1-Y2-Y3 is —C═CH—S—, A2 is CH, A3 is CH, A4 is CH, and R5b, n and R2 are as defined in Table P.

Table 247
Table 247 provides 720 compounds of formula IA wherein R1 is hydrogen, R3 is trifluoromethyl-, R4 is 3,4-dichlorophenyl-, Y1-Y2-Y3 is —C═CH—S—, A2 is CH, A3 is CH, A4 is CH, and R5b, n and R2 are as defined in Table P.

Table 248
Table 248 provides 720 compounds of formula IA wherein R1 is methyl-, R3 is trifluoromethyl-, R4 is 3,4-dichlorophenyl-, Y1-Y2-Y3 is —C═CH—S—, A2 is CH, A3 is CH, A4 is CH, and R5b, n and R2 are as defined in Table P.

Table 249
Table 249 provides 720 compounds of formula IA wherein R1 is ethyl-, R3 is trifluoromethyl-, R4 is 3,4-dichlorophenyl-, Y1-Y2-Y3 is —C═CH—S—, A2 is CH, A3 is CH, A4 is CH, and R5b, n and R2 are as defined in Table P.

Table 250
Table 250 provides 720 compounds of formula IA wherein R1 is hydrogen, R3 is dichloromethyl-, R4 is 3,4-dichlorophenyl-, Y1-Y2-Y3 is —C═CH—S—, A2 is CH, A3 is CH, A4 is CH, and R5b, n and R2 are as defined in Table P.

Table 251

Table 251 provides 720 compounds of formula IA wherein R1 is methyl-, R3 is dichloromethyl-, R4 is 3,4-dichlorophenyl-, Y1-Y2-Y3 is —C=CH—S—, A2 is CH, A3 is CH, A4 is CH, and R5b, n and R2 are as defined in Table P.

Table 252

Table 252 provides 720 compounds of formula IA wherein R1 is ethyl-, R3 is dichloromethyl-, R4 is 3,4-dichlorophenyl-, Y1-Y2-Y3 is —C=CH—S—, A2 is CH, A3 is CH, A4 is CH, and R5b, n and R2 are as defined in Table P.

Table 253

Table 253 provides 720 compounds of formula IA wherein R1 is hydrogen, R3 is trifluoromethyl-, R4 is 3,5-dichloro-4-fluorophenyl-, Y1-Y2-Y3 is —C=CH—S—, A2 is CH, A3 is CH, A4 is CH, and R5b, n and R2 are as defined in Table P.

Table 254

Table 254 provides 720 compounds of formula IA wherein R1 is methyl-, R3 is trifluoromethyl-, R4 is 3,5-dichloro-4-fluorophenyl-, Y1-Y2-Y3 is —C=CH—S—, A2 is CH, A3 is CH, A4 is CH, and R5b, n and R2 are as defined in Table P.

Table 255

Table 255 provides 720 compounds of formula IA wherein R1 is ethyl-, R3 is trifluoromethyl-, R4 is 3,5-dichloro-4-fluorophenyl-, Y1-Y2-Y3 is —C=CH—S—, A2 is CH, A3 is CH, A4 is CH, and R5b, n and R2 are as defined in Table P.

Table 256

Table 256 provides 720 compounds of formula IA wherein R1 is hydrogen, R3 is dichloromethyl-, R4 is 3,5-dichloro-4-fluorophenyl-, Y1-Y2-Y3 is —C=CH—S—, A2 is CH, A3 is CH, A4 is CH, and R5b, n and R2 are as defined in Table P.

Table 257

Table 257 provides 720 compounds of formula IA wherein R1 is methyl-, R3 is dichloromethyl-, R4 is 3,5-dichloro-4-fluorophenyl-, Y1-Y2-Y3 is —C=CH—S—, A2 is CH, A3 is CH, A4 is CH, and R5b, n and R2 are as defined in Table P.

Table 258

Table 258 provides 720 compounds of formula IA wherein R1 is ethyl-, R3 is dichloromethyl-, R4 is 3,5-dichloro-4-fluorophenyl-, Y1-Y2-Y3 is —C=CH—S—, A2 is CH, A3 is CH, A4 is CH, and R5b, n and R2 are as defined in Table P.

Table 259

Table 259 provides 720 compounds of formula IA wherein R1 is hydrogen, R3 is trifluoromethyl-, R4 is 3,4,5-trichlorophenyl-, Y1-Y2-Y3 is —C=CH—S—, A2 is CH, A3 is CH, A4 is CH, and R5b, n and R2 are as defined in Table P.

Table 260

Table 260 provides 720 compounds of formula IA wherein R1 is methyl-, R3 is trifluoromethyl-, R4 is 3,4,5-trichlorophenyl-, Y1-Y2-Y3 is —C=CH—S—, A2 is CH, A3 is CH, A4 is CH, and R5b, n and R2 are as defined in Table P.

Table 261

Table 261 provides 720 compounds of formula IA wherein R1 is ethyl-, R3 is trifluoromethyl-, R4 is 3,4,5-trichlorophenyl-, Y1-Y2-Y3 is —C=CH—S—, A2 is CH, A3 is CH, A4 is CH, and R5b, n and R2 are as defined in Table P.

Table 262

Table 262 provides 720 compounds of formula IA wherein R1 is hydrogen, R3 is dichloromethyl-, R4 is 3,4,5-trichlorophenyl-, Y1-Y2-Y3 is —C=CH—S—, A2 is CH, A3 is CH, A4 is CH, and R5b, n and R2 are as defined in Table P.

Table 263

Table 263 provides 720 compounds of formula IA wherein R1 is methyl-, R3 is dichloromethyl-, R4 is 3,4,5-trichlorophenyl-, Y1-Y2-Y3 is —C=CH—S—, A2 is CH, A3 is CH, A4 is CH, and R5b, n and R2 are as defined in Table P.

Table 264

Table 264 provides 720 compounds of formula IA wherein R1 is ethyl-, R3 is dichloromethyl-, R4 is 3,4,5-trichlorophenyl-, Y1-Y2-Y3 is —C=CH—S—, A2 is CH, A3 is CH, A4 is CH, and R5b, n and R2 are as defined in Table P.

Table 265

Table 265 provides 720 compounds of formula IA wherein R1 is hydrogen, R3 is trifluoromethyl-, R4 is 3-chloro-5-fluorophenyl-, Y1-Y2-Y3 is —C=CH—S—, A2 is CH, A3 is CH, A4 is CH, and R5b, n and R2 are as defined in Table P.

Table 266

Table 266 provides 720 compounds of formula IA wherein R1 is methyl-, R3 is trifluoromethyl-, R4 is 3-chloro-5-fluorophenyl-, Y1-Y2-Y3 is —C=CH—S—, A2 is CH, A3 is CH, A4 is CH, and R5b, n and R2 are as defined in Table P.

Table 267

Table 267 provides 720 compounds of formula IA wherein R1 is ethyl-, R3 is trifluoromethyl-, R4 is 3-chloro-5-fluorophenyl-, Y1-Y2-Y3 is —C=CH—S—, A2 is CH, A3 is CH, A4 is CH, and R5b, n and R2 are as defined in Table P.

Table 268

Table 268 provides 720 compounds of formula IA wherein R1 is hydrogen, R3 is dichloromethyl-, R4 is 3-chloro-5-fluorophenyl-, Y1-Y2-Y3 is —C=CH—S—, A2 is CH, A3 is CH, A4 is CH, and R5b, n and R2 are as defined in Table P.

Table 269

Table 269 provides 720 compounds of formula IA wherein R1 is methyl-, R3 is dichloromethyl-, R4 is 3-chloro-5-fluorophenyl-, Y1-Y2-Y3 is —C=CH—S—, A2 is CH, A3 is CH, A4 is CH, and R5b, n and R2 are as defined in Table P.

Table 270

Table 270 provides 720 compounds of formula IA wherein R1 is ethyl-, R3 is dichloromethyl-, R4 is 3-chloro-5-fluorophenyl-, Y1-Y2-Y3 is —C=CH—S—, A2 is CH, A3 is CH, A4 is CH, and R5b, n and R2 are as defined in Table P.

Table 271

Table 271 provides 720 compounds of formula IA wherein R1 is hydrogen, R3 is trifluoromethyl-, R4 is 3-chloro-5-(trifluoromethyl)phenyl-, Y1-Y2-Y3 is —C=CH—S—, A2 is CH, A3 is CH, A4 is CH, and R5b, n and R2 are as defined in Table P.

Table 272

Table 272 provides 720 compounds of formula IA wherein R1 is methyl-, R3 is trifluoromethyl-, R4 is 3-chloro-5-(trifluoromethyl)phenyl-, Y1-Y2-Y3 is —C=CH—S—, A2 is CH, A3 is CH, A4 is CH, and R5b, n and R2 are as defined in Table P.

Table 273

Table 273 provides 720 compounds of formula IA wherein R1 is ethyl-, R3 is trifluoromethyl-, R4 is 3-chloro-5-(trifluoromethyl)phenyl-, Y1-Y2-Y3 is —C=CH—S—, A2 is CH, A3 is CH, A4 is CH, and R5b, n and R2 are as defined in Table P.

Table 274

Table 274 provides 720 compounds of formula IA wherein R1 is hydrogen, R3 is dichloromethyl-, R4 is 3-chloro-5-(trifluoromethyl)phenyl-, Y1-Y2-Y3 is —C=CH—S—, A2 is CH, A3 is CH, A4 is CH, and R5b, n and R2 are as defined in Table P.

Table 275

Table 275 provides 720 compounds of formula IA wherein R1 is methyl-, R3 is dichloromethyl-, R4 is 3-chloro-5-(trifluoromethyl)phenyl-, Y1-Y2-Y3 is —C=CH—S—, A2 is CH, A3 is CH, A4 is CH, and R5b, n and R2 are as defined in Table P.

Table 276

Table 276 provides 720 compounds of formula IA wherein R1 is ethyl-, R3 is dichloromethyl-, R4 is 3-chloro-5-(trifluoromethyl)phenyl-, Y1-Y2-Y3 is —C=CH—S—, A2 is CH, A3 is CH, A4 is CH, and R5b, n and R2 are as defined in Table P.

Table 277

Table 277 provides 720 compounds of formula IA wherein R1 is hydrogen, R3 is trifluoromethyl-, R4 is 3,5-bis(trifluoromethyl)phenyl-, Y1-Y2-Y3 is —C=CH—S—, A2 is CH, A3 is CH, A4 is CH, and R5b, n and R2 are as defined in Table P.

Table 278

Table 278 provides 720 compounds of formula IA wherein R1 is methyl-, R3 is trifluoromethyl-, R4 is 3,5-bis(trifluoromethyl)phenyl-, Y1-Y2-Y3 is —C=CH—S—, A2 is CH, A3 is CH, A4 is CH, and R5b, n and R2 are as defined in Table P.

Table 279

Table 279 provides 720 compounds of formula IA wherein R1 is ethyl-, R3 is trifluoromethyl-, R4 is 3,5-bis(trifluoromethyl)phenyl-, Y1-Y2-Y3 is —C=CH—S—, A2 is CH, A3 is CH, A4 is CH, and R5b, n and R2 are as defined in Table P.

Table 280

Table 280 provides 720 compounds of formula IA wherein R1 is hydrogen, R3 is dichloromethyl-, R4 is 3,5-bis(trifluoromethyl)phenyl-, Y1-Y2-Y3 is —C=CH—S—, A2 is CH, A3 is CH, A4 is CH, and R5b, n and R2 are as defined in Table P.

Table 281

Table 281 provides 720 compounds of formula IA wherein R1 is methyl-, R3 is dichloromethyl-, R4 is 3,5-bis(trifluoromethyl)phenyl-, Y1-Y2-Y3 is —C=CH—S—, A2 is CH, A3 is CH, A4 is CH, and R5b, n and R2 are as defined in Table P.

Table 282

Table 282 provides 720 compounds of formula IA wherein R1 is ethyl-, R3 is dichloromethyl-, R4 is 3,5-bis(trifluoromethyl)phenyl-, Y1-Y2-Y3 is —C=CH—S—, A2 is CH, A3 is CH, A4 is CH, and R5b, n and R2 are as defined in Table P.

Table 283

Table 283 provides 720 compounds of formula IA wherein R1 is hydrogen, R3 is trifluoromethyl-, R4 is 3-(trifluoromethyl)phenyl-, Y1-Y2-Y3 is —C=CH—S—, A2 is CH, A3 is CH, A4 is CH, and R5b, n and R2 are as defined in Table P.

Table 284

Table 284 provides 720 compounds of formula IA wherein R1 is methyl-, R3 is trifluoromethyl-, R4 is 3-(trifluoromethyl)phenyl-, Y1-Y2-Y3 is —C=CH—S—, A2 is CH, A3 is CH, A4 is CH, and R5b, n and R2 are as defined in Table P.

Table 285

Table 285 provides 720 compounds of formula IA wherein R1 is ethyl-, R3 is trifluoromethyl-, R4 is 3-(trifluoromethyl)phenyl-, Y1-Y2-Y3 is —C=CH—S—, A2 is CH, A3 is CH, A4 is CH, and R5b, n and R2 are as defined in Table P.

Table 286

Table 286 provides 720 compounds of formula IA wherein R1 is hydrogen, R3 is dichloromethyl-, R4 is 3-(trifluoromethyl)phenyl-, Y1-Y2-Y3 is —C=CH—S—, A2 is CH, A3 is CH, A4 is CH, and R5b, n and R2 are as defined in Table P.

Table 287

Table 287 provides 720 compounds of formula IA wherein R1 is methyl-, R3 is dichloromethyl-, R4 is 3-(trifluoromethyl)phenyl-, Y1-Y2-Y3 is —C=CH—S—, A2 is CH, A3 is CH, A4 is CH, and R5b, n and R2 are as defined in Table P.

Table 288

Table 288 provides 720 compounds of formula IA wherein R1 is ethyl-, R3 is dichloromethyl-, R4 is 3-(trifluoromethyl)phenyl-, Y1-Y2-Y3 is —C=CH—S—, A2 is CH, A3 is CH, A4 is CH, and R5b, n and R2 are as defined in Table P.

TABLE Q

|    | R5b | n | R3 | R4 |
| --- | --- | --- | --- | --- |
| 1 | methyl- | 0 | trifluoromethyl- | 3,5-dichlorophenyl- |
| 2 | chloro- | 0 | trifluoromethyl- | 3,5-dichlorophenyl- |
| 3 | bromo- | 0 | trifluoromethyl- | 3,5-dichlorophenyl- |
| 4 | trifluoromethyl- | 0 | trifluoromethyl- | 3,5-dichlorophenyl- |
| 5 | methyl- | 1 | trifluoromethyl- | 3,5-dichlorophenyl- |
| 6 | chloro- | 1 | trifluoromethyl- | 3,5-dichlorophenyl- |
| 7 | bromo- | 1 | trifluoromethyl- | 3,5-dichlorophenyl- |
| 8 | trifluoromethyl- | 1 | trifluoromethyl- | 3,5-dichlorophenyl- |
| 9 | methyl- | 2 | trifluoromethyl- | 3,5-dichlorophenyl- |
| 10 | chloro- | 2 | trifluoromethyl- | 3,5-dichlorophenyl- |
| 11 | bromo- | 2 | trifluoromethyl- | 3,5-dichlorophenyl- |
| 12 | trifluoromethyl- | 2 | trifluoromethyl- | 3,5-dichlorophenyl- |
| 13 | methyl- | 0 | dichloromethyl- | 3,5-dichlorophenyl- |
| 14 | chloro- | 0 | dichloromethyl- | 3,5-dichlorophenyl- |
| 15 | bromo- | 0 | dichloromethyl- | 3,5-dichlorophenyl- |
| 16 | trifluoromethyl- | 0 | dichloromethyl- | 3,5-dichlorophenyl- |
| 17 | methyl- | 1 | dichloromethyl- | 3,5-dichlorophenyl- |

TABLE Q-continued

| | R5b | n | R3 | R4 |
|---|---|---|---|---|
| 18 | chloro- | 1 | dichloromethyl- | 3,5-dichlorophenyl- |
| 19 | bromo- | 1 | dichloromethyl- | 3,5-dichlorophenyl- |
| 20 | trifluoromethyl- | 1 | dichloromethyl- | 3,5-dichlorophenyl- |
| 21 | methyl- | 2 | dichloromethyl- | 3,5-dichlorophenyl- |
| 22 | chloro- | 2 | dichloromethyl- | 3,5-dichlorophenyl- |
| 23 | bromo- | 2 | dichloromethyl- | 3,5-dichlorophenyl- |
| 24 | trifluoromethyl- | 2 | dichloromethyl- | 3,5-dichlorophenyl- |
| 25 | methyl- | 0 | trifluoromethyl- | 3,4-dichlorophenyl- |
| 26 | chloro- | 0 | trifluoromethyl- | 3,4-dichlorophenyl- |
| 27 | bromo- | 0 | trifluoromethyl- | 3,4-dichlorophenyl- |
| 28 | trifluoromethyl- | 0 | trifluoromethyl- | 3,4-dichlorophenyl- |
| 29 | methyl- | 1 | trifluoromethyl- | 3,4-dichlorophenyl- |
| 30 | chloro- | 1 | trifluoromethyl- | 3,4-dichlorophenyl- |
| 31 | bromo- | 1 | trifluoromethyl- | 3,4-dichlorophenyl- |
| 32 | trifluoromethyl- | 1 | trifluoromethyl- | 3,4-dichlorophenyl- |
| 33 | methyl- | 2 | trifluoromethyl- | 3,4-dichlorophenyl- |
| 34 | chloro- | 2 | trifluoromethyl- | 3,4-dichlorophenyl- |
| 35 | bromo- | 2 | trifluoromethyl- | 3,4-dichlorophenyl- |
| 36 | trifluoromethyl- | 2 | trifluoromethyl- | 3,4-dichlorophenyl- |
| 37 | methyl- | 0 | dichloromethyl- | 3,4-dichlorophenyl- |
| 38 | chloro- | 0 | dichloromethyl- | 3,4-dichlorophenyl- |
| 39 | bromo- | 0 | dichloromethyl- | 3,4-dichlorophenyl- |
| 40 | trifluoromethyl- | 0 | dichloromethyl- | 3,4-dichlorophenyl- |
| 41 | methyl- | 1 | dichloromethyl- | 3,4-dichlorophenyl- |
| 42 | chloro- | 1 | dichloromethyl- | 3,4-dichlorophenyl- |
| 43 | bromo- | 1 | dichloromethyl- | 3,4-dichlorophenyl- |
| 44 | trifluoromethyl- | 1 | dichloromethyl- | 3,4-dichlorophenyl- |
| 45 | methyl- | 2 | dichloromethyl- | 3,4-dichlorophenyl- |
| 46 | chloro- | 2 | dichloromethyl- | 3,4-dichlorophenyl- |
| 47 | bromo- | 2 | dichloromethyl- | 3,4-dichlorophenyl- |
| 48 | trifluoromethyl- | 2 | dichloromethyl- | 3,4-dichlorophenyl- |
| 49 | methyl- | 0 | trifluoromethyl- | 3,5-dichloro-4-fluorophenyl- |
| 50 | chloro- | 0 | trifluoromethyl- | 3,5-dichloro-4-fluorophenyl- |
| 51 | bromo- | 0 | trifluoromethyl- | 3,5-dichloro-4-fluorophenyl- |
| 52 | trifluoromethyl- | 0 | trifluoromethyl- | 3,5-dichloro-4-fluorophenyl- |
| 53 | methyl- | 1 | trifluoromethyl- | 3,5-dichloro-4-fluorophenyl- |
| 54 | chloro- | 1 | trifluoromethyl- | 3,5-dichloro-4-fluorophenyl- |
| 55 | bromo- | 1 | trifluoromethyl- | 3,5-dichloro-4-fluorophenyl- |
| 56 | trifluoromethyl- | 1 | trifluoromethyl- | 3,5-dichloro-4-fluorophenyl- |
| 57 | methyl- | 2 | trifluoromethyl- | 3,5-dichloro-4-fluorophenyl- |
| 58 | chloro- | 2 | trifluoromethyl- | 3,5-dichloro-4-fluorophenyl- |
| 59 | bromo- | 2 | trifluoromethyl- | 3,5-dichloro-4-fluorophenyl- |
| 60 | trifluoromethyl- | 2 | trifluoromethyl- | 3,5-dichloro-4-fluorophenyl- |
| 61 | methyl- | 0 | dichloromethyl- | 3,5-dichloro-4-fluorophenyl- |
| 62 | chloro- | 0 | dichloromethyl- | 3,5-dichloro-4-fluorophenyl- |
| 63 | bromo- | 0 | dichloromethyl- | 3,5-dichloro-4-fluorophenyl- |
| 64 | trifluoromethyl- | 0 | dichloromethyl- | 3,5-dichloro-4-fluorophenyl- |
| 65 | methyl- | 1 | dichloromethyl- | 3,5-dichloro-4-fluorophenyl- |
| 66 | chloro- | 1 | dichloromethyl- | 3,5-dichloro-4-fluorophenyl- |
| 67 | bromo- | 1 | dichloromethyl- | 3,5-dichloro-4-fluorophenyl- |
| 68 | trifluoromethyl- | 1 | dichloromethyl- | 3,5-dichloro-4-fluorophenyl- |
| 69 | methyl- | 2 | dichloromethyl- | 3,5-dichloro-4-fluorophenyl- |
| 70 | chloro- | 2 | dichloromethyl- | 3,5-dichloro-4-fluorophenyl- |
| 71 | bromo- | 2 | dichloromethyl- | 3,5-dichloro-4-fluorophenyl- |
| 72 | trifluoromethyl- | 2 | dichloromethyl- | 3,5-dichloro-4-fluorophenyl- |
| 73 | methyl- | 0 | trifluoromethyl- | 3,4,5-trichlorophenyl- |
| 74 | chloro- | 0 | trifluoromethyl- | 3,4,5-trichlorophenyl- |
| 75 | bromo- | 0 | trifluoromethyl- | 3,4,5-trichlorophenyl- |
| 76 | trifluoromethyl- | 0 | trifluoromethyl- | 3,4,5-trichlorophenyl- |
| 77 | methyl- | 1 | trifluoromethyl- | 3,4,5-trichlorophenyl- |
| 78 | chloro- | 1 | trifluoromethyl- | 3,4,5-trichlorophenyl- |
| 79 | bromo- | 1 | trifluoromethyl- | 3,4,5-trichlorophenyl- |
| 80 | trifluoromethyl- | 1 | trifluoromethyl- | 3,4,5-trichlorophenyl- |
| 81 | methyl- | 2 | trifluoromethyl- | 3,4,5-trichlorophenyl- |
| 82 | chloro- | 2 | trifluoromethyl- | 3,4,5-trichlorophenyl- |
| 83 | bromo- | 2 | trifluoromethyl- | 3,4,5-trichlorophenyl- |
| 84 | trifluoromethyl- | 2 | trifluoromethyl- | 3,4,5-trichlorophenyl- |
| 85 | methyl- | 0 | dichloromethyl- | 3,4,5-trichlorophenyl- |
| 86 | chloro- | 0 | dichloromethyl- | 3,4,5-trichlorophenyl- |
| 87 | bromo- | 0 | dichloromethyl- | 3,4,5-trichlorophenyl- |
| 88 | trifluoromethyl- | 0 | dichloromethyl- | 3,4,5-trichlorophenyl- |
| 89 | methyl- | 1 | dichloromethyl- | 3,4,5-trichlorophenyl- |
| 90 | chloro- | 1 | dichloromethyl- | 3,4,5-trichlorophenyl- |
| 91 | bromo- | 1 | dichloromethyl- | 3,4,5-trichlorophenyl- |
| 92 | trifluoromethyl- | 1 | dichloromethyl- | 3,4,5-trichlorophenyl- |
| 93 | methyl- | 2 | dichloromethyl- | 3,4,5-trichlorophenyl- |
| 94 | chloro- | 2 | dichloromethyl- | 3,4,5-trichlorophenyl- |
| 95 | bromo- | 2 | dichloromethyl- | 3,4,5-trichlorophenyl- |

TABLE Q-continued

| | R5b | n | R3 | R4 |
|---|---|---|---|---|
| 96 | trifluoromethyl- | 2 | dichloromethyl- | 3,4,5-trichlorophenyl- |
| 97 | methyl- | 0 | trifluoromethyl- | 3-chloro-5-fluorophenyl- |
| 98 | chloro- | 0 | trifluoromethyl- | 3-chloro-5-fluorophenyl- |
| 99 | bromo- | 0 | trifluoromethyl- | 3-chloro-5-fluorophenyl- |
| 100 | trifluoromethyl- | 0 | trifluoromethyl- | 3-chloro-5-fluorophenyl- |
| 101 | methyl- | 1 | trifluoromethyl- | 3-chloro-5-fluorophenyl- |
| 102 | chloro- | 1 | trifluoromethyl- | 3-chloro-5-fluorophenyl- |
| 103 | bromo- | 1 | trifluoromethyl- | 3-chloro-5-fluorophenyl- |
| 104 | trifluoromethyl- | 1 | trifluoromethyl- | 3-chloro-5-fluorophenyl- |
| 105 | methyl- | 2 | trifluoromethyl- | 3-chloro-5-fluorophenyl- |
| 106 | chloro- | 2 | trifluoromethyl- | 3-chloro-5-fluorophenyl- |
| 107 | bromo- | 2 | trifluoromethyl- | 3-chloro-5-fluorophenyl- |
| 108 | trifluoromethyl- | 2 | trifluoromethyl- | 3-chloro-5-fluorophenyl- |
| 109 | methyl- | 0 | dichloromethyl- | 3-chloro-5-fluorophenyl- |
| 110 | chloro- | 0 | dichloromethyl- | 3-chloro-5-fluorophenyl- |
| 111 | bromo- | 0 | dichloromethyl- | 3-chloro-5-fluorophenyl- |
| 112 | trifluoromethyl- | 0 | dichloromethyl- | 3-chloro-5-fluorophenyl- |
| 113 | methyl- | 1 | dichloromethyl- | 3-chloro-5-fluorophenyl- |
| 114 | chloro- | 1 | dichloromethyl- | 3-chloro-5-fluorophenyl- |
| 115 | bromo- | 1 | dichloromethyl- | 3-chloro-5-fluorophenyl- |
| 116 | trifluoromethyl- | 1 | dichloromethyl- | 3-chloro-5-fluorophenyl- |
| 117 | methyl- | 2 | dichloromethyl- | 3-chloro-5-fluorophenyl- |
| 118 | chloro- | 2 | dichloromethyl- | 3-chloro-5-fluorophenyl- |
| 119 | bromo- | 2 | dichloromethyl- | 3-chloro-5-fluorophenyl- |
| 120 | trifluoromethyl- | 2 | dichloromethyl- | 3-chloro-5-fluorophenyl- |
| 121 | methyl- | 0 | trifluoromethyl- | 3-chloro-5-(trifluoromethyl)phenyl- |
| 122 | chloro- | 0 | trifluoromethyl- | 3-chloro-5-(trifluoromethyl)phenyl- |
| 123 | bromo- | 0 | trifluoromethyl- | 3-chloro-5-(trifluoromethyl)phenyl- |
| 124 | trifluoromethyl- | 0 | trifluoromethyl- | 3-chloro-5-(trifluoromethyl)phenyl- |
| 125 | methyl- | 1 | trifluoromethyl- | 3-chloro-5-(trifluoromethyl)phenyl- |
| 126 | chloro- | 1 | trifluoromethyl- | 3-chloro-5-(trifluoromethyl)phenyl- |
| 127 | bromo- | 1 | trifluoromethyl- | 3-chloro-5-(trifluoromethyl)phenyl- |
| 128 | trifluoromethyl- | 1 | trifluoromethyl- | 3-chloro-5-(trifluoromethyl)phenyl- |
| 129 | methyl- | 2 | trifluoromethyl- | 3-chloro-5-(trifluoromethyl)phenyl- |
| 130 | chloro- | 2 | trifluoromethyl- | 3-chloro-5-(trifluoromethyl)phenyl- |
| 131 | bromo- | 2 | trifluoromethyl- | 3-chloro-5-(trifluoromethyl)phenyl- |
| 132 | trifluoromethyl- | 2 | trifluoromethyl- | 3-chloro-5-(trifluoromethyl)phenyl- |
| 133 | methyl- | 0 | dichloromethyl- | 3-chloro-5-(trifluoromethyl)phenyl- |
| 134 | chloro- | 0 | dichloromethyl- | 3-chloro-5-(trifluoromethyl)phenyl- |
| 135 | bromo- | 0 | dichloromethyl- | 3-chloro-5-(trifluoromethyl)phenyl- |
| 136 | trifluoromethyl- | 0 | dichloromethyl- | 3-chloro-5-(trifluoromethyl)phenyl- |
| 137 | methyl- | 1 | dichloromethyl- | 3-chloro-5-(trifluoromethyl)phenyl- |
| 138 | chloro- | 1 | dichloromethyl- | 3-chloro-5-(trifluoromethyl)phenyl- |
| 139 | bromo- | 1 | dichloromethyl- | 3-chloro-5-(trifluoromethyl)phenyl- |
| 140 | trifluoromethyl- | 1 | dichloromethyl- | 3-chloro-5-(trifluoromethyl)phenyl- |
| 141 | methyl- | 2 | dichloromethyl- | 3-chloro-5-(trifluoromethyl)phenyl- |
| 142 | chloro- | 2 | dichloromethyl- | 3-chloro-5-(trifluoromethyl)phenyl- |
| 143 | bromo- | 2 | dichloromethyl- | 3-chloro-5-(trifluoromethyl)phenyl- |
| 144 | trifluoromethyl- | 2 | dichloromethyl- | 3-chloro-5-(trifluoromethyl)phenyl- |
| 145 | methyl- | 0 | trifluoromethyl- | 3,5-bis(trifluoromethyl)phenyl- |
| 146 | chloro- | 0 | trifluoromethyl- | 3,5-bis(trifluoromethyl)phenyl- |
| 147 | bromo- | 0 | trifluoromethyl- | 3,5-bis(trifluoromethyl)phenyl- |
| 148 | trifluoromethyl- | 0 | trifluoromethyl- | 3,5-bis(trifluoromethyl)phenyl- |
| 149 | methyl- | 1 | trifluoromethyl- | 3,5-bis(trifluoromethyl)phenyl- |
| 150 | chloro- | 1 | trifluoromethyl- | 3,5-bis(trifluoromethyl)phenyl- |
| 151 | bromo- | 1 | trifluoromethyl- | 3,5-bis(trifluoromethyl)phenyl- |
| 152 | trifluoromethyl- | 1 | trifluoromethyl- | 3,5-bis(trifluoromethyl)phenyl- |
| 153 | methyl- | 2 | trifluoromethyl- | 3,5-bis(trifluoromethyl)phenyl- |
| 154 | chloro- | 2 | trifluoromethyl- | 3,5-bis(trifluoromethyl)phenyl- |
| 155 | bromo- | 2 | trifluoromethyl- | 3,5-bis(trifluoromethyl)phenyl- |
| 156 | trifluoromethyl- | 2 | trifluoromethyl- | 3,5-bis(trifluoromethyl)phenyl- |
| 157 | methyl- | 0 | dichloromethyl- | 3,5-bis(trifluoromethyl)phenyl- |
| 158 | chloro- | 0 | dichloromethyl- | 3,5-bis(trifluoromethyl)phenyl- |
| 159 | bromo- | 0 | dichloromethyl- | 3,5-bis(trifluoromethyl)phenyl- |
| 160 | trifluoromethyl- | 0 | dichloromethyl- | 3,5-bis(trifluoromethyl)phenyl- |
| 161 | methyl- | 1 | dichloromethyl- | 3,5-bis(trifluoromethyl)phenyl- |
| 162 | chloro- | 1 | dichloromethyl- | 3,5-bis(trifluoromethyl)phenyl- |
| 163 | bromo- | 1 | dichloromethyl- | 3,5-bis(trifluoromethyl)phenyl- |
| 164 | trifluoromethyl- | 1 | dichloromethyl- | 3,5-bis(trifluoromethyl)phenyl- |
| 165 | methyl- | 2 | dichloromethyl- | 3,5-bis(trifluoromethyl)phenyl- |
| 166 | chloro- | 2 | dichloromethyl- | 3,5-bis(trifluoromethyl)phenyl- |
| 167 | bromo- | 2 | dichloromethyl- | 3,5-bis(trifluoromethyl)phenyl- |
| 168 | trifluoromethyl- | 2 | dichloromethyl- | 3,5-bis(trifluoromethyl)phenyl- |
| 169 | methyl- | 0 | trifluoromethyl- | 3-(trifluoromethyl)phenyl- |
| 170 | chloro- | 0 | trifluoromethyl- | 3-(trifluoromethyl)phenyl- |
| 171 | bromo- | 0 | trifluoromethyl- | 3-(trifluoromethyl)phenyl- |
| 172 | trifluoromethyl- | 0 | trifluoromethyl- | 3-(trifluoromethyl)phenyl- |
| 173 | methyl- | 1 | trifluoromethyl- | 3-(trifluoromethyl)phenyl- |

TABLE Q-continued

| | R5b | n | R3 | R4 |
|---|---|---|---|---|
| 174 | chloro- | 1 | trifluoromethyl- | 3-(trifluoromethyl)phenyl- |
| 175 | bromo- | 1 | trifluoromethyl- | 3-(trifluoromethyl)phenyl- |
| 176 | trifluoromethyl- | 1 | trifluoromethyl- | 3-(trifluoromethyl)phenyl- |
| 177 | methyl- | 2 | trifluoromethyl- | 3-(trifluoromethyl)phenyl- |
| 178 | chloro- | 2 | trifluoromethyl- | 3-(trifluoromethyl)phenyl- |
| 179 | bromo- | 2 | trifluoromethyl- | 3-(trifluoromethyl)phenyl- |
| 180 | trifluoromethyl- | 2 | trifluoromethyl- | 3-(trifluoromethyl)phenyl- |
| 181 | methyl- | 0 | dichloromethyl- | 3-(trifluoromethyl)phenyl- |
| 182 | chloro- | 0 | dichloromethyl- | 3-(trifluoromethyl)phenyl- |
| 183 | bromo- | 0 | dichloromethyl- | 3-(trifluoromethyl)phenyl- |
| 184 | trifluoromethyl- | 0 | dichloromethyl- | 3-(trifluoromethyl)phenyl- |
| 185 | methyl- | 1 | dichloromethyl- | 3-(trifluoromethyl)phenyl- |
| 186 | chloro- | 1 | dichloromethyl- | 3-(trifluoromethyl)phenyl- |
| 187 | bromo- | 1 | dichloromethyl- | 3-(trifluoromethyl)phenyl- |
| 188 | trifluoromethyl- | 1 | dichloromethyl- | 3-(trifluoromethyl)phenyl- |
| 189 | methyl- | 2 | dichloromethyl- | 3-(trifluoromethyl)phenyl- |
| 190 | chloro- | 2 | dichloromethyl- | 3-(trifluoromethyl)phenyl- |
| 191 | bromo- | 2 | dichloromethyl- | 3-(trifluoromethyl)phenyl- |
| 192 | trifluoromethyl- | 2 | dichloromethyl- | 3-(trifluoromethyl)phenyl- |

Table 289

Table 289 provides 192 compounds of formula IA wherein R1 and R2 together represent the ring fragment (CH2)3, Y1-Y2-Y3 is —C=N—O—, A2 is CH, A3 is CH, A4 is CH, and R5b, n, R3 and R4 are as defined in Table Q.

Table 290

Table 290 provides 192 compounds of formula IA wherein R1 and R2 together represent the ring fragment (CH2)4, Y1-Y2-Y3 is —C=N—O—, A2 is CH, A3 is CH, A4 is CH, and R5b, n, R3 and R4 are as defined in Table Q.

Table 291

Table 291 provides 192 compounds of formula IA wherein R1 and R2 together represent the ring fragment (CH2)5, Y1-Y2-Y3 is —C=N—O—, A2 is CH, A3 is CH, A4 is CH, and R5b, n, R3 and R4 are as defined in Table Q.

Table 292

Table 292 provides 192 compounds of formula IA wherein R1 and R2 together represent the ring fragment (CH2)20(CH2)2, Y1-Y2-Y3 is —C=N—O—, A2 is CH, A3 is CH, A4 is CH, and R5b, n, R3 and R4 are as defined in Table Q.

Table 293

Table 293 provides 192 compounds of formula IA wherein R1 and R2 together represent the ring fragment (CH2)3, Y1-Y2-Y3 is —C=N—CH2-, A2 is CH, A3 is CH, A4 is CH, and R5b, n, R3 and R4 are as defined in Table Q.

Table 294

Table 294 provides 192 compounds of formula IA wherein R1 and R2 together represent the ring fragment (CH2)4, Y1-Y2-Y3 is —C=N—CH2-, A2 is CH, A3 is CH, A4 is CH, and R5b, n, R3 and R4 are as defined in Table Q.

Table 295

Table 295 provides 192 compounds of formula IA wherein R1 and R2 together represent the ring fragment (CH2)5, Y1-Y2-Y3 is —C=N—CH2-, A2 is CH, A3 is CH, A4 is CH, and R5b, n, R3 and R4 are as defined in Table Q.

Table 296

Table 296 provides 192 compounds of formula IA wherein R1 and R2 together represent the ring fragment (CH2)20(CH2)2, Y1-Y2-Y3 is —C=N—CH2-, A2 is CH, A3 is CH, A4 is CH, and R5b, n, R3 and R4 are as defined in Table Q.

Table 297

Table 297 provides 192 compounds of formula IA wherein R1 and R2 together represent the ring fragment (CH2)3, Y1-Y2-Y3 is —N—CH2-CH2-, A2 is CH, A3 is CH, A4 is CH, and R5b, n, R3 and R4 are as defined in Table Q.

Table 298

Table 298 provides 192 compounds of formula IA wherein R1 and R2 together represent the ring fragment (CH2)4, Y1-Y2-Y3 is —N—CH2-CH2-, A2 is CH, A3 is CH, A4 is CH, and R5b, n, R3 and R4 are as defined in Table Q.

Table 299

Table 299 provides 192 compounds of formula IA wherein R1 and R2 together represent the ring fragment (CH2)5, Y1-Y2-Y3 is —N—CH2-CH2-, A2 is CH, A3 is CH, A4 is CH, and R5b, n, R3 and R4 are as defined in Table Q.

Table 300

Table 300 provides 192 compounds of formula IA wherein R1 and R2 together represent the ring fragment (CH2)20(CH2)2, Y1-Y2-Y3 is —N—CH2-CH2-, A2 is CH, A3 is CH, A4 is CH, and R5b, n, R3 and R4 are as defined in Table Q.

Table 301

Table 301 provides 192 compounds of formula IA wherein R1 and R2 together represent the ring fragment (CH2)3, Y1-Y2-Y3 is —C=CH—O—, A2 is CH, A3 is CH, A4 is CH, and R5b, n, R3 and R4 are as defined in Table Q.

Table 302

Table 302 provides 192 compounds of formula IA wherein R1 and R2 together represent the ring fragment (CH2)4, Y1-Y2-Y3 is —C=CH—O—, A2 is CH, A3 is CH, A4 is CH, and R5b, n, R3 and R4 are as defined in Table Q.

Table 303

Table 303 provides 192 compounds of formula IA wherein R1 and R2 together represent the ring fragment (CH2)5, Y1-Y2-Y3 is —C=CH—O—, A2 is CH, A3 is CH, A4 is CH, and R5b, n, R3 and R4 are as defined in Table Q.

Table 304

Table 304 provides 192 compounds of formula IA wherein R1 and R2 together represent the ring fragment (CH2)20(CH2)2, Y1-Y2-Y3 is —C=CH—O—, A2 is CH, A3 is CH, A4 is CH, and R5b, n, R3 and R4 are as defined in Table Q.

Table 305

Table 305 provides 192 compounds of formula IA wherein R1 and R2 together represent the ring fragment (CH2)3, Y1-Y2-Y3 is —C=N—S—, A2 is CH, A3 is CH, A4 is CH, and R5b, n, R3 and R4 are as defined in Table Q.

Table 306

Table 306 provides 192 compounds of formula IA wherein R1 and R2 together represent the ring fragment (CH2)4, Y1-Y2-Y3 is —C=N—S—, A2 is CH, A3 is CH, A4 is CH, and R5b, n, R3 and R4 are as defined in Table Q.

Table 307

Table 307 provides 192 compounds of formula IA wherein R1 and R2 together represent the ring fragment (CH2)5, Y1-Y2-Y3 is —C=N—S—, A2 is CH, A3 is CH, A4 is CH, and R5b, n, R3 and R4 are as defined in Table Q.

Table 308

Table 308 provides 192 compounds of formula IA wherein R1 and R2 together represent the ring fragment (CH2)2O (CH2)2, Y1-Y2-Y3 is —C=N—S—, A2 is CH, A3 is CH, A4 is CH, and R5b, n, R3 and R4 are as defined in Table Q.

Table 309

Table 309 provides 192 compounds of formula IA wherein R1 and R2 together represent the ring fragment (CH2)3, Y1-Y2-Y3 is —C=CH—S—, A2 is CH, A3 is CH, A4 is CH, and R5b, n, R3 and R4 are as defined in Table Q.

Table 310

Table 310 provides 192 compounds of formula IA wherein R1 and R2 together represent the ring fragment (CH2)4, Y1-Y2-Y3 is —C=CH—S—, A2 is CH, A3 is CH, A4 is CH, and R5b, n, R3 and R4 are as defined in Table Q.

Table 311

Table 311 provides 192 compounds of formula IA wherein R1 and R2 together represent the ring fragment (CH2)5, Y1-Y2-Y3 is —C=CH—S—, A2 is CH, A3 is CH, A4 is CH, and R5b, n, R3 and R4 are as defined in Table Q.

Table 312

Table 312 provides 192 compounds of formula IA wherein R1 and R2 together represent the ring fragment (CH2)2O (CH2)2, Y1-Y2-Y3 is —C=CH—S—, A2 is CH, A3 is CH, A4 is CH, and R5b, n, R3 and R4 are as defined in Table Q.

Compounds of formula I include at least one chiral centre and may exist as compounds of formula I* or compounds of formula I**.

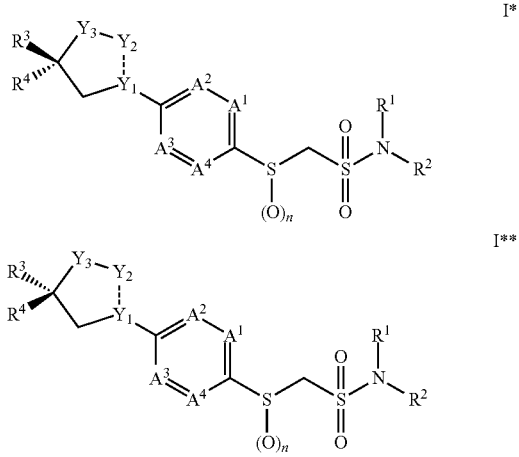

Generally compounds of formula I** are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I** compared to the total amount of both enantiomers is for example greater than 50%, e.g. at least 55, 60, 65, 70, 75, 80, 85, 90, 95, 96, 97, 98, or at least 99%. Likewise, in enantiomerically (or epimerically) enriched mixture of formula I*, the molar proportion of the compound of formula I* compared to the total amount of both enantiomers (or epimerically) is for example greater than 50%, e.g. at least 55, 60, 65, 70, 75, 80, 85, 90, 95, 96, 97, 98, or at least 99%. Enantiomerically (or epimerically) enriched mixtures of formula I** are preferred. Each compound disclosed in Tables 1 to 312 represents a specific disclosure of a compound according to formula I*, as well as a specific disclosure of a compound according to formula I**.

Compounds of formula Int-I include at least one chiral centre and may exist as compounds of formula Int-I* or compounds of formula Int-I**.

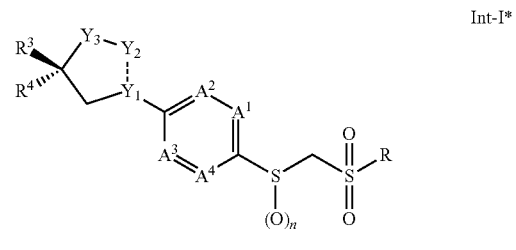

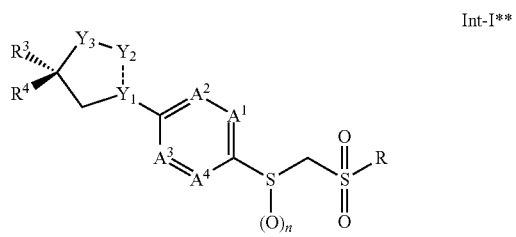

The invention includes mixtures of compounds Int-I* and Int-I in any ratio e.g. in a molar ratio of 1:99 to 99:1, e.g. 10:1 to 1:10, e.g. a substantially 50:50 molar ratio. In an enantiomerically (or epimerically) enriched mixture of formula Int-I, the molar proportion of compound Int-I** compared to the total amount of both enantiomers is for example greater than 50%, e.g. at least 55, 60, 65, 70, 75, 80, 85, 90, 95, 96, 97, 98, or at least 99%. Likewise, in enantiomerically (or epimerically) enriched mixture of formula Int-I*, the molar proportion of the compound of formula Int-I* compared to the total amount of both enantiomers (or epimerically) is for example greater than 50%, e.g. at least 55, 60, 65, 70, 75, 80, 85, 90, 95, 96, 97, 98, or at least 99%. Enantiomerically (or epimerically) enriched mixtures of formula Int-I** are preferred.

The compounds of the invention may be made by a variety of methods as shown in the following Schemes.

Scheme 1

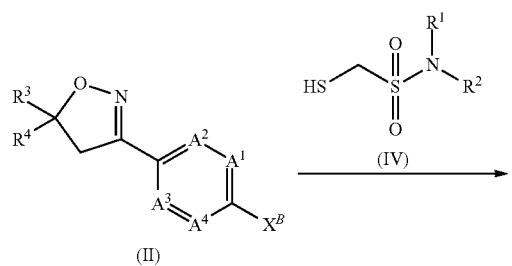
(II)

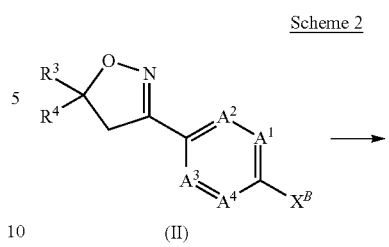
(IV)

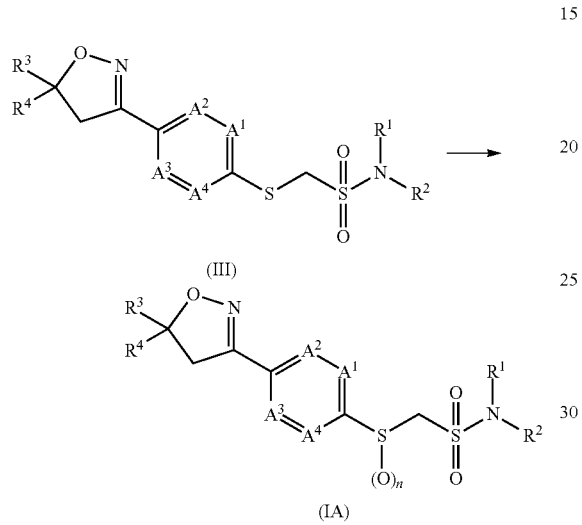
(III) → (IA)

Scheme 2

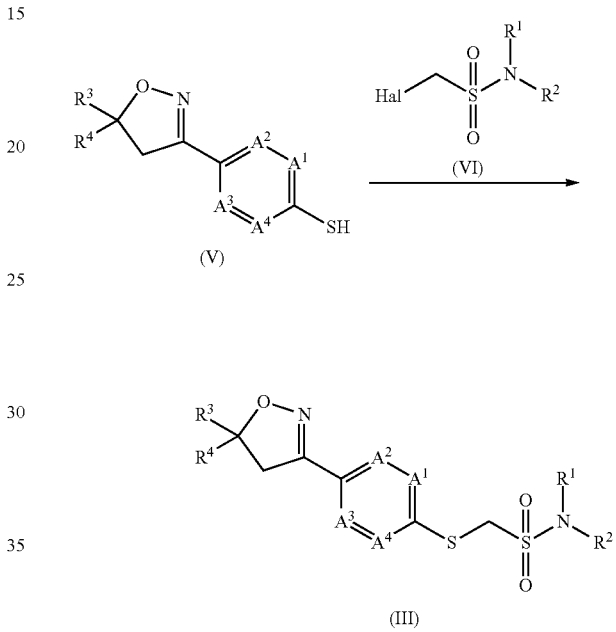

1) Compounds of formula (IA) wherein n is 1 or 2, can be prepared by oxidation of compound of formula (III). Such reactions can be carried out by treatment with an oxidising reagent, such as potassium permanganate, 3-chloroperoxybenzoic acid ("MCPBA"), sodium periodate/ruthenium(II) oxide, hydrogen peroxide, oxone and sodium hypochlorite. One equivalent of oxidising reagent is required to convent a sulfide to a sulfoxide, or a sulfoxide to a sulfone. Two equivalents of oxidising reagent are required to convent a sulfide to a sulfone. Preferred solvents are ethanol, methanol, tetrahydrofuran, dioxane, 1,2-dimethoxyethane, ethyl acetate, toluene, dichloromethane and water, or mixtures thereof. The reaction is optionally carried out in the presence of a base, for example a carbonate, such as sodium hydrogen carbonate. The reaction is carried out at a temperature of from 0° C. to 100° C., preferably from 15° C. to 30° C., in particular at ambient temperature.

2) Compounds of formula (III) can be prepared by reacting an intermediate of formula (II) wherein $X^B$ is a leaving group, for example a halogen, such as fluoro, chloro or bromo, with a mercaptan of formula (IV). Such reactions can be carried out in the presence of a base such as an amine or a carbonate, for example potassium or cesium carbonate in solvents such as acetonitrile, dimethylformamide, dimethylsulfoxide, dimethylacetamide at a temperature of from 0° C. to 150° C., preferably from 25° C. to 100° C.

3) Compounds of formula (II) can be obtained using a variety of methods, for example as described in WO09080250. Compounds of formula (IV) are either known compounds, such as 1-mercapto-metanesulfonamide (CAS 207517-20-2) or can be prepared using known methods by the person skilled in the art.

4) Alternatively, compounds of formula (III) can be prepared by alkylation of an intermediate of formula (V) with a reagent of formula (VI) wherein Hal is chloro, bromo, or iodo. Such reactions can be carried out according to well established methods, described for example in Journal of Medicinal Chemistry, 36(15), 2134-41; 1993. Compounds of formula (VI) are either known compounds, such as 1-chloro-methanesulfonamide (CAS 21335-43-3), or can be prepared by known methods to the person skilled in the art.

5) Compounds of formula (V) can be prepared by reaction of an intermediate of formula (II) wherein $X^B$ is a halogen, such as chloro, bromo, iodo and a transition metal catalyst, such as copper, nickel and palladium, a sulfur source such as sulfur, thiourea, and alkali thiosulfate. Such reactions can be carried out according to well established methods, described for example in U.S. 5338886 (Ni and thiourea), Tetrahedron Letters (2011), 52, 205-208 (palladium and thiourea) and Chinese Journal of Chemistry (2010), 28, 1441-1443 (copper and thioruea). Alternatively compounds of formula (VI) can be prepared by reaction of an intermediate of formula (II) wherein $X^B$ is a halogen, such as fluoro and chloro and an excess of alkali alkyl thiolate, such as sodium thiolate at a temperature between 50° C. and a 180° C. This reaction can be carried out, as described for example in Synthesis (1983), (9), 751-5.

Scheme 3

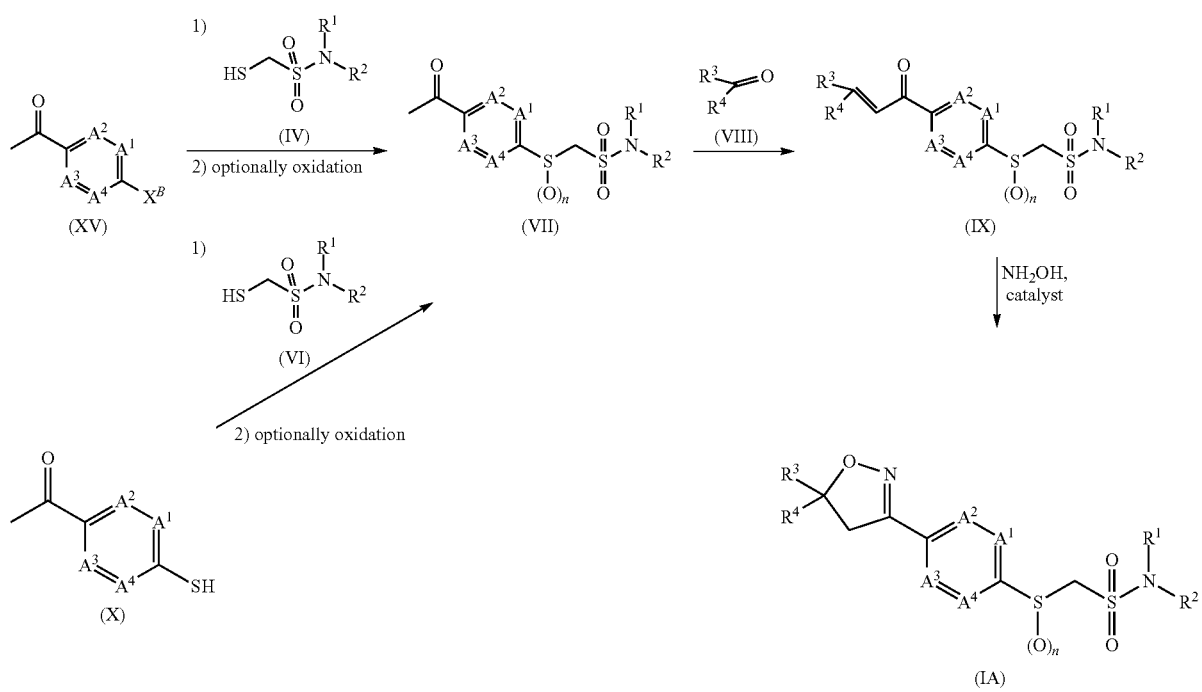

6) Compounds of formula (VII), which can be prepared according to the methods described in Schemes 1-2 from (XV) or (X), may be converted to compounds of formula (IX) by reaction with a ketone of formula (XVIII) according to methods described for example in WO2009/080250.

7) Subsequently, compounds of formula (IX) can be converted into compounds of formula (IA) by treatment with hydroxylamine, a base and a phase transfer catalyst, as described for example in WO09080250.

Scheme 4

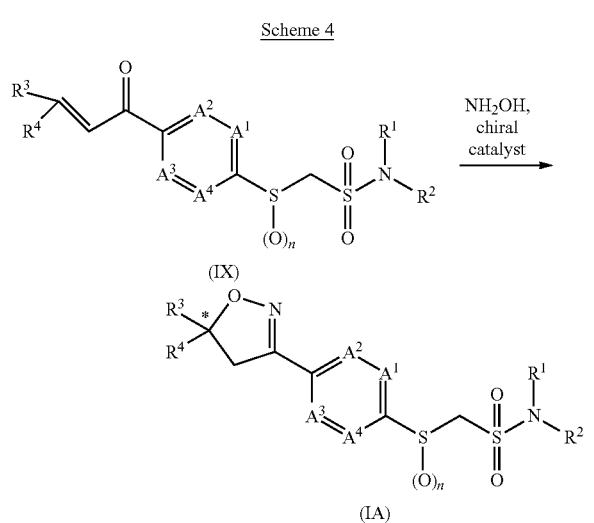

8) Compounds of formula (IA) can be obtained as an enantiomerically enriched mixture (the stereocentre indicated by *) either by chiral separation of the racemic compound or by use of a chiral catalyst in the as shown on Scheme 4. Such catalysts can for example be a chiral phase transfer catalyst, preferably a quinine derivative, for example a compound of formula XI.

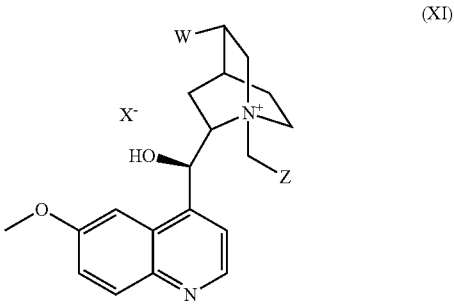

wherein Z is optionally substituted aryl or optionally substituted heteroaryl, W is ethyl or vinyl, and X is an anion, preferably a halogen anion, more preferably chloride or bromide. See for example WO2011/104089.

Scheme 5

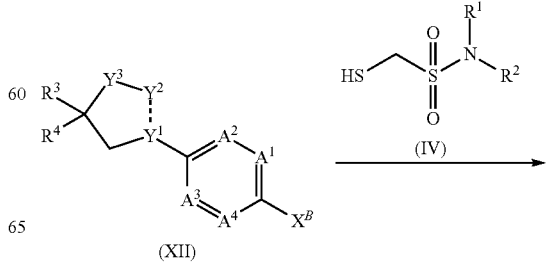

-continued

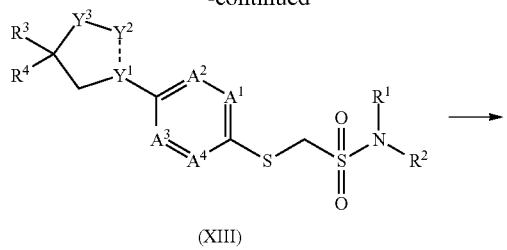

(XIII)

Scheme 6

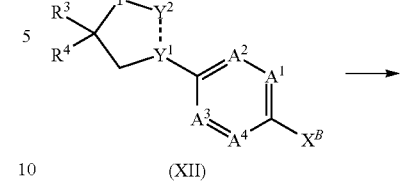

(XII)

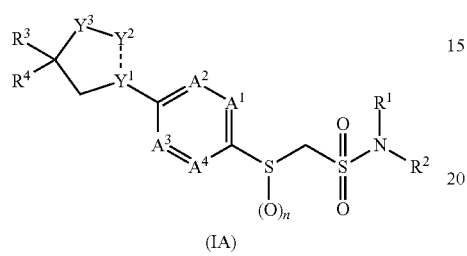

(IA)

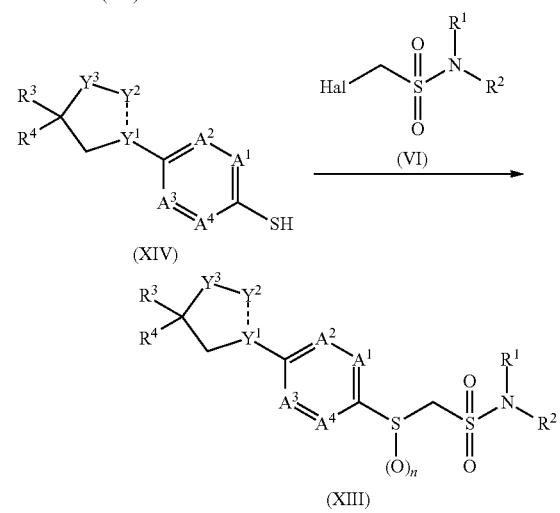

(XIV)

(XIII)

9) Compounds of formula (IA) wherein $Y_1$—$Y_2$—$Y_3$ is C=N—$CH_2$, C=N—S, C=CH—O, or N—$CH_2$—$CH_2$ can be similarly obtained as described on Scheme 5, using the same methods as those described under Scheme 1. See also WO2011/154555. Compounds of formula (XII) wherein $Y_1$--$Y_2$—$Y_3$ is C=N—$CH_2$ can be prepared for example as described in WO2009/072621. Compounds of formula (XII) wherein $Y_1$—$Y_2$—$Y_3$ is N—$CH_2$—$CH_2$ can be prepared for example as described in WO2008/128711. Compounds of formula (XII) wherein $Y_1$—$Y_2$—$Y_3$ is C=CH—O can be prepared for example as described in WO 2011101229.

10) Compounds of formula (XII) $Y_1$—$Y_2$—$Y_3$ is C=N—$CH_2$, C=CH—O, C=N—S, or N—$CH_2$—$CH_2$ may also be similarly converted into compounds of formula (XIII) as described on Scheme 6, using the same methods as those described under Scheme 2.

Scheme 7

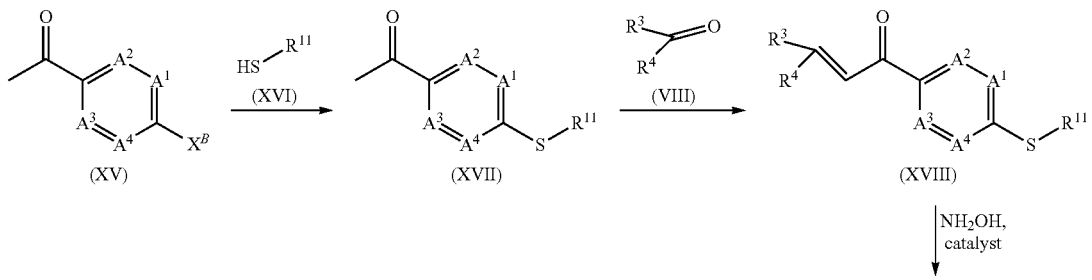

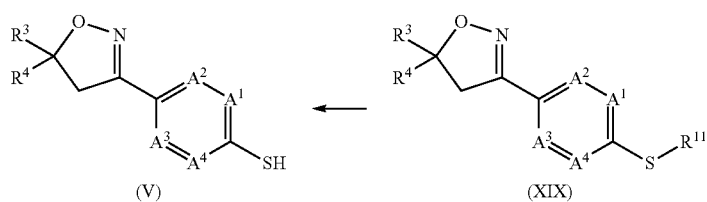

11) Compounds of formula (XVII) wherein $R^{11}$ is $C_1$-$C_6$alkyl or $C_1$-$C_6$alkyl optionally substituted by an aryl, can be prepared by reacting an intermediate of formula (XV) wherein $X^B$ is a leaving group, for example a halogen, such as fluoro, chloro or bromo, with a mercaptan of formula (XVI) wherein $R^{11}$ is $C_1$-$C_6$alkyl or $C_1$-$C_6$alkyl optionally substituted by an aryl, for example tert-butyl. Such reactions can be carried out in the presence of a base such as an amine or a carbonate, for example potassium or cesium carbonate in solvents such as acetonitrile, dimethylformamide, dimethylsulfoxide, dimethylacetamide at a temperature of from 0° C. to 150° C., preferably from 25° C. to 100° C. Examples of such reactions can be found in Synlett 2006, 8, 1255-1259, and specific examples are described in the experimental section. Alternatively, the reaction can be carried out in the presence of a catalyst, for a example a palladium catalyst, and a ligand, for example a phosphine ligand in a solvent such as tetrahydrofuran, dioxane, 1,2-dimethoxyethane, ethyl acetate, or toluene at a temperature of from 0° C. to 150° C., preferably from 80° C. to 130° C. This reaction can be carried out under microwave irradiation, as described for example in WO2007/102059, and specific examples are described in the experimental section.

12) Compounds of formula (XVII) wherein $R^{11}$ is $C_1$-$C_6$alkyl or $C_1$-$C_6$alkly optionally substituted by an aryl, may be converted to compounds of formula (XVIII) wherein $R^{11}$ is $C_1$-$C_6$alkyl or $C_1$-$C_6$alkyl optionally substituted by an aryl, by reaction with a ketone of formula (VIII) according to methods described for example in WO2009/080250.

13) Subsequently, compounds of formula (XVIII) wherein $R^{11}$ is $C_1$-$C_6$alkyl or $C_1$-$C_6$alkyl optionally substituted by an aryl, can be converted into compounds of formula (XIX) wherein $R^{11}$ is $C_1$-$C_6$alky or $C_1$-$C_6$alky optionally substituted by an aryl, by treatment with hydroxylamine, a base and a phase transfer catalyst, as described for example in WO2009/080250.

14) Subsequently, compounds of formula (XIX) wherein $R^{11}$ is $C_1$-$C_6$alkyl or $C_1$-$C_6$alkyl optionally substituted by an aryl, can be converted into compounds of formula (V). Such reactions can be carried out in the presence of an acid, e.g. a Lewis acid such as an sulfonic acid, carboxylic acid for example methylsulfonic acid, paratoluenesulfonic acid, trifluoroacetic acid, aluminum trichloride or mercury(II) acetate in solvents such as acetic acid, trifluoroacetic acid, toluene, dichloromethane, water, at a temperature of from −78° C. to 150° C., preferably from 0° C. to 110° C. Examples of such reactions can be found in Organometallics, 2007, 26, 897-909 and Chemical Communications 2009, 5236-5238, and specific examples are described in the experimental section.

Scheme 8

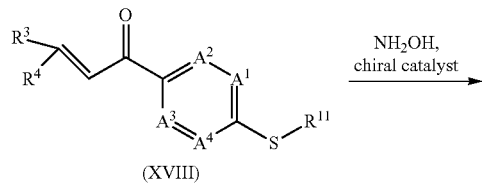

(XVIII)

15) Compounds of formula (XVIII) wherein $R^{11}$ is $C_1$-$C_6$alkyl or $C_1$-$C_6$alkyl optionally substituted by an aryl, can be converted into compounds of formula (XIX) e.g. stereoselectively (the stereocentre indicated by *) wherein $R^{11}$ is $C_1$-$C_6$alkyl or $C_1$-$C_6$alkyl optionally substituted by an aryl, by treatment with hydroxylamine, a base and a phase transfer catalyst, as described for example in WO2009/080250.

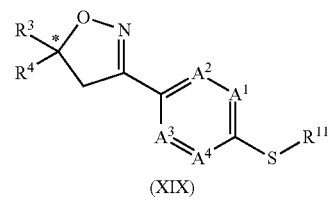

Scheme 9

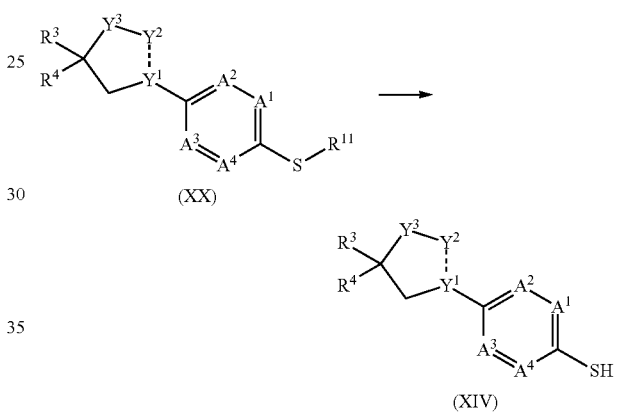

16) Compounds of formula (XX) wherein $Y_1$—$Y_2$—$Y_3$ is C=N—$CH_2$, C=CH—O, C=N—S, or N—$CH_2$—$CH_2$ may also be similarly converted into compounds of formula (XIV) as described under Scheme 9, using the same methods as those described under Scheme 2.

Scheme 10

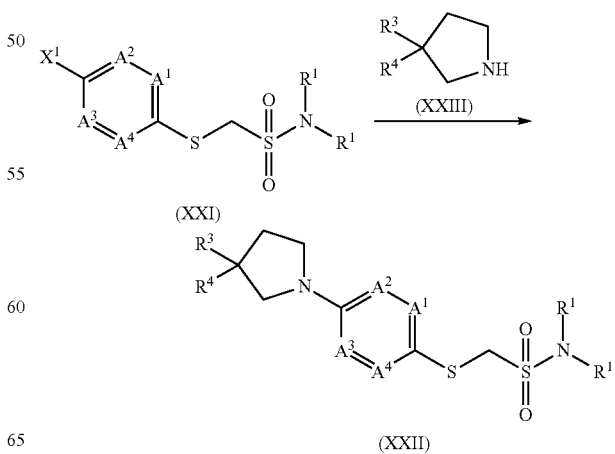

17) Compounds of formula (XXI) wherein $X^1$ is halogen such as, chloro, bromo, or iodo, or a sulfonate ester such as triflate or mesylate may also be similarly converted into compounds of formula (XXII) as described under Scheme 10 by reaction of a pyrrolidine of formula (XXIII) in presence of a base, such as alkali metal alkoxide, alkali phosphate or alkali carbonate, and a palladium or copper catalyst. The reaction is carried out at a temperature of from 0° C. to 200° C., preferably from 20° C. to 160° C. The equivalents of base use can vary from 0.1 to 10 equivalents, preferably from 1 to 4 equivalents.

Scheme 11

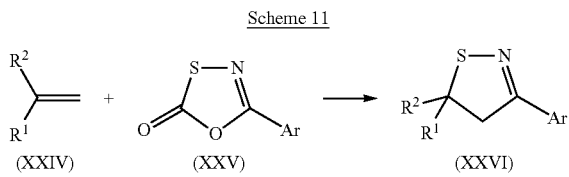

(XXIV)    (XXV)    (XXVI)

In scheme 11 and following schemes, Ar stands for group Ar1 or group Ar2 or group Ar3 or group Ar4

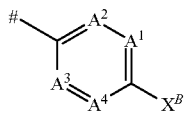

(Ar4)

18) Compounds of formula (XXVI) can be prepared by reacting a compound of formula (XXV) with the vinyl compound of formula (XXIV) optionally in the presence of a suitable solvent, for example N,N-dimethylformamide, xylene, toluene, chlorobenzene or dichlorobenzene. The reaction can be performed under microwave heating preferably at temperatures up to 200° C. and preferably under neat conditions using a large excess of the compound of formula XXIV (e.g. 40 equivalents). Vinyl compounds of formula (XXIV) are commercially available or can be made by methods known to a person skilled in the art. Compounds of formula (XXV) can be made by methods known to a person skilled in the art, as described for example in Journal of Organic Chemistry (1981), 46(4), 771.

Scheme 12

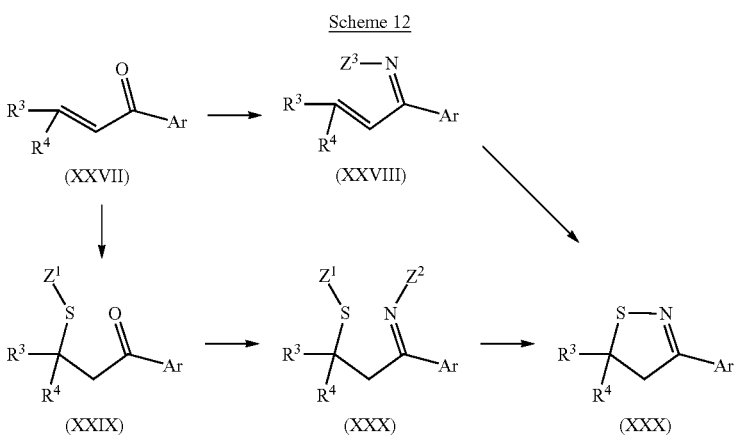

(XXVII)    (XXVIII)

(XXIX)    (XXX)    (XXX)

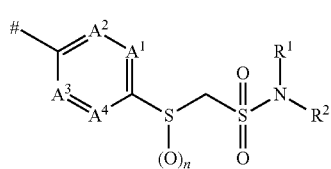

(Ar1)

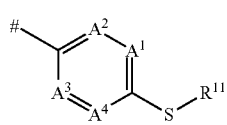

(Ar2)

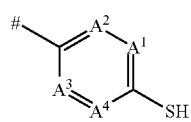

(Ar3)

19) Compounds of formula (XXIX) wherein Ar is as defined under Scheme 11 and $R^3$ and $R^4$ are as defined for compounds (I) and $Z^1$ is hydrogen, halogen, cyano, $C_1$-$C_8$alkyl, aryl-$C_1$-$C_4$alkylene-, $C_1$-$C_8$alkylcarbonyl-, arylsulfonyl- or arylthio-, can be obtained by reacting an unsaturated ketone of formula (XXVII) with a sulfur nucleophile, such as thioacetic acid, hydrogen sulfide, sodium sulfide, ammonium sulfide, thiourea, benzylmercaptan, sodium benzenethiosulfonate, sodium thiomethoxide or tert-butyl mercaptan. Such reactions can be performed optionally in the presence of a base, such as sodium hydroxide, sodium ethoxide, sodium methoxide, sodium tert-butoxide or potassium hydroxide. Such reations can also be performed in the presence of an acid, for example p-toluenesulfonic acid, hydrochloric acid, acetic acid, in a solvent, such as methanol, ethanol, N,N-dimethylformamide, toluene, dichloromethane, ethyl acetate, acetonitrile or chlorobenzene or water, or mixtures thereof, at a temperature of from 0° C. to 100° C., preferably from ambient temperature to 80° C. Such conditions are described, for example, in Journal of the American Chemical Society (1949), 71, 3554-5 or in Tetrahedron: Asymmetry (2003), 14(1), 113-117 and Journal of Organic Chemistry (1996), 61, 1986.

20) Compounds of formula (XXVIII) wherein Ar is as defined under Scheme 11 and $R^3$ and $R^4$ are as defined for compounds (I) and $Z^3$ is thiol or aryl substituted $C_1$-$C_8$alkylsulfinyl-, can be made by reaction of the ketone of formula (XXVII) with an amine, such as triphenylmethanesulfenamide. Such reactions are usually carried out in the presence of an acid, for example p-toluenesulfonic acid, hydrochloric acid, acetic acid, optionally in the presence of a solvent, for example an alcohol, such as methanol or ethanol, or toluene, dichloromethane, water, or mixtures thereof. The reaction can be carried our in the presence or the absence of a dehydrating agent, such as anhydrous magnesium sulfate or molecular sieves. It can also be perfomed using a Dean Stark or Soxhlet apparatus that enables a constant removal of the water formed during the reaction. The reaction is carried out at a temperature of from 0° C. to 100° C., preferably from 15° C. to 30° C., in particular at ambient temperature.

21) Compounds of formula (XXX) wherein Ar is as defined under Scheme 11 and $R^3$ and $R^4$ are as defined for compounds (I) and $Z^2$ is hydrogen or hydroxyl or $C_1$-$C_8$alkoxy- or $C_1$-$C_8$alkylsulfonyloxy- or $C_1$-$C_8$arylsulfonyloxy- or aryl-$C_1$-$C_4$alkylene-or aryl, can be made by reaction of the ketone of formula (XXIX) with an amine, such as hydroxylamine hydrochloride, methoxylamine or ammonia. Such reactions are carried out in the presence of a base, for example an organic base, such as triethylamine or sodium acetate, or an inorganic base, such as sodium hydrogen carbonate, optionally in the presence of a solvent, for example an alcohol, such as methanol or ethanol, or water, or mixtures thereof. Such reactions can also be carried out in the presence of an acid or not, for example p-toluenesulfonic acid, hydrochloric acid, acetic acid, optionnally in the presence of a solvent, for example an alcohol, such as methanol or ethanol, or toluene, dichloromethane, water, or mixtures thereof. The reaction can be carried our in the presence or the absence of a dehydrating agent, such as anhydrous magnesium sulfate or molecular sieves. It can also be perfomed using a Dean Stark or Soxhlet apparatus that enables a constant removal of the water formed during the reaction. The reaction is carried out at a temperature of from 0° C. to 100° C., preferably from 15° C. to 30° C., in particular at ambient temperature.

22) Compounds of formula (XXVI) can be obtained by cyclising a compound of formula (XXVI) wherein $Z^3$ is thiol. Such reactions are usually carried out in the presence of an acid or not, for example p-toluenesulfonic acid, optionnally in the presence of a solvent, for example dichloroethane, methanol, ethanol, toluene, dichloromethane or chlorobenzene.The reaction is carried out at a temperature of from 0° C. to 200° C., preferably from 25° C. to 100° C. Alternatively, compounds of formula (XXVI) can be obtained by cyclising a compound of formula (XXVIII) wherein $Z^3$ is aryl substituted $C_1$-$C_8$alkylsulfinyl-. Such reactions are usually carried out in the presence of an acid or not, for example p-toluenesulfonic acid, trifluoroacetic acid or hydrochloric acid, optionnally in the presence of a solvent, for example dichloroethane, methanol, ethanol, toluene, dichloromethane or chlorobenzene.The reaction is carried out at a temperature of from 0° C. to 200° C., preferably from 25° C. to 100° C. Such reactions usually involve first the deprotection of the thiol to give a compound of formula (XXVIII) wherein $Z^3$ is thiol, followed by the cyclization.

23) Compounds of formula (XXVI) can be obtained from compound of formula (XXX) wherein $Z^1$ is hydrogen or $C_1$-$C_8$alkyl or aryl-$C_1$-$C_4$alkylene-or $C_1$-$C_8$alkylcarbonyl- or arylsulfonyl- or arylthio-, and $Z^2$ is hydrogen or hydroxyl or $C_1$-$C_8$alkoxy- or $C_1$-$C_8$alkylsulfonyloxy- or $C_1$-$C_8$arylsulfonyloxy- or aryl-$C_1$-$C_4$alkylene-or aryl. Such reactions usually involve the deprotection of $Z^1$ and of $Z^2$ or of both groups. The reaction can then involve the following intermediates:

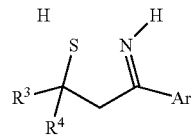

(XXXa)

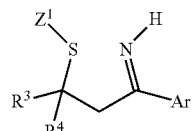

(XXXb)

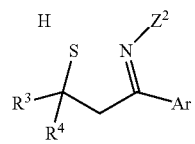

(XXXc)

Depending on the nature of $Z^1$ and $Z^2$, the deprotection conditions are different and can be made by methods known to a person skilled in the art or as described in T. W. Green, P. G. M. Wuts, *Protective Groups in Organic Synthesis*, Wiley-Interscience, New York, 1999, 564-566, 740-743.

24) Compounds of formula (XXVI) can be obtained from compound of formula (XXXa) from an oxidation reaction. Such reactions are usually carried out in the presence of an oxidant, for example iodine, bromine, thionyl chloride, Bis(trifluoroacetoxy)iodobenzene; The reaction can be carried our in the presence of an acid, such as trifluoroacetic acid or acetic acid, optionnally in the presence of a solvent, for example dichloroethane, dimethylsulfoxide, N,N-dimethylformamide, methanol, ethanol, toluene, dichloromethane, ethyl acetate or chlorobenzene. The reaction is carried out at a temperature of from 0° C. to 200° C., preferably from 25° C. to 100° C. Such transformations, including reaction conditions and suitable catalyst, are described in Journal of the Chemical Society, Perkin Transactions 1: Organic and Bio-Organic Chemistry (1972-1999) (1985), (1), 153-7 and Organic Letters (2006), 8(21), 4811-4813. Similarly, compounds of formula (XXVI) can be obtained from a compound of formula (XXXb) wherein $Z^1$ is arylsulfonyl- or arylthio-, by an oxidation reaction as described in Journal of Organic Chemistry (1990), 55(13), 4156-62.

25) Compounds of formula (XXVI) can be obtained from compound of formula (XXXc) wherein $Z^2$ is $C_1$-$C_8$alkoxy-. Such reactions are usually carried out in the presence of a copper (I) reagent, such copper-3-methylsalicylate. The reaction can be carried out in the presence of a solvent, for example dichloroethane, dimethylsulfoxide, N,N-dimethylformamide, methanol, ethanol, toluene, dichloromethane, ethyl acetate or chlorobenzene. The reaction is carried out at a temperature of from 0° C. to 200° C., preferably from 25° C. to 100° C., or under microwave heating conditions. Such transformations are described in Journal of the American Chemical Society (2011), 133, 6403-6410.

26) Alternatively, compounds of formula (XXVI) can be obtained directly from a compound of formula (XXIX)

wherein $Z^1$ is hydrogen. Such reactions are usually carried out in the presence chloramines formed in situ from ammonia and chlorine or sodium hypochlorite or hypochlorous acid, optionally in the presence of a solvent, for example dichloroethane, methanol, ethanol, toluene, dichloromethane or chlorobenzene. The reaction is carried out at a temperature of from −80° C. to 40° C., preferably below −40° C.

27) Alternatively, compounds of formula (XXVI) can be obtained directly from a compound of formula (XXIX) wherein $Z^1$ is halogen, cyano, arylsulfonyl- or arylthio-. Such reactions are usually carried out in the presence ammonia, optionally in the presence of a solvent, for example dichloroethane, tetrahydrofuran, methanol, ethanol, toluene, dichloromethane or chlorobenzene. The reaction is carried out at a temperature of from −80° C. to 80° C.

28) Alternatively, compounds of formula (XXVI) can be obtained directly from a compound of formula (XXIX) wherein $Z^1$ is aryl-$C_1$-$C_4$alkylene. Such reactions are usually carried out in two steps. The first step involves the treatment of a compound of formula (XXIX) wherein $Z^1$ is aryl-$C_1$-$C_4$alkylene with a suitable oxidant, such as sulfuryl chloride or chlorine, in the presence of a solvent, for example dichloroethane, methanol, ethanol, toluene, dichloromethane or chlorobenzene, to provide a compound of formula (XXIX) wherein $Z^1$ is chlorine. The second step then involves the treatment a compound of formula (XXIX) wherein $Z^1$ is chlorine by an ammonia source, such as ammonia or ammonium bromide in the presence of a base, in the presence of a solvent, for example dichloroethane, methanol, ethanol, toluene, tetrahydrofuran, dichloromethane or chlorobenzene. Both steps are usually carried out at a temperature of from −80° C. to 80° C.

29) Alternatively, compounds of formula (XXVI) can be obtained directly from a compound of formula (XXIX) wherein $Z^1$ is hydrogen. Such reactions are usually carried out in the presence of a suitable nitrogen electrophile, such as hydroxylamine-O-sulfonic acid. Such reactions are carried out in the presence of a base, for example an organic base, such as triethylamine or sodium acetate, or an inorganic base, such as sodium hydrogen carbonate, sodium hydroxide or potassium hydroxide optionally in the presence of a solvent, for example tetrahydrofuran, toluene, an alcohol, such as methanol or ethanol, or water, or mixtures thereof. The reaction is carried out at a temperature of from −80° C. to 80° C.

Scheme 13

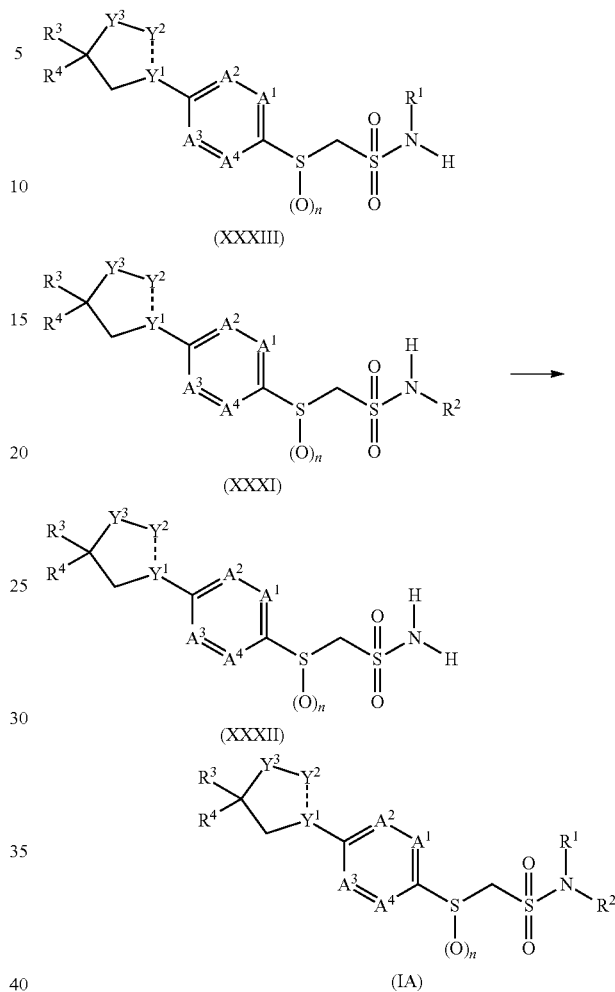

30) Compounds of formula (IA) can be obtained from compounds of formula (XXXI), (XXXII), or (XXXIII) as shown on Scheme 13 by standard methods, for example by alkylation with an electrophilic reagent $R^2$-Hal, Scheme 14

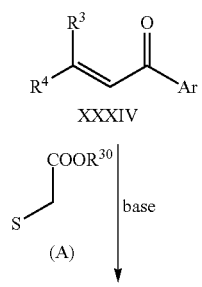

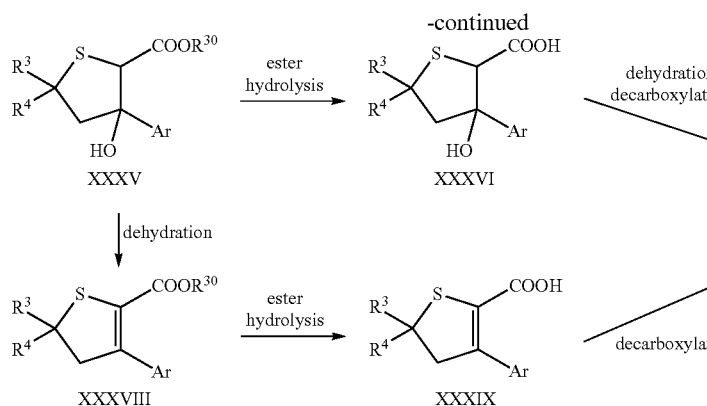

31) Compounds of formula (XXXVII) wherein Ar is as defined under Scheme 11 and R³ and R⁴ are as defined for compounds (I) can be obtained by reacting an unsaturated ketone of formula (XXXIV) with a sulfur nucleophile such as thioglycolate of type (A) wherein $R^{3o}$ is $C_1$-$C_{15}$ alkyl or aryl in presence or absence of a base such as sodium hydroxide, sodium ethoxide, sodium methoxide, sodium tert-butoxide or potassium hydroxide in a solvent, such as, acetonitrile, tetrahydrofuran, 1,4-dioxane, toluene, dichloromethane, N,N-dimethylformamide, or chlorobenzene or water, or mixtures thereof, at a temperature of from 0° C. to 100° C., preferably from ambient temperature to 80° C. Such conditions are described, for example, in European Journal of Medicinal Chemistry (1992), 27, 633-9, to obtain compound of formula XXXV. From compound XXXV the target molecule can be prepared by any of the two sequence via XXXIX or via XXXVI (as shown in scheme 14). In one sequence where compound of formulat XXXV can be dehydrated first to obtain compound of formula XXXVIII which can then be put into standard ester hydrolysis condition known to person expert in the art to obtain compound of formula XXXIX. This compound can then be subjected to decarboxylation under conditions like thermal heating or heating in presence of a base to get compound of formula XXXVII. On the other hand compound of formula can also be converted to compound XXXVII in a two step procedure, first by hydrolysis the ester under standard hydrolytic conditions to obtain compound of formula XXXVI followed by single step dehydrative decarboxylation using sulphonyl chlorides first followed by heating the crude isolated material to obtain the compound of formula XXXVII.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the compounsd of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The compounds of the invention may be used for example on turf, ornamentals, such as flowers, shrubs, broad-leaved trees or evergreens, for example conifers, as well as for tree injection, pest management and the like. Compositions comprising the compound of formula I may be used on ornamental garden plants (e.g. flowers, shrubs, broad-leaved trees or evergreens), e.g. to control aphids, whitefly, scales, meelybug, beetles and caterpillars. Compositions comprising the compound of formula I may be used on garden plants (e.g. flowers, shrubs, broad-leaved trees or evergreens), on indoor plants (e.g. flowers and shrubs) and on indoor pest e.g. to control aphids, whitefly, scales, meelybug, beetles and caterpillars.

Furthermore, the compounds of the invention may be effective against harmful insects, without substantially imposing any harmful side effects to cultivated plants. Application of the compounds of the invention may increase the harvest yields, and may improve the quality of the harvested material. The compounds of the invention may have favourable properties with respect to amount appled, residue formulation, selectivity, toxicity, production methodology, high activity, wide spectrum of control, safety, control of resistant organisms, e.g. pests that are resistant to organic phosphorus agents and/or carbamate agents.

Examples of pest species which may be controlled by the compounds of formula (I) include: coleopterans, for example, Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica spp., Monochamus alternatus, Lissorhoptrus oryzophilus, Lyctus bruneus, Aulacophora femoralis; lepidopterans, for example, Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella; hemipterans, for example, Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara spp., Trialeurodes vaporariorm, Psylla spp.; thysanopterans, for example, Thrips palmi, Franklinella occidental; orthopterans, for example, Blatella germanica, Periplaneta americana, Gryllotalpa Africana, Locusta migratoria migratoriodes; isopterans, for example, Reticulitermes speratus, Coptotermes formosanus; dipterans, for example, Musca domestica, Aedes aegypti, Hylemia platura, Culex pipiens, Anopheles sinensis, Culex tritaeniorhynchus, Liriomyza trifolii; acari, for example, Tetranychus cinnabarinus, Tetranychus urticae, Panonychus citri, Aculops pelekassi, Tarsonemus spp.; nematodes, for example, Meloidogyne incognita, Bursaphelenchus lignicolus Mamiya et Kiyohara, Aphelenchoides besseyi, Heterodera glycines, Pratylenchus spp.

Examples of further pest species which may be controlled by the compounds of formula (I) include: from the order of the Anoplura (Phthiraptera), for example, *Damalinia* spp., *Haematopinus* spp., *Linognathus* spp., *Pediculus* spp., *Trichodectes* spp.; from the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*; from the class of the Bivalva, for example, *Dreissena* spp.; from the order of the Chilopoda, for example, *Geophilus* spp., *Scutigera* spp.; from the order of the Coleoptera, for example, *Acanthoscehdes obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.; from the order of the Collembola, for example, *Onychiurus armatus*; from the order of the Dermaptera, for example, *Forficula auricularia*; from the order of the Diplopoda, for example, *Blaniulus guttulatus*; from the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.; from the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp, *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*; ft may be furthermore possible to control protozoa, such as *Eimeria*; from the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.; from the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pini, Aphis* spp., *Arboridia apicalis, Aspidiella* spp., *Aspidiotus* spp., *Atanus* spp., *Aulaconthum solani, Bemisia* spp., *Brachycaudus helichrysii, Brachycolus* spp., *Brevicoryne brassicae, Calligypona manginata, Canneocephala fulgida, Ceratovacuna lanigena, Cercopidae, Cenoplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeunodes* spp., *Diaphorina* spp., *Diaspis* spp., *Dorsalis* spp., *Drosicha* spp., *Dysaphis* spp., *Dysmicoccus* spp., *Empoasca* spp., *Eniosoma* spp., *Erythnoneuna* spp., *Euscelis bilobatus, Geococcus coffeae, Homalodisca coagulata, Hyaloptenus arundinis, Icerya* spp., *Idiocenus* spp., *Idioscopus* spp., *Laodelphax stniatellus, Lecanium* spp., *Lepidosaphes* spp., *Lipaphis erysimi, Macnosiphum* spp., *Mahanarva fimbriolata, Melanaphis sacchari, Metcalfiella* spp., *Metopolophium dinhodum, Monellia costalis, Monelliopsis pecanis, Myzus* spp., *Nasonovia ribisnigri, Nephotettix* spp., *Nilaparvata lugens, Oncometopia* spp., *Onthezia pnaelonga, Panabemisia mynicae, Paratrioza* spp., *Panlatonia* spp., *Pemphigus* spp., *Peregrinus maidis, Phenacoccus* spp., *Phloeomyzus passeninii, Phorodon humuli, Phylloxera* spp., *Pinnaspis aspidistrae, Planococcus* spp., *Protopulvinania pyriformis, Pseudaulacaspis pentagona, Pseudococcus* spp., *Psylla* spp., *Ptenomalus* spp., *Pynilla* spp., *Quadnaspidiotus* spp., *Quesada gigas, Rastrococcus* spp., *Rhopalosiphum* spp., *Saissetia* spp., *Scaphoides titanus, Schizaphis graminum, Selenaspidus anticulatus, Sogata* spp., *Sogatella furcifera, Sogatodes* spp., *Stictocephala festina, Tenalaphana malayensis, Tinocallis caryaefoliae, Tomaspis* spp., *Toxoptera* spp., *Tnialeunodes vaporariorum, Trioza* spp., *Typhlocyba* spp., *Unaspis* spp., *Viteus vitifolii*; from the order of the Hymenoptera, for example, *Dipnion* spp., *Hoplocampa* spp., *Lasius* spp., *Mono-monium phanaonis, Vespa* spp.; from the order of the Isopoda, for example, *Armadillidium vulgane, Oniscus asellus, Poncellio scaben*; from the order of the Isoptena, for example, *Reticulitermes* spp., *Odontotermes* spp.; from the order of the Lepidoptera, for example, *Acronicta major, Aedia leucomelas, Agnotis* spp., *Alabama argillacea, Anticarsia* ssp., *Barathra brassicae, Bucculatrix thurberiella, Bupalus piniarius, Cacoecia podana, Capua*

*reticulana, Carpocapsa pomonella, Cheimatobia brumata, Chilo* ssp., *Choristoneura fumiferana, Clysia ambiguella, Cnaphalocerus* ssp., *Earias insulana, Ephestia kuehniella, Euproctis chrysorrhoea, Euxoa* ssp., *Feltia* ssp., *Galleria mellonella, Helicoverpa* ssp., *Heliothis* ssp., *Hofmannophila pseudospretella, Homona magnanima, Hyponomeuta padella, Laphygma* ssp., *Lithocolletis blancardella, Lithophane antennata, Loxagrotis albicosta, Lymantria* ssp., *Malacosoma neustria, Mamestra brassicae, Mocis repanda, Mythimna separata, Oria* ssp., *Oulema oryzae, Panolis flammea, Pectinophora gossypiella, Phyllocnistis citrella, Pieris* ssp., *Plutella xylostella, Prodenia* ssp., *Pseudaletia* ssp., *Pseudoplusia includens, Pyrausta nubilalis, Spodoptera* ssp., *Thermesia gemmatalis, Tinea pellionella, Tineola bisselliella, Tortrix viridana, Trichoplusia* ssp.; from the order of the Orthoptera, for example, *Acheta domesticus, Blatta orientalis, Blattella germanica, Gryllotalpa* ssp., *Leucophaea maderae, Locusta* ssp., *Melanoplus* ssp., *Periplaneta americana, Schistocerca gregaria*; from the order of the Siphonaptera, for example, *Ceratophyllus* ssp., *Xenopsylla cheopis*. From the order of the Symphyla, for example, *Scutigerella immaculata*; from the order of the Thysanoptera, for example, *Baliothrips biformis, Enneothrips flavens, Frankliniella* ssp., *Heliothrips* ssp., *Hercinothrips femoralis, Kakothrips* ssp., *Rhipiphorothrips cruentatus, Scirtothrips* ssp., *Taeniothrips cardamoni, Thrips* ssp.; from the order of the Thysanura, for example, *Lepisma saccharina*. The phytoparasitic nematodes include, for example, *Anguina* ssp., *Aphelenchoides* ssp., *Belonoaimus* ssp., *Bursaphelenchus* ssp., *Ditylenchus dipsaci, Globodera* ssp., *Heliocotylenchus* ssp., *Heterodera* ssp., *Longidorus* ssp., *Meloidogyne* ssp., *Pratylenchus* ssp., *Radopholus similis, Rotylenchus* ssp., *Trichodorus* ssp., *Tylenchorhynchus* ssp., *Tylenchulus* ssp., *Tylenchulus semipenetrans, Xiphinema* ssp.

In particular, the compounds of the invention may be used to control the following pest spcies:

*Myzus persicae* (aphid), *Aphis gossypii* (aphid), *Aphis fabae* (aphid), *Lygus* ssp. (capsids), *Dysdercus* ssp. (capsids), *Nilaparvata lugens* (planthopper), *Nephotettixc incticeps* (leafhopper), *Nezara* ssp. (stinkbugs), *Euschistus* ssp. (stinkbugs), *Leptocorisa* ssp. (stinkbugs), *Frankliniella occidentalis* (thrip), *Thrips* ssp. (thrips), *Leptinotarsa decemlineata* (Colorado potato beetle), *Anthonomus grandis* (boll weevil), *Aonidiella* ssp. (scale insects), *Trialeurodes* ssp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* ssp. (cutworms), *Chilo suppressalis* (rice stem borer), *Locusta* migratoria (locust), *Chortiocetes terminifera* (locust), *Diabrotica* ssp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* ssp. (flat mites), *Boophilus microplus* (cattle tick), *Dermacentor variabilis* (American dog tick), *Ctenocephalides felis* (cat flea), *Liriomyza* ssp. (leafminer), *Musca domestica* (housefly), *Aedes aegypti* (mosquito), *Anopheles* ssp. (mosquitoes), *Culex* ssp. (mosquitoes), *Lucillia* ssp. (blowflies), *Blattella germanica* (cockroach), *Periplaneta americana* (cockroach), *Blatta orientalis* (cockroach), termites of the Mastotermitidae (for example *Mastotermes* ssp.), the Kalotermitidae (for example *Neotermes* ssp.), the Rhinotermitidae (for example *Coptotermes formosanus, Reticulitermes flavipes, R. speratu, R. virginicus, R. hesperus*, and *R. santonensis*) and the Termitidae (for example *Globitermes sulfureus*), *Solenopsis geminata* (fire ant), *Monomorium pharaonis* (pharaoh's ant), *Damalinia* ssp. and *Linognathus* ssp. (biting and sucking lice), *Meloidogyne* ssp. (root knot nematodes), *Globodera* ssp. and *Heterodera* ssp. (cyst nematodes), *Pratylenchus* ssp. (lesion nematodes), *Rhodopholus* ssp. (banana burrowing nematodes), *Tylenchulus* ssp.(citrus nematodes), *Haemonchus contortus* (barber pole worm), *Caenorhabditis elegans* (vinegar eelworm), *Trichostrongylus* ssp. (gastro intestinal nematodes) and *Deroceras reticulatum* (slug).

The compound of formula I may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some 15 cases 30-150 g/ha), citrus (e.g. in some cases 60-200 g/ha), almonds (e.g. in some cases 40-180 g/ha), fruiting vegetables, cucurbits and pulses (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used for pest control on various plants, including soybean, corn, sugarcane, alfalfa, brassicas, oilseed rape (e.g. canola), potatoes (including sweet potatoes), cotton, rice, coffee, citrus, almonds, fruiting vegetables, cucurbits and pulses (e.g. tomatoes, pepper, chili, eggplant, cucumber, squash etc.), tea, bulb vegetables (e.g. onion, leek etc.), grapes, pome fruit (e.g. apples, pears etc.), stone fruit (e.g. pears, plums etc.), and cereals.

The compounds of the invention may be used on soybean to control, for example, *Elasmopalpus lignosellus, Diloboderus abderus, Diabrotica speciosa, Trialeurodes* ssp., *Bemisia* ssp., aphids, *Sternechus subsignatus, Formicidae, Agrotis ypsilon, Julus* ssp., *Murgantia* ssp., *Halyomorpha* ssp., *Thyanta* ssp., *Megascelis* ssp., *Procornitermes* ssp., *Gryllotalpidae, Nezara viridula, Piezodorus* ssp., *Acrosternum* ssp., *Neomegalotomus* ssp., *Cerotoma trifurcata, Popillia japonica, Edessa* ssp., *Liogenys fuscus, Euschistus heros, stalk borer, Scaptocoris castanea, phyllophaga* ssp., *Migdolus* ssp., *Pseudoplusia includens, Anticarsia gemmatalis, Epinotia* ssp., *Rachiplusia* ssp., *Spodoptera* ssp., *Bemisia tabaci, Tetranychus* ssp., *Agriotes* ssp., *Euschistus* ssp. The compounds of the invention are preferably used on soybean to control *Diloboderus abderus, Diabrotica speciosa, Trialeurodes* ssp., *Bemisia* ssp., *Nezara viridula, Piezodorus* ssp., *Acrosternum* ssp., *Cerotoma trifurcata, Popillia japonica, Euschistus heros, Scaptocoris castanea, phyllophaga* ssp., *Migdolus* ssp., *Agriotes* ssp., *Euschistus* ssp.

The compounds of the invention may be used on corn to control, for example, *Euschistus heros, Euschistus* ssp., *Dichelops furcatus, Diloboderus abderus, Thyanta* ssp., *Elasmopalpus lignosellus, Halyomorpha* ssp., *Spodoptera frugiperda, Nezara viridula, Cerotoma trifurcata, Popillia japonica, Agrotis ypsilon, Diabrotica speciosa*, aphids, Heteroptera, *Procornitermes* ssp., *Scaptocoris castanea, Formicidae, Julus* ssp., *Dalbulus maidis, Diabrotica virgifera, Diabrotica* ssp., *Mocis latipes, Bemisia tabaci, heliothis* ssp., *Tetranychus* ssp., *thrips* ssp., *phyllophaga* ssp., *Migdolus* ssp., *scaptocoris* ssp., *Liogenys fuscus*, *Spodoptera* ssp., *Ostrinia* ssp., *Sesamia* ssp., wireworms, *Agriotes* ssp., *Halotydeus destructor*. The compounds of the invention are preferably used on corn to control *Euschistus heros*, *Euschistus* ssp., *Dichelops furcatus*, *Diloboderus abderus*, *Nezara viridula*, *Cerotoma trifurcata*, *Popillia japonica*, *Diabrotica speciosa*, *Diabrotica virgifera*, *Diabrotica* ssp., *Tetranychus* ssp., *Thrips* ssp., *Phyllophaga* ssp., *Migdolus* ssp., *Scaptocoris* ssp., *Agriotes* ssp.

The compounds of the invention may be used on sugar cane to control, for example, *Sphenophorus* ssp., termites, *Migdolus* ssp., *Diloboderus* ssp., *Telchin licus*, *Diatrea saccharalis*, *Mahanarva* ssp., Mealybugs.

The compounds of the invention may be used on alfalfa to control, for example, *Hypera brunneipennis*, *Hypera postica*, *Colias eurytheme*, *Collops* ssp., *Empoasca solana*, *Epitrix* ssp., *Geocoris* ssp., *Lygus hesperus*, *Lygus lineolaris*, *Spissistilus* ssp., *Spodoptera* ssp., Aphids, *Trichoplusia ni*. The compounds of the invention are preferably used on alfalfa to control *Hypera brunneipennis*, *Hypera postica*, *Empoasca solana*, *Epitrix* ssp., *Lygus hesperus*, *Lygus lineolaris*, *Trichoplusia ni*.

The compounds of the invention may be used on brassicas to control, for example, *Plutella xylostella*, *Pieris* ssp., *Mamestra* ssp., *Plusia* ssp., *Trichoplusia ni*, *Phyllotreta* ssp., *Spodoptera* ssp., *Empoasca* ssp., *thrips* ssp., *Delia* ssp., *Murgantia* ssp., *Trialeurodes* ssp., *Bemisia* ssp., *Microtheca* ssp., *Aphids*.The compounds of the invention are preferably used on brassicas to control *Plutella xylostella*, *Pieris* ssp., *Plusia* ssp., *Trichoplusia ni*, *Phyllotreta* ssp., *Thrips* ssp.

The compounds of the invention may be used on oil seed rape, e.g. canola, to control, for example, *Meligethes* ssp., *Ceutorhynchus napi*, *Halotydeus destructor*, *Psylloides* ssp.

The compounds of the invention may be used on potatoes, including sweet potatoes, to control, for example, *Empoasca* ssp., *Leptinotarsa* ssp., *Diabrotica speciosa*, *Phthorimaea* ssp., *Paratrioza* ssp., *Maladera matrida*, *Agriotes* ssp., Aphids, wireworms. The compounds of the invention are preferably used on potatoes, including sweet potatoes, to control *Empoasca* ssp., *Leptinotarsa* ssp., *Diabrotica speciosa*, *Phthorimaea* ssp., *Paratrioza* ssp., *Agriotes* ssp.

The compounds of the invention may be used on cotton to control, for example, *Anthonomus grandis*, *Pectinophora* ssp., *heliothis* ssp., *Spodoptera* ssp., *Tetranychus* ssp., *Empoasca* ssp., *Thrips* ssp., *Bemisia tabaci*, *Trialeurodes* ssp., Aphids, *Lygus* ssp., *phyllophaga* ssp., *Scaptocoris* ssp., *Austroasca viridigrisea*, *Creontiades* ssp., *Nezara* ssp., *Piezodorus* ssp., *Halotydeus destructor*, *Oxycaraenus hyalinipennis*, *Dysdercus cingulatus*. The compounds of the invention are preferably used on cotton to control *Anthonomus grandis*, *Tetranychus* ssp., *Empoasca* ssp., *thrips* ssp., *Lygus* ssp., *phyllophaga* ssp., *Scaptocoris* ssp.

The compounds of the invention may be used on rice to control, for example, *Leptocorisa* ssp., *Cnaphalocrosis* ssp., *Chilo* ssp., *Scirpophaga* ssp., *Lissorhoptrus* ssp., *Oebalus pugnax*, *Scotinophara* ssp., *Nephotettix malayanus*, *Nephotettix nigropictus*, *Nephotettix parvus*, *Nephottetix virescens*, *Nephotettix* ssp., Mealybugs, *Sogatella furcifera*, *Nilaparvata lugens*, *Orseolia* ssp., *Cnaphalocrocis medinalis*, *Marasmia* ssp., *Stenchaetothrips biformis*, *Thrips* ssp., *Hydrellia philippina*, Grasshoppers, *Pomacea canaliculata*, *Scirpophaga innotata*, *Chilo suppressalis*, *Chilo auricilius*, *Chilo polychrysus*, *Sesamia inferens*, *Laodelphax striatellus*, *Nymphula depunctalis*, *Oulema oryzae*, Stinkbugs. The compounds of the invention are preferably used on rice to control *Leptocorisa* ssp., *Lissorhoptrus* ssp., *Oebalus pugnax*, *Nephotettix malayanus*, *Nephotettix nigropictus*, *Nephotettix parvus*, *Nephottetix virescens*, *Nephotettix* ssp., *Sogatella furcifera*, *Stenchaetothrips biformis*, *Thrips* ssp., *Hydrellia philippina*, Grasshoppers, *Pomacea canaliculata*, *Scirpophaga innotata*, *Chilo suppressalis*, *Chilo polychrysus*, *Oulema oryzae*.

The compounds of the invention may be used on coffee to control, for example, *Hypothenemus Hampei*, *Perileucoptera Coffeella*, *Tetranychus* ssp., *Brevipalpus* ssp., Mealybugs. The compounds of the invention are preferably used on coffee to control *Hypothenemus Hampei*, *Perileucoptera Coffeella*.

The compounds of the invention may be used on citrus to control, for example, *Panonychus citri*, *Phyllocoptruta oleivora*, *Brevipalpus* ssp., *Diaphorina citri*, *Scirtothrips* ssp., *Thrips* ssp., *Unaspis* ssp., *Ceratitis capitata*, *Phyllocnistis* ssp., Aphids, Hardscales, Softscales, Mealybugs. The compounds of the invention are preferably used on citrus to control *Panonychus citri*, *Phyllocoptruta oleivora*, *Brevipalpus* ssp., *Diaphorina citri*, *Scirtothrips* ssp., *thrips* ssp., *Phyllocnistis* ssp.

The compounds of the invention may be used on almonds to control, for example, *Amyelois transitella*, *Tetranychus* ssp.

The compounds of the invention may be used on fruiting vegetables, cucurbits and pulses, including tomatoes, pepper, chili, eggplant, cucumber, squash etc., to control, for example, *Thrips* ssp., *Tetranychus* ssp., *Polyphagotarsonemus* ssp., *Aculops* ssp., *Empoasca* ssp., *Spodoptera* ssp., *heliothis* ssp., *Tuta absoluta*, *Liriomyza* ssp., *Bernisia tabaci*, *Trialeurodes* ssp., Aphids, *Paratrioza* ssp., *Frankliniella occidentalis*, *Frankliniella* ssp., *Anthonomus* ssp., *Phyllotreta* ssp., *Amrasca* ssp., *Epilachna* ssp., *Halyomorpha* ssp., *Scirtothrips* ssp., *Leucinodes* ssp., *Neoleucinodes* ssp. *Maruca* ssp., Fruit flies, Stinkbugs, Lepidopteras, Coleopteras. The compounds of the invention are preferably used on fruiting vegetables, cucurbits and pulses, including tomatoes, pepper, chili, eggplant, cucumber, squash etc., to control *Thrips* ssp., *Tetranychus* ssp., *Polyphagotarsonemus* ssp., *Aculops* ssp., *Empoasca* ssp., *Spodoptera* ssp., *heliothis* ssp., *Tuta absoluta*, *Liriomyza* ssp., *Paratrioza* ssp., *Frankliniella occidentalis*, *Frankliniella* ssp., *Amrasca* ssp., *Scirtothrips* ssp., *Leucinodes* ssp., *Neoleucinodes* ssp.

The compounds of the invention may be used on tea to control, for example, *Pseudaulacaspis* ssp., *Empoasca* ssp., *Scirtothrips* ssp., *Caloptilia theivora*, *Tetranychus* ssp. The compounds of the invention are preferably used on tea to control *Empoasca* ssp., *Scirtothrips* ssp.

The compounds of the invention may be used on bulb vegetables, including onion, leek etc. to control, for example, *Thrips* ssp., *Spodoptera* ssp., *heliothis* ssp. The compounds of the invention are preferably used on bulb vegetables, including onion, leek etc. to control *Thrips* ssp.

The compounds of the invention may be used on grapes to control, for example, *Empoasca* ssp., *Lobesia* ssp., *Eupoecilia ambiguella*, *Frankliniella* ssp., *Thrips* ssp., *Tetranychus* spp., *Rhipiphorothrips Cruentatus*, *Eotetranychus Willamettei*, *Erythroneura Elegantula*, *Scaphoides* spp., *Scelodonta strigicollis*, Mealybugs. The compounds of the invention are preferably used on grapes to control *Frankliniella* spp., *Thrips* spp., *Tetranychus* spp., *Rhipiphorothrips Cruentatus*, *Scaphoides* spp.

The compounds of the invention may be used on pome fruit, including apples, pears etc., to control, for example, *Cacopsylla* spp., *Psylla* spp., *Panonychus ulmi*, *Cydia pomonella*, Lepidopteras, Aphids, Hardscales, Softscales.

The compounds of the invention are preferably used on pome fruit, including apples, pears etc., to control *acopsylla* spp., *Psylla* spp., *Panonychus ulmi*.

The compounds of the invention may be used on stone fruit to control, for example, *Grapholita molesta, Scirtothrips* spp., *Thrips* spp., *Frankliniella* spp., *Tetranychus* spp., Aphids, Hardscales, Softscales, Mealybugs. The compounds of the invention are preferably used on stone fruit to control *Scirtothrips* spp., *Thrips* spp., *Frankliniella* spp., *Tetranychus* spp.

The compounds of the invention may be used on cereals to control, for example, Aphids, Stinkbugs, earthmites, *Eurygaster integriceps, Zabrus tenebrioides, Anisoplia austriaca, Chaetocnema aridula, Phyllotreta* spp., *Oulema melanopus, Oscinella* spp., *Delia* spp., *Mayetiola* spp., *Contarinia* spp., *Cephus* spp., *Steneotarsonemus* spp., *Apamea* spp.

In another embodiment compounds of formula I and mixtures of the invention may be used on rice to control *Baliothrips biformis* (Thrips), *Chilo* spp. (e.g. *Chilo polychrysus* (Dark headed striped borer), *Chilo suppressalis* (Rice stemborer), *Chilo indicus* (Paddy stem borer), *Chilo polychrysus* (Dark-headed rice borer), *Chilo suppressalis* (Stripe stem borer)), *Cnaphalocrocis medinalis* (Rice leaf folder), *Dicladispa armigera* (Hispa), *Hydrellia philipina* (Rice whorl-maggot), *Laodelphax* spp. (Smaller brown planthopper) (e.g. *Laodelphax striatellus*), *Lema oryzae* (Rice leafbeetle), *Leptocorsia acuta* (Rice bug), *Leptocorsia oratorius* (rice bug), *Lissorhoptrus oryzophilus* (rice water weevil), *Mythemina separata* (armyworm), *Nephottetix* spp. (Green leafhopper) (e.g. *Nephotettix cincticeps, Nephotettix malayanus, Nephotettix nigropictus, Nephotettix parvus, Nephottetix virescens*), *Nilaparvata lugens* (Brown Planthopper), *Nymphula depunctalis* (Rice caseworm), *Orseolia oryzae* (Rice Gall midge), *Oulema oryzae* (Rice leafbeetle), *Scirpophaga incertulas* (Yellow Stemborer), *Scirpophaga innotata* (White Stemborer), *Scotinophara coarctata* (Rice black bug), *Sogaella frucifera* (White-backed planthopper), *Steneotarsonemus spinki*.

The compounds of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers, Leafminers (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, Thrips, Tip moths, Tussock moth larvae, Wasps, Broadmites, Brown softscales, California redscales (crawlers), Clover mites, Mealybugs, Pineneedlescales (crawlers), Spider mites, Whiteflies The compounds of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The compounds of formula (I) and mixture of the invention, in particular those in the tables above, may be used for soil applications, including as a seed application, to target at least the following: sucking pests such as aphids, thrips, brown plant hopper (e.g. on rice), sting bugs, white flies (e.g. on cotton and vegetables), mites; on soil pests such as corn root worm, wireworms, white grubs, zabrus, termites (e.g. on sugar cane, soy, pasture), maggots, cabbage root fly, red legged earth mite; on lepidoptera, such as spodoptera, cutworms, *elasmoplpus, plutella* (e.g. brassica), stem borers, leaf miners, flea beetle, *Sternechus*; on nematicides, such as *Heterodera glycines* (e.g. on soybean), *Pratylenchus brachyurus* (e.g. on corn), *P. zeae* (e.g. oncorn), *P. penetrans* (e.g. on corn), *Meloidogyne incognita* (e.g. on vegetables), *Heterodera schachtii* (e.g. on sugar beet), *Rotylenchus reniformis* (e.g. on cotton), *Heterodera avenae* (e.g. on cereals), *Pratylenchus neglectus* (e.g. on cereals), *thornei* (e.g. on cereals).

The compounds of formula (I) and mixture of the invention, in particular those in the tables above may be used for seed applications at least on the following: soil grubs for corn, soybeans, sugarcane: *Migdolus* spp; *Phyllophaga* spp.; *Diloboderus* spp; *Cyclocephala* spp; *Lyogenys fuscus*; sugarcane weevils: *Sphenophorus levis & Metamasius hemtpterus*; termites for soybeans, sugarcane, pasture, others: *Heterotermes tenuis; Heterotermes longiceps; Cornitermes cumulans; Procornitermes triacifer; Neocapritermes opacus; Neocapritermes parvus*; corn root worms for corn and potatoes: *Diabrotica* spp., seed Maggot: *Delia platura*; soil stinkbugs: *Scaptocoris castanea*; wireworms: *Agriotes* spp; *Athous* spp *Hipnodes bicolor; Ctenicera destructor; Limonius canu; Limonius californicus*; rice water weevil: *Lissorhoptrus oryzophilus*; Red Legged earth mites: *Halotydeus destructor*.

The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees. Crops are to be understood as also including those crops which have been rendered tolerant to herbicides or classes of herbicides (e.g. ALS—, GS—, EPSPS—, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

The compounds of the invention may be applied to plant parts. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

Compounds of formula I may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in super-additive ("synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A.105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (corn producing Cry1Ab), Agrisure®RW (corn producing mCry3A), Agrisure® Viptera (corn hybrids producing Vip3Aa); Agrisure300GT (corn hybrids producing Cry1Ab and mCry3A); YieldGard® (corn hybrids producing the Cry1Ab protein), YieldGard® Plus (corn hybrids producing Cry1Ab and Cry3Bb1), Genuity® SmartStax® (corn hybrids with Cry1A.105, Cry2Ab2, Cry1F, Cry34/35, Cry3Bb); Herculex® I (corn hybrids producing Cry1Fa) and Herculex®RW (corn hybrids producing Cry34Ab1, Cry35Ab1 and the enzyme Phosphinothricin-N-Acetyltransferase [PAT]); NuCOTN®33B (cotton cultivars producing Cry1Ac), Bollgard®I (cotton cultivars producing Cry1Ac), Bollgard®II (cotton cultivars producing Cry1Ac and Cry2Ab2) and VIPCOT® (cotton cultivars producing a Vip3Aa). Soybean Cyst Nematode resistance soybean (SCN®–Syngenta) and soybean with Aphid resistant trait (AMT®) are also of interest.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (Ostrinia nubilalis and Sesamia nonagrioides) by transgenic expression of a truncated Cry1A(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603 x MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603 8 MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4D (e.g. Enlist®) (e.g. WO 2011066384), glyphosate (e.g. Roundup Ready®, Roundup Ready 2 Yield®), sulfonylurea (e.g. STS®), glufosinate (e.g. Liberty Link®, Ignite®), Dicamba (Monsanto), HPPD tolerance (e.g. isoxaflutole herbicide) (Bayer CropScience, Syngenta). Double or triple stacks of any of the traits described here are also of interest, including glyphosate and sulfonyl-urea tolerance ((e.g. Optimum GAT®), plants stacked with STS® and Roundup Ready® or plants stacked with STS® and Roundup Ready 2 Yield®), dicamba and glyphosate tolerance (Monsanto). Of particular interest are soybean plants carrying trains conferring resistance to 2.4D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto).

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

Examples of cotton transgenic events include MON 531/757/1076 (Bollgard I®–Monsanto), MON1445 (Roundup ready cotton®–Monsanto), MON531×MON1445 (Bollgard I+RR®–Monsanto), MON15985 (Genuity Bollgard II cotton®–Monsanto), MON88913 (Genuity RR FLEX cotton®–Monsanto), MON15985×MON1445 (Genuity Bollgard II+RR FELX cotton®–Monsanto), MON15983× MON88913 (Genuity Bollgard II+RR FLEX cotton®–Monsanto), MON15985 (FibreMax Bollgard II Cotton®–Monsanto), LL25 (FibreMax LL cotton®–BCS Stoneville), GHB614 (FibreMax GlyTol cotton®–BCS Stoneville), LL25×MON15985 (FibreMax LL Bollgard II cotton®–BCS Stoneville/Monsanto), GHB614×LL25 (FibreMax LL GlyTol cotton®–BCS Stoneville), GHB614×LL25× MON15985 (FibreMax RR GlyTol Bollgard II cotton®–BCS Stoneville), MON88913×MON15985 (FibreMax LL GlyTol Bollgard II cotton®–Monsanto), MON88913 (FibreMax RR Flex cotton®–Monsanto), GHB119+T304-40 (Twinlink®–BCS Stoneville), GHB119+T304-40×LL25× GHB614 (Twinlink LL GT®–BCS Stoneville), 3006-210-23×281-24-236 (PhytoGen Widestrike Insect Protection®–Dow), 3006-210-23×281-24-236×MON88913 (PhytoGen Widestrike Insect Protection+RR FLEX-® Dow/Monsanto), 3006-210-23×281-24-236×MON1445 ((PhytoGen Widestrike Insect Protection+RR®–Dow/Monsanto), MON1445 (PhytoGen Roundup Ready®–Monsanto), MON88913 (PhytoGen Roundup Ready FLEX®–Monsanto), COT102×COT67B (Vipcot®–Syngenta), COT102× COT67B×MON88913 (Vipcot RR FLEX®–Syngenta/Monsanto), 281-24-236 (Dow), 3006-210-23 (Dow), COT102 (Syngenta), COT67B (Syngenta), T304-40 (BCS Stoneville).

Examples of Soy transgenic events include MON87701× MON89788 (Genuity Roundup ready 2 Yield soybeans®–Monsanto), MON89788 (Roundup Ready2Yield®, RR2Y®–Monsanto), MON87708 (Monsanto), 40-3-2 (Roundup Ready®, RR1®–Monsanto), MON87701 (Monsanto), DAS-68416 (Enlist Weed Control System®–Dow), DP356043 (Optimum GAT®–Pioneer), A5547-127 (LibertyLink soybean®–Bayercropscience), A2704-12 (Bayercropscience), GU262 (Bayercropscience), W62 W98 (Bayercropscience), CRV127 (Cultivance®–BASF/EMBRAPA) SYHT0H2 (WO2012/082548).

Examples of Maize transgenic events include T25 (LibertyLink®, LL®–Bayerscropscience), DHT-1 (Dow), TC1507 (Herculex I®–Dow), DAS59122-7 (Herculex RW®–Dow), TC1507+DAS59122-7–Herculex Xtra®–Dow), TC1507×DAS-59122-7×NK603 (Herculex Xtra+ RR®–Dow), TC1507×DAS-59122-×MON88017× MON89034 (Genuity Smartstax corn®, Genuity Smartstax RIB complete®–Monsanto/Dow), MON89034×NK603 (Genuity VT double PRO®–Monsanto), MON89034+ MON88017 (Genuity VT Triple PRO®–Monsanto), NK603 (Roundup Ready2®, RR2®–Monsanto), MON810 (YieldGard BT®, Yieldgard cornborer®–Monsanto), MON810× NK603 (YieldGard cornborer RR Corn 200–Monasnto), MON810×MON863 (YieldGard Plus®–Monsanto), MON863×MON810×NK603 (YieldGard Plus+RR Corn2®/ YieldGard RR Maize®–Monsanto), MON863×NK603 (YieldGard Rotworm+RR Corn 2®–Monsanto), MON863 (YieldBard RW®–Monsanto), MON89034 (YieldGard RW®–Monsanto), MON88017 (YieldGard VT RW®–Monsanto), MON810+MON88017 (YieldGard VT Triple®–Monsanto), MON88017+MON89034 (YieldGard VT Triple Pro®–Monsanto), Bt11+MIR604+GA21 (Agrisure 3000®–

Syngenta), Btl 1+TC1507+MIR604+5307+GA21 (Syngenta), Bt11+TC1507+MIR604+DAS59122+GA21 (Agrisure 3122®–Syngenta), BT11 (Agrisure CB®–Syngenta), GA21–(Agrisure GT®–Syngenta), MIR604 (Agrisure RW®–Syngenta), Bt11+MIR162 (Agrisure TL VIP®–Syngenta), BT11+MIR162+GA21 (Agrisure Viptra 3110®–Syngenta), BT11+MIR162+MIR604 (Agrisure TM 3100®–Syngenta), Event3272+BT11+MIR604+GA21 (Syngenta), BT11+MIR1692+MIR604+GA21 (Agrisure Viptera 3111®–Syngenta), BT11+MIR 162+TC1507+GA21 (Agrisure Viptera 3220®–Syngenta), BT11+MIR162+TC1507+MIR604+5307+GA21 (Agrisure Viptera 3222®–Syngenta), MIR162 (Syngenta), BT11+GA21+MIR162+MIR604+5307 (Syngenta), 5307 (Syngenta).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1g to 1kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micro-nutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of suitable pesticides include the following
a) Pyrethroids, such as permethrin, cypermethrin, fenvalerate, esfenvalerate, deltamethrin, cyhalothrin (in particular lambda-cyhalothrin and gamma cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin, acrinathirin, etofenprox or 5-benzyl-3-furylmethyl-(E)-(1R,3S)-2,2-dimethyl-3-(2-oxothiolan-3-ylidenemethyl)cyclopropane carboxylate;
b) Organophosphates, such as profenofos, sulprofos, acephate, methyl parathion, azinphos-methyl, demeton-s-methy 1, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron, diafenthiuron, lufeneron, novaluron, noviflumuron or chlorfluazuron;

e) Organic tin compounds, such as cyhexatin, fenbutatin oxide or azocyclotin;
f) Pyrazoles, such as tebufenpyrad, tolfenpyrad, ethiprole, pyriprole, fipronil, and fenpyroximate;
g) Macrolides, such as avermectins or milbemycins, for example abamectin, emamectin benzoate, ivermectin, milbemycin, spinosad, azadirachtin, milbemectin, lepimectin or spinetoram;
h) Hormones or pheromones;
i) Organochlorine compounds, such as endosulfan (in particular alpha-endosulfan), benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds, such as imidacloprid, thiacloprid, acetamiprid, nitenpyram, dinotefuran, thiamethoxam, clothianidin, or nithiazine;
m) Diacylhydrazines, such as tebufenozide, chromafenozide or methoxyfenozide;
n) Diphenyl ethers, such as diofenolan or pyriproxifen;
o) Pyrazolines such as Indoxacarb or metaflumizone;
p) Ketoenols, such as Spirotetramat, spirodiclofen or spiromesifen;
q) Diamides, such as flubendiamide, chlorantraniliprole (Rynaxypyr®) or cyantraniliprole;
r) Essential oils such as Bugoil®—(PlantImpact); or
s) a comopund selected from buprofezine, flonicamid, acequinocy 1, bifenazate, cyenopyrafen, cyflumetofen, etoxazole, flometoquin, fluacrypyrim, fluensulfone, flufenerim, flupyradifuone, harpin, iodomethane, dodecadienol, pyridaben, pyridalyl, pyrimidifen, flupyradifurone, 4-[(6-Chloro-pyridin-3-ylmethyl)-(2,2-difluoro-ethyl)-amino]-5H-furan-2-one (DE 102006015467), CAS: 915972-17-7 (WO 2006129714; WO2011/147953; WO2011/147952), CAS: 26914-55-8 (WO 2007020986), chlorfenapyr, pymetrozine, sulfoxaflor and pyrifluqinazon.

In addition to the major chemical classes of pesticide listed above, other pesticides having particular targets may be employed in the composition, if appropriate for the intended utility of the composition. For instance, selective insecticides for particular crops, for example stemborer specific insecticide (combinations such as cartap) or hopper specific insecticides (combinations such as buprofezin) for use in rice may be employed. Alternatively insecticides or acaricides specific for particular insect species/stages may also be included in the compositions (for example acaricidal ovo-larvicides, to give combinations such as clofentezine, flubenzimine, hexythiazox or tetradifon; acaricidal motilicides, to give combinations such as dicofol or propargite ; acaricides, to give combinations such as bromopropylate or chlorobenzilate ; or growth regulators, such as hydramethylnon, cyromazine, methoprene, chlorfluazuron or diflubenzuron).

Examples of fungicidal compounds and combinations which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704) (e.g. acibenzolar-S-methyl), alanycarb, aldimorph, anilazine, azaconazole, azoxystrobin, benalaxyl, benomyl, benthiavalicarb, biloxazol, bitertanol, bixafen, blasticidin S, boscalid, bromuconazole, bupirimate, captafol, captan, carbendazim, carbendazim, chlorhydrate, carboxin, carpropamid, carvone, CGA41396, CGA41397, chinomethionate, chlorothalonil, chlorozolinate, clozylacon, copper containing compounds to give combintations such as copper oxychloride, copper oxyquinolate, copper sulfate, copper tallate and Bordeaux mixture, cyclufenamid, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimo 1, ethyl-(Z)-N-benzyl-N-qmethyl([methyl-thioethylideneamino oxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluopyram, fluoxastrobin, fluoroimide, fluquinconazole, flusilazole, flutolanil, flutriafol, fluxapyroxad, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, isopyrazam, kasugamycin, kresoxim-methyl, LY186054, LY211795, LY248908, mancozeb, mandipropamid, maneb, mefenoxam, metalaxyl, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, penflufen, penthiopyrad, phenazin oxide, phosetyl-Al, phosphorus acids, phthalide, picoxystrobin (ZA1963), polyoxinD, polyram, probenazole, prochloraz, procymidone, propamocarb, propiconazole, propineb, propionic acid, prothioconazole, pyrazophos, pyrifenox, pyrimethanil, pyraclostrobin, pyroquilon, pyroxyfur, pyrrolnitrin, quaternary ammonium compounds, quinomethionate, quinoxyfen, quintozene, sedaxane, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram, N-[9-(dichloromethylene)-1,2,3,4-tetrahydro-1,4-methanonaphthalen-5-yl]-3-(difluoromethyl)-1-methyl-1H-pyrazole-4-carboxamide [1072957-71-1], 1-methyl-3-difluoromethyl-1H-pyrazole-4-carboxylic acid (2-dichloromethylene-3-ethyl-1-methyl-indan-4-yl)-amide, and 1-methyl-3-difluoromethyl-4H-pyrazole-4-carboxylic acid [2-(2,4-dichloro-phenyl)-2-methoxy-1-methyl-ethyl]-amide.

The active ingredients combinations described above comprising a compound selected of the invention, in particulary from Tables 1 to 312 and an active ingredient as described above are preferably combined in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

In addition, biological agents may be included in the composition of the invention e.g. *Baciullus* species such as *Bacillus firmus, Bacillus cereus, Bacillus subtilis*, and *Pasteuria* species such as *Pasteuria penetrans* and *Pasteuria nishizawae*. A suitable *Bacillus firmus* strain is strain CNCM I-1582 which is commercially available as BioNem™. A suitable *Bacillus cereus* strain is strain CNCM 1-1562. Of both *Bacillus* strains more details can be found in U.S. Pat. No. 6,406,690. Other biological organisms that may be included in the compositions of the invention are bacteria such as *Streptomyces* spp. such as *S. avermitilis*, and fungi such as *Pochonia* spp. such as *P. chlamydosporia*. Also of interest are *Metarhizium* spp. such as *M. anisopliae*; *Pochonia* spp. such as *P. chlamydosporia*.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat, Nos. 5,478,855, 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta -cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, Buprofezine pyrimidifen, NC-1111, R-195,RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp aizawai, kurstaki, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following (where "Tx" means a compound of formula (I), and in particular a compound selected from Tables 1 to 312, which may result in a synergistic combination with the given active ingredient): imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide; more preferably, enrofloxacin, praziquantel, pyrantel 5 embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone; even more preferably enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

Examples of ratios of the compound of formula I to any mixing partner described herein include 15 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool), cultured fish, honeybees. By combating parasites, fatalities and performance reduction (in terms of meat, milk, wool, skins, eggs, etc.) 10 are reduced, so that applying the compounds of the invention allows more economic and simple husbandry of animals.

By controlling these pests it is intended to reduce deaths and improve performance (in the case of meat, milk, wool, hides, eggs, honey and the like) and health of the host animal. Also, controlling parasites may help to prevent the transmittance of infectious agents, the term "controlling" referring to the veterinary field, meaning that the active compounds are effective in reducing the incidence of the respective parasite in an animal infected with such parasites to innocuous levels, e.g. the active compound is effective in killing the respective parasite, inhibiting its growth, or inhibiting its proliferation.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc. and protozoae, such as coccidia).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria.*

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris.* Certain of these, such as *Nematodirus, Cooperia* and *Oesophagostomum* attack primarily the intestinal tract while others, such as *Haemonchus* and *Ostertagia,* are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma.*

Cestodes that are contemplated to be treated by the invention and by the inventive methods include, without limitation, the following genera: *Diphyllobothrium, Diplydium, Spirometra* and *Taenia.*

The most common genera of parasites of the gastrointestinal tract of humans are *Ancylostoma, Necator, Ascaris, Strongy hides, Trichinella, Capillaria, Trichuris* and *Enterobius.* Other medically important genera of parasites which are found in the blood or other tissues and organs outside the gastrointestinal tract are the filarial worms such as *Wuchereria, Brugia, Onchocerca* and *Loa,* as well as *Dracunculus* and extra intestinal stages of the intestinal worms *Strongyloides* and *Trichinella.*

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6$^{th}$Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans,* the horse fly or *Tabanus* spp., the stable fly or *Stomoxys calcitrans,* the black fly or *Simulium* spp., the deer fly or *Chrysops* spp., the louse fly or *Melophagus ovinus,* and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax,* the cattle grub or *Hypoderma* spp., the fleeceworm and the Gastrophilus of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi.*

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses 5 to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites, e.g. insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like. These include e.g. flies such as *Haematobia* (*Lyperosia*) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (Damalinia) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Examples of species of animal health pesets include those from the order of the *Anoplurida*, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus*; from the order of the *Mallophagida* and the suborders *Amblycerina* and *Ischnocerina*, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi*; from the order of the *Diptera* and the suborders *Nematocerina* and *Brachycerina*, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineaturn, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca*; from the order of the *Siphonapterida*, for example *Pulex* spp., *Ctenocephalides* spp., *Tunga* spp., *Xenopsylla* spp., *Ceratophyllusl* spp.; particular examples are: *Ctenocephalides canis, Ctenocephalides felis, Pulex irritans, Tunga penetrans, Xenopsylla cheopis*; from the order of the *Heteropterida*, for example *Cimex* spp., *Triatoma* spp., *Rhodnius* spp., *Panstrongylus* spp; from the order of the *Blattarida*, for example *Blatta orientalis, Periplaneta americana, Blattela germanica, Supella* spp. (e.g. *Suppella longipalpa*); from the subclass of the Acari (*Acarina*) and the orders of the Metaand Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni*; from the order of the Actinedida (*Prostigmata*) and *Acaridida* (*Astigmata*), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae* (*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi; Gasterophilus* spp., *Stomoxys* spp., *Trichodectes* spp., *Rhodnius* spp.,

*Ctenocephalides canis, Cimx lecturius, Ctenocephalides felis, Lucilia cuprina*; examples of acari include *Ornithodoros* spp., *Ixodes* spp., *Boophilus* spp.

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration; or by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection.

The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry.

These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such asBHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly adminstration intervals (i.e. administering the compounds to the animal once every month).

The Following Examples Illustrate, but do not Limit, the Invention.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm.

The following abbreviations were used in this section: DMF: dimethylformamide; THF: tetrahydrofuran; EtOAc: ethyl acetate; s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point; RT=retention time, $[M+H]^+$=molecular mass of the molecular cation, $[M-H]^-$=molecular mass of the molecular anion.

The following LC-MS methods were used to characterize the compounds:

| Method A | |
|---|---|
| MS | ACQUITY SQD Mass Spectrometer from Waters (Single quadrupole mass spectrometer) Ionisation method: Electrospray Polarity: positive ions Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700 Mass range: 100 to 800 Da DAD Wavelength range (nm): 210 to 400 |
| LC | Method Waters ACQUITY UPLC with the following HPLC gradient conditions (Solvent A: Water/Methanol 9:1, 0.1% formic acid and Solvent B: Acetonitrile, 0.1% formic acid) |

| Time (min) | A % | B % | Flow (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

| Method F | |
|---|---|
| CHIRAL HPLC | Alliance 2695 HPLC from Waters: solvent degasser, binary pump, heated column compartment and diode-array detector Column: Chiralpak IA, length (mm) 250, internal diameter (mm) 4.6, particle size (µ) 5, wavelength (nm): 270 nm, temperature (° C.) 30, solvent: Isocratic isopropyl alcohol: heptanes 10:90, injection volume 50 uL, flow (ml/min) 1. |

EXAMPLE 1

[2-bromo-4-[5-(3,5-dichlorophenyl)-5-(trifluoromethyl)-4H-isoxazol-3-yl]phenyl]sulfanylmethanesulfonamide

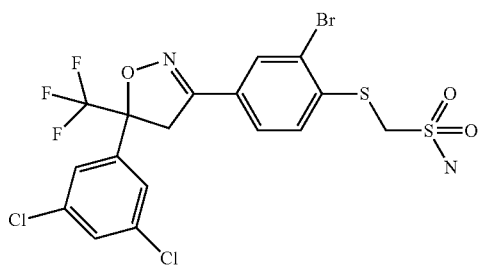 [SMILES: NS(=O)(=O)CSc1ccc(C2=NOC(c3cc(Cl)cc(Cl)c3)(C(F)(F)F)C2)cc1Br]

Step A: 1-(3-bromo-4-tert-butylsulfanyl-phenyl)ethanone

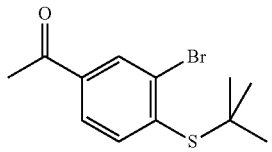

In a mechanically stirred reactor was charged dimethylformamide (350 mL), 1-(4-fluoro-3-bromo-phenyl)-ethanone (30 g), potassium carbonate (29 g) followed by tert-butylthiol (18.7 g). The resulting suspension was heated to 50° C. for 4 hours. The mixture was then cooled to room temperature and poured in brine (1 L), and the aqueous phase was extracted three times with ethyl acetate. The combined organic phases were washed with brine and dried over MgSO$_4$. The solvents were removed to leave the desired compound (40 g). LCMS (Method A) RT 1.11 min. [M+H]$^+$277-279. $^1$H NMR (400 MHz, CDCl$_3$) 1.40 (s, 9H), 2.59 (s, 3H), 7.70 (d, 1H), 7.71 (dd, 1H), 8.19 (d, 1H).

Step B: (E)-1-(3-bromo-4-tert-butylsulfanyl-phenyl)-3-(3,5-dichlorophenyl)-4,4,4-trifluoro-but-2-en-1-one

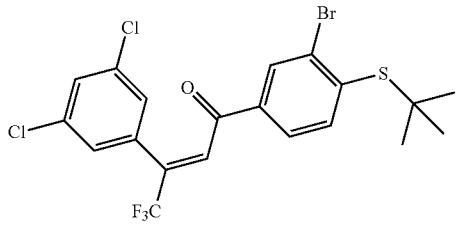 [SMILES: CC(C)(C)Sc1ccc(C(=O)/C=C(\c2cc(Cl)cc(Cl)c2)C(F)(F)F)cc1Br]

A suspension of 1-(bromo-4-tert-butylsulfanyl-phenyl) ethanone (Step A, 25.0 g), 1-(3,5-dichloro-phenyl)-2,2,2-trifluoro-ethanone (23.3 g), potassium carbonate (13.5 g), and triethylamine (1.2 ml) in 1,2-dichloroethane (500 ml), was heated at 85° C. for 16 hours. The reaction mixture was cooled to room temperature, partitioned between dichloromethane and water. The aqueous layer was separated, extracted with dichloromethane and the combined organic layers were dried over MgSO$_4$ and the solvent removed in vacuo. The residue (52.5 g) was purified by column chromatography on SiO$_2$ with heptane/EtOAc (95:5) to afford the title product (22.8 g) as a yellow solid. LCMS (Method A) RT 1.37 min, [M+OH]$^+$527/529/531; $^1$H-NMR (CDCl$_3$, 400 MHz): 1.39 (s, 9H), 7.10 (s, 2H), 7.37 (m, 2H), 7.64 (m, 2H), 8.01 (s, 1H). $^{19}$F-NMR (CDCl$_3$, 400 MHz): −67.2.

Step C: 3-(3-Bromo-4-tert-butylsulfanyl-phenyl)-5-(3,5-dichlorophenyl)-5-(trifluoromethyl)-4H-isoxazole

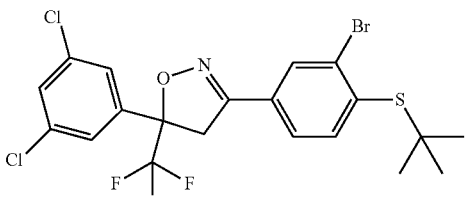

To a solution of (E)-1-(3-bromo-4-tert-butylsulfanyl-phenyl)-3-(3,5-dichlorophenyl)-4,4,4-trifluoro-but-2-en-1-one (prepared as described in Step B, 7.4 g) in 1,2-dichloroethane (37 ml) was added tetrabutylammonium bomide (1.4 g). The reaction mixture was cooled at 0° C. then hydroxylamine (50% 5 in water, 1.8 ml) and sodium hydroxide (15 g) were added simultaneously. The reaction was stirred 0° C. for 25 min and then brought back to room temperature. The mixture was diluted with water and extracted with dichloromethane several times; the combined organic layers were neutralized with 4N hydrochloric acid solution dried over MgSO$_4$ and the solvent evaporated under reduced pressure to obtain a solid, which was purified by column chromatography, eluted with heptane/EtOAc to afford the title product (4.2 g) as a colourless solid, which was used as such for the next step.

Step D: 2-bromo-4-[5-(3,5-dichlorophenyl)-5-(trifluoromethyl)-4H-isoxazol-3-yl]benzenethiol

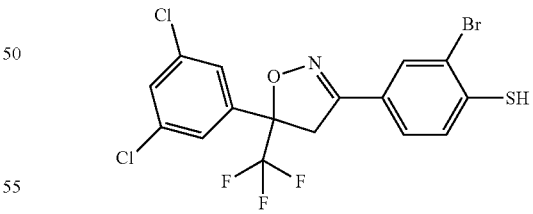

To a solution of 3-(3-bromo-4-tert-butylsulfanyl-phenyl)-5-(3,5-dichlorophenyl)-5-(trifluoromethyl)-4H-isoxazole (3.8 g) in toluene (19 mL) was added toluene-4-sulfonic acid (1.3 g) and the reaction was heated at a 110° C. overnight. The reaction was cooled down to room temperature and diluted in dichloromethane and washed with an aqueous saturated NaHCO$_3$ solution. The organic phase was dried over MgSO$_4$ and the solvents removed in vacuo to yield the crude product (5.3 g). The crude product was washed with hexane to yield the title compound as a solid (3.4 g). LCMS (Method A) RT 1.33 min, [M−H]⁻468/470/472; ¹H-NMR (CDCl₃, 400 MHz): 3.64 (d, 1H), 4.03 (d, 1H), 4.17 (s, 1H, SH), 7.39 (d, 1H), 7.41 (m, 2H), 7.49 (m, 3H), 7.78 (d, 1H).

Step E: [2-bromo-4-[5-(3,5-dichlorophenyl)-5-(trifluoromethyl)-4H-isoxazol-3-yl]phenyl]sulfanylmethanesulfonamide

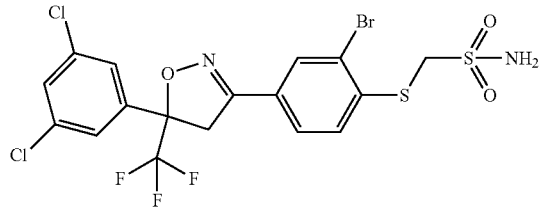 [SMILES: NS(=O)(=O)CSc1ccc(C2=NOC(c3cc(Cl)cc(Cl)c3)(C(F)(F)F)C2)cc1Br]

To a solution of 2-bromo-4-[5-(3,5-dichlorophenyl)-5-(trifluoromethyl)-4H-isoxazol-3-yl]benzenethiol (0.47 g) in N,N-dimethylformamide (7 ml) at room temperature was added potassium carbonate (0.2 g) then a solution of chloromethanesulfonamide (0.14 g) in N,N-dimethylformamide (3 ml); the resulting solution was stirred for 2 hours at room temperature, diluted with ethyl acetate (15 ml) then washed with 1N HCl solution (5 ml). The combined organic layers were washed with water then brine and dried over anhydrous sodium sulfate, filtered and concentrated under reduced pressure to dryness to afford a crude residue (275 mg), which was purified with Combiflash Rf200, (column of 5 g), eluted with heptane/EtOAc to afford the title product (0.275 g) as a white solid. LCMS (Method A) RT 1.14 min, [M+H]⁺563/565. ¹H-NMR (CDCl₃, 400 MHz): 3.60 (d, 1H), 3.98 (d, 1H), 4.35 (s, 2H), 4.70 (br s, 2H), 7.36 (t, 1H), 7.41 (d, 2H), 7.52 (dd, 1H), 7.60 (d, 1H), 7.82 (d, 2H). ¹⁹F-NMR (CDCl₃, 400 MHz): −78.8.

EXAMPLE 2

1-[2-bromo-4-[5-(3,5-dichlorophenyl)-5-(trifluoromethyl)-4H-isoxazol-3-yl]phenyl]sulfanyl-N-ethyl-methanesulfonamide and 1-[2-bromo-4-[5-(3,5-dichlorophenyl)-5-(trifluoromethyl)-4H-isoxazol-3-yl]phenyl]sulfanyl-N,N-diethyl-methanesulfonamide

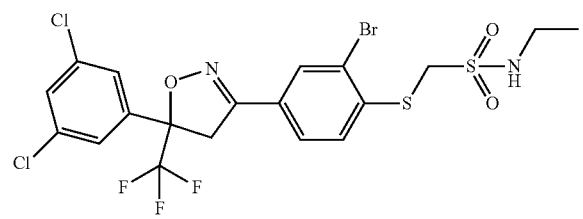

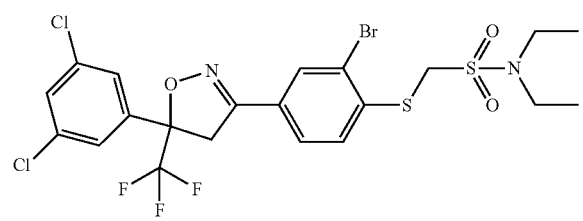

Potassium carbonate (30 mg) and [2-bromo-4-[5-(3,5-dichlorophenyl)-5-(trifluoromethyl)-4H-isoxazol-3-yl]phenyl]sulfanylmethanesulfonamide (100 mg, example 1) were placed in a 10 ml flask under argon then N,N-dimethylformamide (3 ml) was added and the solution cooled to 0° C. Iodoethane (28 mg) was added dropwise over 10 min and the resulting mixture was stirred at room temperature overnight. The mixture was poured into water extracted with diethyl ether. The organic layer was washed with 1N HCl, water then brine, dried over sodium sulphate and concentrated in vacuo to afford a brown solid (150 mg). The crude residue was purified with combiflash Rf 200 machine (column of 5 g, eluted with Heptane/EtOAc) to afford 1-[2-bromo-4-[5-(3,5-dichlorophenyl)-5-(trifluoromethyl)-4H-isoxazol-3-yl]phenyl]sulfanyl-N-ethyl-methanesulfonamide (53 mg) as a white solid together with 1-[2-bromo-4-[5-(3,5-dichlorophenyl)-5-(trifluoromethyl)-4H-isoxazol-3-yl]phenyl]sulfanyl-N,N-diethyl-methanesulfonamide (30 mg) as a white solid.

1-[2-bromo-4-[5-(3,5-dichlorophenyl)-5-(trifluoromethyl)-4H-isoxazol-3-yl]phenyl]sulfanyl-N-ethyl-methanesulfonamide: LCMS (Method A) RT 2.60 min. [M−H]⁻589/591/593; [M-SO2NHEt]⁻481. ¹H NMR (400 MHz, CDCl₃) 1.25 (t, 3H), 3.25 (m, 2H), 3.70 (d, 1H), 4.06 (d, 1H), 4.38 (s, 2H), 4.55 (br t, 1H), 7.45 (t, 1H), 7.51 (d, 2H), 7.61 (dd, 1H), 7.70 (d, 1H), 7.90 (s, 1H). ¹⁹F-NMR (CDCl₃, 400 MHz): −5 79.4

1-[2-bromo-4-[5-(3,5-dichlorophenyl)-5-(trifluoromethyl)-4H-isoxazol-3-yl]phenyl]sulfanyl-N,N-diethyl-methanesulfonamide: LCMS (Method A) RT 2.81 min. [M−H]⁻ 618/619/621. ¹H NMR (400 MHz, CDCl₃) 1.15 (t, 6H), 3.30 (m, 4H), 3.60 (d, 1H), 3.97 (d, 1H), 4.22 (s, 2H), 7.35 (t, 1H), 7.41 (d, 2H), 7.51 (dd, 1H), 7.60 (d, 1H), 7.80 (s, 1H). ¹⁹F-NMR (CDCl₃, 400 MHz): −79.4.

EXAMPLE 3

[2-bromo-4-[5-(3,5-dichlorophenyl)-5-(trifluoromethyl)-4H-isoxazol-3-yl]phenyl]sulfonylmethanesulfonamide

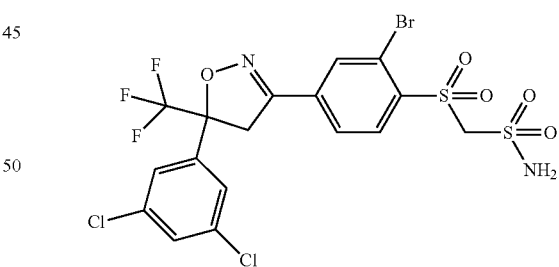

To a solution of [2-bromo-4-[5-(3,5-dichlorophenyl)-5-(trifluoromethyl)-4H-isoxazol-3-yl]phenyl]sulfanylmethanesulfonamide (50 mg) in dichloromethane was added meta-chloroperbenzoic acid (70%w/w, 70 mg) at 0° C. The resulting mixture was allowed to stir at room temperature overnight. The organic phase was washed with an aqueous saturated sodium hydrogen carbonate solution then twice with water, dried over anhydrous sodium sulfate, filtered and evaporated to give a white solid. The crude residue was purified with Combiflash Rf 200 machine (column of 5 g, eluted with DCM/MeOH 5%) to afford the title compound as a white solid. LCMS (Method A) RT 2.01 min. [M−H]⁻

593/595/597. ¹H NMR (400 MHz, CDCl₃) 3.72 (d, 1H), 4.10 (d, 1H), 5.08 (s, 2H), 5.32 (s, 2H), 7.40-8.30 (m, 6H). ¹⁹F-NMR (CDCl₃, 400 MHz): −79.5.

The following compounds were prepared following a similar method to that described in Example 3: 1-[2-bromo-4-[5-(3,5-dichlorophenyl)-5-(trifluoromethyl)-4H-isoxazol-3-yl]phenyl]sulfonyl-N-cyclopropyl-methanesulfonamide.

EXAMPLE 4

1-[2-bromo-4-[(5S)-5-(3,5-dichlorophenyl)-5-(trifluoromethyl)-4H-isoxazol-3-yl]phenyl]sulfanyl-N-ethyl-methanesulfonamide

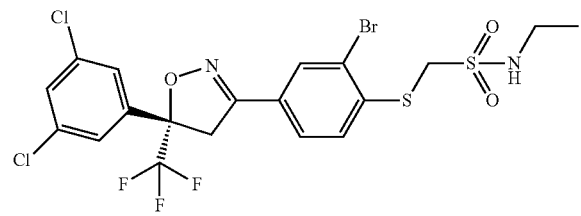 [SMILES: CCNS(=O)(=O)CSc1ccc(C2=NO[C@@](c3cc(Cl)cc(Cl)c3)(C(F)(F)F)C2)cc1Br]

Step A: (5S)-3-(3-bromo-4-tert-butylsulfanyl-phenyl)-5-(3,5-dichlorophenyl)-5-(trifluoromethyl)-4H-isoxazole

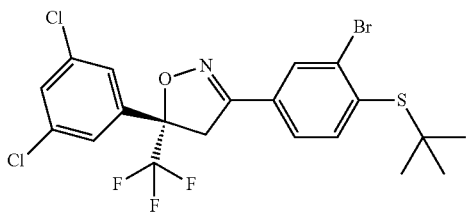 [SMILES: CC(C)(C)Sc1ccc(C2=NO[C@@](c3cc(Cl)cc(Cl)c3)(C(F)(F)F)C2)cc1Br]

5 To a solution of (E)-1-(3-bromo-4-tert-butylsulfanyl-phenyl)-3-(3,5-dichlorophenyl)-4,4,4-trifluoro-but-2-en-1-one (Example 1, Step B, 1.0 g) in chloroform (50 ml) was added 1-anthracen-9-ylmethyl quininium chloride (220 mg). The reaction mixture was cooled at −20° C. then hydroxylamine (50% in water, 0.24 ml) and cesium hydroxide (10 N in water, 0.46 ml) were added simultaneously. The reaction was stirred at -20° C. for 2 hour and then brought back to room temperature. The mixture was diluted with water and extracted with dichloromethane several times; the combined organic layers were dried over MgSO₄ and the solvent evaporated under reduced pressure to obtain a brown gum (1 g) which was purified by with the Combiflash Rf200, (column of 48 g), eluted with heptane/EtOAc to afford the title product (834 mg) as a yellow solid. LCMS (Method A) RT 1.42 min, [M+Na]⁺544/546/548; ¹H-NMR (CDCl₃, 400 MHz): 1.38 (s, 9H), 3.68 (d, 1H), 4.07 (d, 1H), 7.43 (t, 1H), 7.50 (s, 2H), 7.59 (dd, 1H), 7.68 (d, 1H), 7.91 (d, 1H). ¹⁹F-NMR (CDCl₃, 400 MHz): -79.4. The product was analysed by chiral HPLC (method F): 2.39 min (85.2%), 3.21 min (14.8%).

Step B: 2-bromo-4-[(5S)-5-(3,5-dichlorophenyl)-5-(trifluoromethyl)-4H-isoxazol-3-yl]benzenethiol

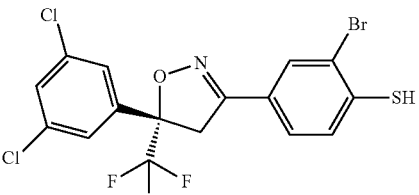

To a solution of (5S)-3-(3-bromo-4-tert-butylsulfanyl-phenyl)-5-(3,5-dichlorophenyl)-5-(trifluoromethyl)-4H-isoxazole (5.0 g) in toluene (50 mL) was added toluene-4-sulfonic acid (3.33 g) and the reaction was heated at a 110° C. overnight. The reaction was cooled backt down to room temperature and diluted in dichloromethane and washed with an aqueous saturared NaHCO₃ solution. The organic phase was dried over MgSO₄ and the solvents removed in vacuo to yield the crude product (5.3 g). The crude product was passed through a pad of silica and eluting with heptanes/ethyl acetate (8:1). The product obtained was then triturated with heptanes to yield the title compound as an off-white solide (3.5 g). LCMS (Method A) RT 1.33 min, [M−H]⁻ 468/470/472; ¹H-NMR (CDCl₃, 400 MHz): 3.64 (d, 1H), 4.03 (d, 1H), 4.17 (s, 1H, SH), 7.39 (d, 1H), 7.41 (m, 2H), 7.49 (m, 3H), 7.78 (d, 1H). ¹⁹F-NMR (CDCl₃, 400 MHz): -79.5.

Step C: N-ethyl-1-sulfanyl-methanesulfonamide

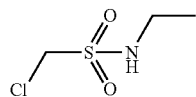

A 50 ml 3-necked round-bottom flask, equipped with a stirrer, thermometer, condenser, dropping funnel was charged with 15 ml of diethyl ether and cooled in an MeOH-ice bath. A solution of 2M ethylamine (13 ml) in THF was added, then a solution of chloromethane sulfonyl chloride (1.5 g) in diethyl ether (5 ml) was added dropwise to the well-stirred solution while the temperature was kept below 0° C. After all of the sulfonyl chloride was added, the temperature was brought to 25° C., and stirring was continued at this temperature for 2 hours. At the end of this time, the reaction mixture was filtered, diluted with diethyl ether. The solution was washed with water, 2N HCL solution, water, aqueous sodium hydrogen carbonate solution, water, brine and dried over magnesium sulfate, filtered and concentrated under vacuum. The resulting crude N-ethyl chloromethane sulfonamide was obtained as a clear brown liquid (ca 1.7 g) and used as such in the next step. ¹H-NMR (CDCl₃, 400 MHz): 1.2 (t, 3H), 3.2 (m, 2H), 4.41 (s, 2H).

Step D: 1-[2-bromo-4-[(5S)-5-(3,5-dichlorophenyl)-5-(trifluoromethyl)-4H-isoxazol-3-yl]phenyl]sulfanyl-N-ethyl-methanesulfonamide

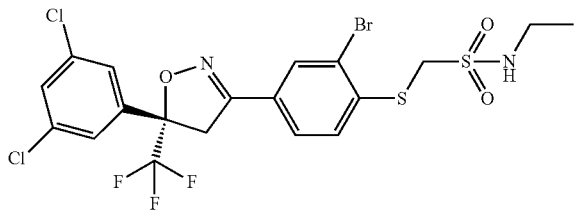 [SMILES: CCNS(=O)(=O)CSc1ccc(C2=NO[C@@](c3cc(Cl)cc(Cl)c3)(C(F)(F)F)C2)cc1Br]

A solution of 2-bromo-4-[(5S)-5-(3,5-dichlorophenyl)-5-(trifluoromethyl)-4H-isoxazol-3-yl]benzenethiol (150 mg) in DMF (4 ml) was treated with potassium carbonate (71 mg) then the resulting mixture was stirred for 5 min at room temperature. A solution of N-ethyl-1-sulfanyl-methanesulfonamide (105 mg) in DMF (0.5 ml) was added and the reaction was stirred at 90° C. for 30 min. The reaction mixture was poured into water then extracted with ethyl acetate, washed with water then brine, dried over magnesium sulfate and then evaporated under reduced pressure at 40° C. to give the crude product (140 mg). The residue was purified with Combiflash Rf200, (column of 4 g), eluted with heptane/EtOAc to afford the title product (135 mg) as a yellow solid. LCMS and $^1$H NMR data corresponded to those obtained in Example 2.

The following compounds were prepared following a similar method to that described in Example 4: 1-[2-bromo-4-[(5S)-5-(3,5-dichlorophenyl)-5-(trifluoromethyl)-4H-isoxazol-3-yl]phenyl]sulfanyl-N-(2,2,2-trifluoroethyl)-methanesulfonamide, 1-[2-bromo-4-[(5S)-5-(3,5-dichlorophenyl)-5-(trifluoromethyl)-4H-isoxazol-3-yl]phenyl]sulfanyl-N-cyclopropyl-methanesulfonamide, 1-[2-bromo-4-[(5S)-5-(3,5-dichlorophenyl)-5-(trifluoromethyl)-4H-isoxazol-3-yl]phenyl]sulfanyl-N-propargyl-methanesulfonamide, 1-[2-bromo-4-[(5S)-5-(3,5-dichlorophenyl)-5-(trifluoromethyl)-4H-isoxazol-3-yl]phenyl]sulfanyl-N-isopropyl-methanesulfonamide.

EXAMPLE 5

1-[2-bromo-4-[2-(3,5-dichlorophenyl)-2-(trifluoromethyl)-3H-thiophen-4-yl]phenyl]sulfanyl-N,N-diethyl-methanesulfonamide(D-1)

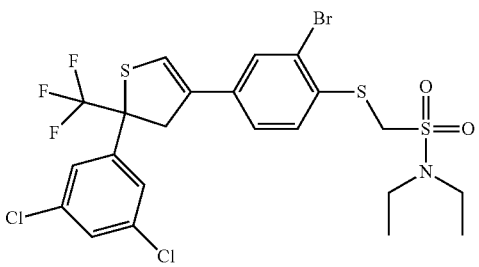 [SMILES: CCN(CC)S(=O)(=O)CSc1ccc(C2=CSC(c3cc(Cl)cc(Cl)c3)(C(F)(F)F)C2)cc1Br]

Step A: Ethyl 3-(3-bromo-4-tert-butylsulfanyl-phenyl)-5-(3,5-dichlorophenyl)-3-hydroxy-5-(trifluoromethyl)tetrahydrothiophene-2-carboxylate

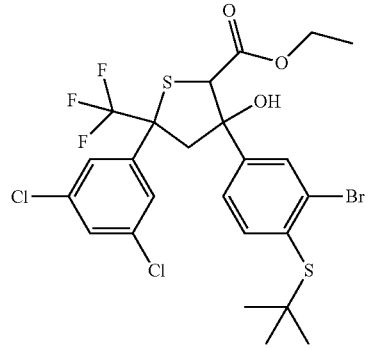 [SMILES: CCOC(=O)C1SC(c2cc(Cl)cc(Cl)c2)(C(F)(F)F)CC1(O)c1ccc(SC(C)(C)C)c(Br)c1]

To a stirring solution of (Z)-1-(3-bromo-4-tert-butylsulfanyl-phenyl)-3-(3,5-dichlorophenyl)-4,4,4-trifluoro-but-2-en-1-one (10 g) in tetrahydrofuran (100 mL). Ethyl 2-sulfanylacetate (6.96 g) and triethylamine (960 g) was added. The reaction was stirred at RT under nitrogen atmosphere for overnight.

After completion of reaction, monitored by TLC, the reaction mass was evaporated off under reduced pressure, diluted with water (150 mL) and extracted with ethyl acetate (2×100 mL). The combined organic phases were evaporated under reduced pressure and the crude residue was purified by column chromatography using cyclohexane/ethyl acetate as an eluent to afford the title product (8 g). LCMS (Method A) RT 2.73 min, [M+Na]$^+$654.0; $^1$H-NMR (CDCl$_3$, 400 MHz): 7.82 (d, 1H), 7.66 (dd, 1H), 7.50-7.52(m, 2H), 7.36-7.38 (m, 2H), 4.71 (s, 1H), 4.57 (s, 1H), 4.10-4.16 (q, 2H), 2.99 (d, 1H), 2.87 (d, 1H) 1.356 (s, 9H), 1.15-1.18 (t, 3H).

Step B: 3-(3-bromo-4-tert-butylsulfanyl-phenyl)-5-(3,5-dichlorophenyl)-3-hydroxy-5-(trifluoromethyl)tetrahydrothiophene-2-carboxylic acid

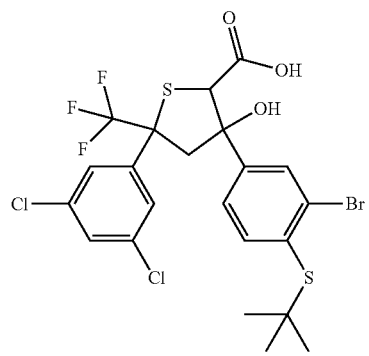 [SMILES: CC(C)(C)Sc1ccc(C2(O)CC(c3cc(Cl)cc(Cl)c3)(C(F)(F)F)SC2C(=O)O)cc1Br]

To a stirring solution of ethyl 3-(3-bromo-4-tert-butylsulfanyl-phenyl)-5-(3,5-dichlorophenyl)-3-hydroxy-5-(trifluoromethyl)tetrahydrothiophene-2-carboxylate (8 g) in tetrahydrofuran (100 ml) was added lithium hydroxide (576 mg) in water (5 mL). The reaction was stirred at room temperature for overnight. After completion of reaction monitored by TLC, reaction mass was evaporated off under reduced pressure, diluted with water (15 mL), acidified with HCl solution (5%) and extracted with ethyl acetate (2×100 mL). The combined organic layer was washed with water (50 mL), dried over sodium sulphate, evaporated off under reduced pressure. Thus obtained compound (7.5 g) was taken as such for next step without further purification.

Step C: 4-(3-bromo-4-tert-butylsulfanyl-phenyl)-2-(3,5-dichlorophenyl)-2-(trifluoromethyl)-3H-thiophene

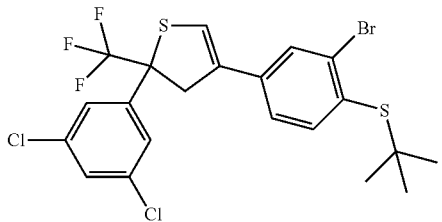 [SMILES: CC(C)(C)Sc1ccc(C2=CSC(c3cc(Cl)cc(Cl)c3)(C(F)(F)F)C2)cc1Br]

To a stirring solution of 3-(3-bromo-4-tert-butylsulfanyl-phenyl)-5-(3,5-dichlorophenyl)-3-hydroxy-5-(trifluoromethyl)tetrahydrothiophene-2-carboxylic acid (7.5 g) in pyridine (30 mL) and followed addition of methanesulfonyl chloride (3.02 g) at 0° C. and stirring was continued at room temperature for overnight. After completion of reaction monitored by TLC, the reaction mass was diluted with water (15 mL), extracted with ethyl acetate (3 × 60 mL). The combined organic layer was dried over sodium sulphate and evaporated off under reduced pressure.

Thus obtained 543-bromo-4-tert-butylsulfanyl-phenyl)-3-(3 ,5-dichlorophenyl)-3-(trifluoromethyl)-6-oxa-2-thiabicyclo[3.2.0]heptan-7-one (6 g) was diluted with in N,N-dimethylformamide (30 mL) heating 10 was applied at 100° C. for 2hr. After completion of reaction monitored by TLC, the reaction mass was diluted with water (100 mL) extracted with ethyl acetate (3×40 mL). The combined organic layers were washed with water (2×50 mL) dried over sodium sulphate and evaporated under reduced pressure. The crude residue was purified by column chromatography using cyclohexane/ethyl acetate as an eluent to afford the title product (4 g). LCMS (Method A) RT 2.64 min, [M+H]+ 540.8; $^1$H-NMR (CDCl$_3$, 400 MHz): 7.59-7.63 (m, 2H), 7.38-7.41 (m, 2H), 7.25-7.26 (m, 2H), 6.61 (s, 1H), 3.83 (d, 1H), 3.60 (d, 1H), 1.34 (s, 9H)

Step D: 2-bromo-4-[2-(3,5-dichlorophenyl)-2-(trifluoromethyl)-3H-thiophen-4-yl]benzenethiol

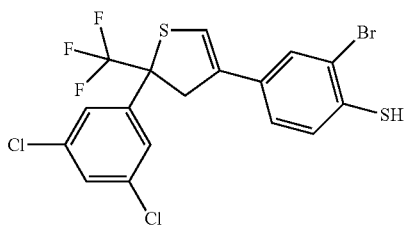 [SMILES: FC(F)(F)C1(c2cc(Cl)cc(Cl)c2)CC(c2ccc(S)c(Br)c2)=CS1]

To a stirring solution of 4-(3-bromo-4-tert-butylsulfanyl-phenyl)-2-(3,5-dichlorophenyl)-2-(trifluoromethyl)-3H-thiophene (1 g) in methylene chloride (15 mL), boron tribromide (1.37 g) was added at 0° C. and stirring was continued for 2hr. After completion of reaction monitored by TLC. The reaction mass was quenched with methanol (0.3 ml) and diluted with ice cold water (10 mL) and extracted with DCM (2×20 mL). The combined organic layers were washed with water (30 mL), dried over sodium sulphate and evaporated under reduced pressure. The crude residue was purified by column chromatography using cyclohexane/ethyl acetate as an eluent to afford the title product (800 mg). LCMS (Method A) RT 2.73 min, [M−H]+484.8; $^1$H-NMR (CDCl$_3$, 400 MHz): 7.37-7.49(m, 5H), 7.08(dd, 1H), 6.40 (s, 1H), 3.70 (d, 1H), 3.51 (d, 1H).

Step E: 1-chloro-N,N-diethyl-methanesulfonamide

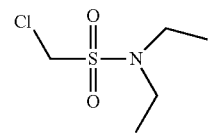

To a stirring solution of triethylamine (1.1 mL) and N-ethylethanamine (0.76 mL) in dichloromethane (10 mL) −5° C. was added chloromethanesulfonyl chloride (1 g). The resulting mixture was stirred at room temperature for 2 hours. Reaction mixture was diluted with DCM (5 mL), washed with 10% HCl solution (5 mL), and followed by sodium bicarbonate solution (5 mL). The combined organic layer was dried over sodium sulphate, concentrated under reduced pressure to afford title compounds as yellow oil (900 mg).

$^1$H NMR (CDCl$_3$, 400 MHz,): 4.47 (s, 2H), 3.36 (q, 4H), 1.19 (t, 6H)

Step F: 1-[2-bromo-4-[2-(3,5-dichlorophenyl)-2-(trifluoromethyl)-3H-thiophen-4-yl]phenyl]sulfanyl-N,N-diethyl-methanesulfonamide (D-1)

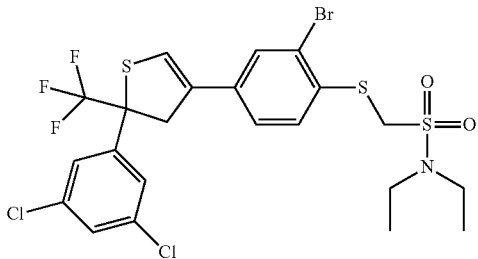 [SMILES: CCN(CC)S(=O)(=O)CSc1ccc(C2=CSC(c3cc(Cl)cc(Cl)c3)(C(F)(F)F)C2)cc1Br]

To a stirring solution of 2-bromo-4-[2-(3,5-dichlorophenyl)-2-(trifluoromethyl)-3H-thiophen-4-yl]benzenethiol (200 mg) in DMF (3 mL) was degassed by bubbling nitrogen for 10 mins To this was then added sodium borohydride (14 mg), potassium carbonate (85 mg) stirred for 5 mins at room temperature, followed by addition of 1-chloro-N,N-diethyl-methanesulfonamide (190 mg). The resulting mixture was stirred at 90° C. under a nitrogen atmosphere for 4 hours. The reaction mixture was diluted with water (15 mL) and extracted with ethyl acetate (3×30 mL).The combined organic layers were dried over sodium sulphate, filtered and concentrated under reduced pressure. The crude product was purified by column chromatography eluted with cyclohexane/ethyl acetate (6:4) to obtain the titled compound as a solid (90 mg). LCMS (Method A) RT 5.49 min [M+H]+ 634.0. $^1$H NMR (CDCl$_3$, 400 MHz,): 7.65 (d, 1H), 7.54(d, 1H), 7.40 (dd, 2H), 7.38 (d, 1H), 7.28 (dd, 1H), 6.58 (m, 1H), 4.25 (s, 2H), 3.83 (d, 1H), 3.62 (d, 1H), 3.4 (q, 4H), 1.25 (t, 6H).

EXAMPLE 6

1-[2-bromo-4-[2-(3,5-dichlorophenyl)-2-(trifluoromethyl)-3H-thiophen-4-yl]phenyl]sulfanyl-N-ethyl-methanesulfonamide (D-2)

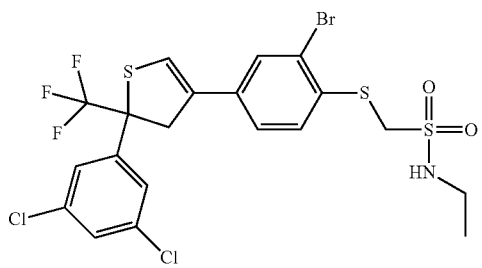 [SMILES: CCNS(=O)(=O)CSc1ccc(C2=CSC(c3cc(Cl)cc(Cl)c3)(C(F)(F)F)C2)cc1Br]

To a stirring solution of 2-bromo-4-[2-(3,5-dichlorophenyl)-2-(trifluoromethyl)-3H-thiophen-4-yl]benzenethiol (200 mg) in DMF (3 mL) was degassed by bubbling nitrogen for 10 mins To this was then added sodium borohydride (14 mg), potassium carbonate (85 mg) stirred for 5 mins at room temperature, followed by addition of 1-chloro-N-ethyl-methanesulfonamide (161 mg). The resulting mixture was stirred at 90° C. under a nitrogen atmosphere for 4 hours. The reaction mixture was diluted with water (15 mL) and extracted with ethyl acetate (3 x 30 mL).The combined organic layers were dried over sodium sulphate, filtered and concentrated under reduced pressure. The crude product was purified by column chromatography eluted with cyclohexane/ethyl acetate (6:4) to obtain the titled compound as a solid (180 mg). LCMS (Method A) RT 5.38 min [M–H]$^1$ 605.4. $^1$H NMR (CDCl$_3$, 400 MHz,): 7.67 (dd, 1H), 7.56 (m, 1H), 7.40 (d, 2H), 7.38 (d, 1H), 7.28 (m, 1H), 6.6 (s, 1H), 5.83 (brs, 1H), 4.29 (s, 2H), 3.83 (d, 1H), 3.63 (d, 1H), 3.11(q, 2H), 1.16 (t, 3H).

TABLE A

Compounds of formula (I-a):

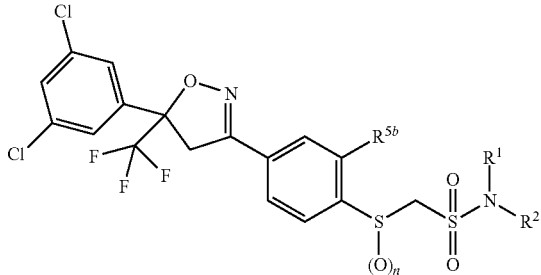

(I-a)

| Comp No. | n | R$^{5b}$ | R$^2$ | R$^1$ | $^1$H NMR |
|---|---|---|---|---|---|
| A1 | 0 | Br | H | H | (CDCl$_3$, 400 MHz): 3.60 (d, 1H), 3.98 (d, 1H), 4.35 (s, 2H), 4.70 (br s, 2H), 7.36 (t, 1H), 7.41 (d, 2H), 7.52 (dd, 1H), 7.60 (d, 1H), 7.82 (d, 2H) |
| A2 | 0 | Br | Et | Et | (400 MHz, CDCl$_3$) 1.15 (t, 6H), 3.30 (m, 4H), 3.60 (d, 1H), 3.97 (d, 1H), 4.22 (s, 2H), 7.35 (t, 1H), 7.41 (d, 2H), 7.51 (dd, 1H), 7.60 (d, 1H), 7.80 (s, 1H) |
| A3 | 0 | Br | Et | H | (400 MHz, CDCl$_3$) 1.15 (t, 3H), 3.11 (m, 2H), 3.60 (d, 1H), 3.97 (d, 1H), 4.28 (s, 2H), 4.55 (br t, 1H), 7.35 (t, 1H), 7.41 (d, 2H), 7.51 (dd, 1H), 7.60 (d, 1H), 7.80 (s, 1H) |
| A4 | 2 | Br | H | H | (400 MHz, CDCl$_3$) 3.72 (d, 1H), 4.10 (d, 1H), 5.08 (s, 2H), 5.32 (s, 2H), 7.40-8.30 (m, 6H) |

TABLE B

Compounds of formula (I-b):

(I-b)

| Comp No. | n | $R^{5b}$ | $R^2$ | $R^1$ | $^1$H NMR |
|---|---|---|---|---|---|
| B1 | 0 | Br | Et | H | 1.25 (t, 3H), 3.25 (m, 2H), 3.70 (d, 1H), 4.06 (d, 1H), 4.38 (s, 2H), 4.55 (br t, 1H), 7.45 (t, 1H), 7.51 (d, 2H), 7.61 (dd, 1H), 7.70 (d, 1H), 7.90 (s, 1H) |
| B2 | 0 | Br | CF$_3$CH$_2$ | Et | (400 MHz, CDCl$_3$) 3.69 (d, 1H), 3.85 (m, 2H), 4.05 (d, 1H), 4.41 (s, 2H), 5.00 (m, 1H), 7.40-7.90 (m, 1H) |
| B3 | 0 | Br | cyclopropyl | H | (400 MHz, CDCl$_3$) 0.70-0.80 (m, 4H), 2.55 (m, 1H), 3.69 (d, 1H), 4.05 (d, 1H), 4.41 (s, 2H), 5.00 (s, 1H), 7.35 (m, 1H), 7.50 (m, 2H), 7.52 (dd, 1H), 7.70 (d, 1H), 7.90 (s, 1H) |
| B4 | 0 | Br | isopropyl | H | (400 MHz, CDCl$_3$) 1.30 (d, 6H), 3.70 (d, 1H), 3.72 (m, 1H), 4.05 (d, 1H), 4.45 (s, 2H), 7.46 (t, 1H), 7.51 (s, 2H), 7.61 (dd, 1H), 7.70 (d, 1H), 7.90 (d, 1H) |
| B5 | 0 | Br | propargyl | H | (400 MHz, CDCl$_3$) 2.45 (t, 1H), 3.70 (d, 2H), 4.0-4.1 (m, 3H), 4.51 (s, 2H), 5.0 (bt, 1H), 7.46 (t, 1H), 7.51 (s, 2H), 7.61 (dd, 1H), 7.70 (d, 1H), 7.90 (d, 1H) |
| B6 | 2 | Br | cyclopropyl | H | (400 MHz, CDCl$_3$) 0.80-0.90 (m, 4H), 2.70 (m, 1H), 3.72 (d, 1H), 4.10 (d, 1H), 5.05 (s, 2H), 5.32 (s, 1H), 7.40-7.50 (m, 3H), 7.80 (d, 1H), 8.12 (s, 1H), 8.22 (d, 1H) |

TABLE C

Compounds of formula (I-c):

(I-b)

| Comp No. | n | $R^{5b}$ | $R^2$ | $R^1$ | RT | MS |
|---|---|---|---|---|---|---|
| C1 | 0 | Br | n-butyl | H | 2.29 | 617.12 |
| C2 | 0 | Br | 1-methoxy-prop-2yl | H | 2.22 | 633.09 |
| C3 | 0 | Br | 1,1,1-trifluoropropyl | H | 2.22 | 657.04 |
| C4 | 0 | Br | prop-2yl | H | 2.28 | 617.09 |
| C5 | 0 | Br | tetrahydrofuran-2-ylmethyl | H | 2.2 | 645.06 |
| C6 | 0 | Br | benzyl | H | 2.28 | 651.11 |
| C7 | 0 | Br | 1-phenylethyl | H | 2.33 | 665.08 |
| C8 | 0 | Br | 1,1-dioxothietan-3-yl | H | 2.05 | 664.99 |
| C9 | 0 | Br | (6-chloro-3-pyridyl)methyl | H | 2.2 | 686.00 |
| C10 | 0 | Br | 3-fluorophenyl | H | 2.27 | 655.05 |
| C11 | 0 | Br | 2-pyridylmethyl | H | 2.13 | 652.05 |
| C12 | 0 | Br | 3-methylthietan-3-yl | H | 2.27 | 647.03 |
| C13 | 0 | Br | 1,1-dimethyl-2-methylsulfanyl-ethyl | H | 2.33 | 663.08 |
| C14 | 0 | Br | 1-oxothietan-3-yl | H | 2 | 649.03 |
| C15 | 0 | Br | norbornan-2-yl | H | 2.37 | 655.12 |
| C16 | 0 | Br | cyclobutyl | H | 2.25 | 615.05 |
| C17 | 0 | Br | 4-fluorophenyl | H | 2.26 | 655.04 |
| C18 | 0 | Br | 2-ethoxyethyl | H | 2.22 | 633.10 |
| C19 | 0 | Br | propyl | H | 2.23 | 603.06 |
| C20 | 0 | Br | cyclopropylmethyl | H | 2.24 | 615.06 |
| C21 | 0 | Br | cyclopentyl | H | 2.3 | 629.07 |
| C22 | 0 | Br | allyl | H | 2.19 | 601.10 |
| C23 | 0 | Br | cyclobutylmethyl | H | 2.31 | 629.11 |
| C24 | 0 | Br | 4-trifluoromethylbenzyl | H | 2.34 | 719.12 |
| C25 | 0 | Br | 2-butyl | H | 2.28 | 617.10 |
| C26 | 0 | Br | 2-(1,3-dioxolan-2-yl)ethyl | H | 2.15 | 661.07 |
| C27 | 0 | Br | cyclopent-3-en-1-yl | H | 2.26 | 627.10 |
| C28 | 0 | Br | [(2R)-tetrahydrofuran-2-yl]methyl | H | 2.2 | 645.09 |

TABLE C-continued

Compounds of formula (I-c):

(I-b)

[Structure diagram of compound I-b showing dichlorophenyl, CF2, isoxazoline, phenyl with R5b, S(O)n, CH2, S(O2), N(R1)(R2) groups]

| Comp No. | n | R5b | R2 | R1 | RT | MS |
|---|---|---|---|---|---|---|
| C29 | 0 | Br | 1-ethylpropyl | H | 2.34 | 631.07 |
| C30 | 0 | Br | oxetan-3yl | H | 2.07 | 617.07 |
| C31 | 0 | Br | 2-methylsulfanylethyl | H | 2.21 | 635.07 |
| C32 | 0 | Br | tetrahydrothiophen-3-yl | H | 2.23 | 647.10 |
| C33 | 0 | Br | (2-fluorophenyl)methyl | H | 2.24 | 669.06 |
| C34 | 0 | Br | (4-methoxyphenyl)methyl | H | 2.22 | 681.07 |
| C35 | 0 | Br | 2,5-dimethylpyrazol-3-yl | H | 2.02 | 655.06 |
| C36 | 0 | Br | thietan-3yl | H | 2.16 | 633.01 |
| C37 | 0 | Br | 2-methoxyethyl | H | 2.1 | 619.10 |
| C38 | 0 | Br | isopropyl | ethyl | 2.35 | 631.09 |
| C39 | 0 | Br | t-butyl | methyl | 2.34 | 631.07 |
| C40 | 0 | Br | propyl | methyl | 2.29 | 617.09 |
| C41 | 0 | Br | ethyl | ethyl | 2.29 | 617.07 |
| C42 | 0 | Br | —CH$_2$—CH=CH—CH$_2$—CH$_2$— | | 2.27 | 627.04 |
| C43 | 0 | Br | —CH$_2$—CH=CH—CH$_2$— | | 2.2 | 613.03 |
| C44 | 0 | Br | —CH$_2$—CH$_2$—CH$_2$—CH(CH$_3$)— | | 2.29 | 629.04 |
| C45 | 0 | Br | —CH$_2$—CH$_2$—CH(CH$_3$)—CH$_2$—CH$_2$— | | 2.37 | 643.10 |
| C46 | 0 | Br | isobutyl | methyl | 2.35 | 631.07 |
| C47 | 0 | Br | —(CH$_2$)$_4$— | | 2.22 | 615.07 |
| C48 | 0 | Br | —(CH$_2$)$_6$— | | 2.37 | 643.08 |
| C49 | 0 | Br | 1-cyanocyclopropyl | H | 2.08 | 626.06 |
| C50 | 0 | Br | 2-methoxyethyl | methyl | 2.21 | 633.07 |
| C51 | 0 | Br | —(CH$_2$)$_5$— | | 2.31 | 629.08 |
| C52 | 0 | Br | allyl | methyl | 2.26 | 615.05 |
| C53 | 0 | Br | ethyl | methyl | 2.23 | 603.05 |
| C54 | 0 | Br | —CH$_2$—CH$_2$—O—CH$_2$—CH$_2$— | | 2.14 | 631.04 |
| C55 | 0 | Br | isopropyl | methyl | 2.29 | 617.06 |
| C56 | 0 | Br | propargyl | methyl | 2.2 | 613.04 |

Biological Examples

This Example illustrates the pesticidal/insecticidal properties of compounds of formula (I). Tests were performed as follows:

*Spodoptera littoralis* (Egyptian Cotton Leaf Worm)

Cotton leaf discs were placed on agar in 24-well microtiter plates and sprayed with aqueous test solutions prepared from 10'000 ppm DMSO stock solutions. After drying the leaf discs were infested with five L1 larvae. The samples were assessed for mortality, anti-feedant effect, and growth inhibition 3 days after infestation. Control of *Spodoptera littoralis* by a test sample is noted when at least one of mortality, anti-feedant effect, and growth inhibition is better than the untreated sample.

The following compounds resulted in at least 80% control at an application rate of 200 ppm: A1, A2, A3, A4, B1, B2, B3, B4, B5, B6, C1 to C47, C49 to C56, D2

*Heliothis virescens* (Tobacco Budworm):

Eggs (0-24 h old) were placed in 24-well microtiter plates on artificial diet and treated with aqueous test solutions prepared from 10'000 ppm DMSO stock solutions by pipetting. The samples were assessed for egg mortality, larval mortality and growth inhibition 5 days after infestation. Control of *Heliothis virescens* by a test sample is noted when at least one of egg mortality, larval mortality and growth inhibition is better than the untreated sample.

The following compounds resulted in at least 80% control at an application rate of 200 ppm: A1, A2, A3, A4, B1, B2, B3, B4, B5, B6, D2

*Plutella xylostella* (Diamond Back Moth):

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition 5 days after infestation. Control of *Plutella xyllostella* by a test sample is noted when at least one of mortality and growth inhibition is better than the untreated sample.

The following compounds resulted in at least 80% control at an application rate of 200 ppm: A1, A2, A3, A4, B1, B2, B3, B4, B5, B6, C1 to C23, C25 to C34, C36 to C56, D2

TABLE D

Compounds of formula (I-d):

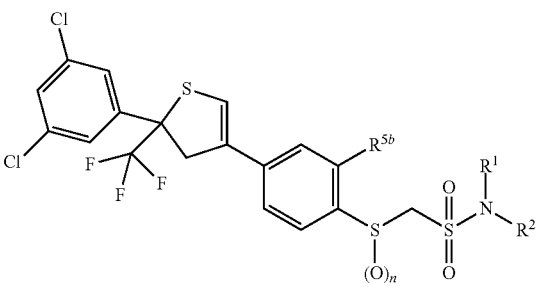

| Comp No. | n | R5b | R2 | R1 | 1H NMR |
|---|---|---|---|---|---|
| D1 | 0 | Br | Et | Et | (CDCl$_3$, 400 MHz): 7.65 (d, 1H), 7.54 (d, 1H), 7.40 (dd, 2H), 7.38 (d, 1H), 7.28 (dd, 1H), 6.58 (m, 1H), 4.25 (s, 2H), 3.83 (d, 1H), 3.62 (d, 1H), 3.4 (q, 4H), 1.25 (t, 6H) |
| D2 | 0 | Br | H | Et | (400 MHz, CDCl$_3$) 7.67 (dd, 1H), 7.56 (m, 1H), 7.40 (d, 2H), 7.38 (d, 1H), 7.28 (m, 1H), 6.6 (s, 1H), 5.83 (brs, 1H), 4.29 (s, 2H), 3.83 (d, 1H), 3.63 (d, 1H), 3.11 (q, 2H), 1.16 (t, 3H). |

Diabrotica balteata (Corn Rootworm):

24-well microtiter plates with artificial diet were treated with aqueous test solutions prepared from 10'000 ppm DMSO stock solutions by pipetting. After drying, the plates were infested with L2 larvae (6 to 10 per well). The samples were assessed for mortality and growth inhibition 5 days after infestation. Control of Diabrotica balteata by a test sample is noted when at least one of mortality and growth inhibition is better than the untreated sample.

The following compounds resulted in at least 80% control at an application rate of 200 ppm: A1, A2, A3, A4, B1, B2, B3, B4, B5, B6

Diabrotica balteata, (Corn Rootworm)

Maize sprouts, placed on an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality 4 days after infestation.

The following compounds resulted in at least 80% mortality at an application rate of 200 ppm: C1 to C56, D2

Myzus persicae (Green Peach Aphid):

Sunflower leaf discs were placed on agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: A3, B1, B4, C1, C12, C15, C16, C18, C19, C22, C23, C25, C26, C27, C28, C30, C32, C36, C37, C39, C40, C41, C50, C52, C53, C55

Thrips tabaci (Onion Thrips):

Sunflower leaf discs were placed on agar in 24-well microtiter plates and sprayed with aqueous test solutions prepared from 10'000 ppm DMSO stock solutions. After drying the leaf discs were infested with a thrips population of mixed ages. The samples were assessed for mortality 6 days after infestation.

The following compounds resulted in at least 80% control at an application rate of 200 ppm: A1, A2, A3, B1, B2, B3, B4, B5, B6, C1 to C9, C11, C12, C14, C15, C16, C18 to C23, C25 to C34, C36 to C56

Tetranychus urticae (Two-Spotted Spider Mite):

Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality (mobile stages) 8 days after infestation.

The following compounds resulted in at least 80% control at an application rate of 200 ppm: 15 A1, A2, A3, A4, B1, B2, B3, B4, B5, B6, C1, C3, C4, C5, C8, C11, C12, C14, C16, C18 to C23, C25 to C28, C30 to C32, C36 to C38, C40, C41, C43, C47, C48, C50, C52 to C55, D1

Test to Determine Biological Safety Profile

Spodoptera littoralis (Egyptian Cotton Leafworm)

Cotton plants in the 5 leaf stage (around 5 weeks old) are treated in an automated turn table spray chamber. Plants were stored in the greenhouse at 26° C. and 14h day length during the whole test period. 2, and 16 days after treatment, 4 leaves from each sample were excised, placed into 14cm plastic petri dishes on wet filter paper. The infestation of 10 L-3 Spodoptera littoralis is made immediately afterwards. The samples were assessed for mortality, growth inhibition and anti-feedant effect after an incubation period of 6 days at 27° C. (without light). Control of Spodoptera littoralis by a test sample is noted when at least one of mortality, growth inhibition and anti-feedant effect is higher than the untreated sample.

Tetranychus urticae (Two Spotted Spider Mite)

Bean plants are infested with mite populations of mixed ages. 1 day after infestation, plants are treated in a spray chamber with diluted test solutions. 1 and 10 days later, samples are checked for mortality.

The invention claimed is:
1. A compound of formula I

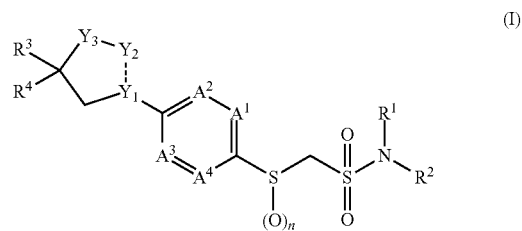

wherein
$A^1$ is C—$R^{5b}$;
$A^2$, $A^3$ and $A^4$ are independently of one another C—H, C—$R^{5a}$ or nitrogen;
$Y_1$—$Y_2$—$Y_3$ is —C=N—O—, —C=N—S—, —C=N—CH$_2$—, —C=CH—O— or —N—CH$_2$—CH$_2$—, —C=CH—S—;
n is 0, 1 or 2;
$R^1$ is hydrogen, $C_1$-$C_8$alkyl, $C_1$-$C_8$alkoxy or $C_1$-$C_8$alkylcarbonyl or $C_1$-$C_8$alkoxycarbonyl;
$R^2$ is hydrogen, $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, aryl-$C_1$-$C_4$alkylene or aryl-$C_1$-$C_4$alkylene wherein the aryl moiety is substituted by one to five $R^8$, heterocyclyl-$C_1$-$C_4$alkylene or heterocyclyl-$C_1$-$C_4$alkylene wherein the heterocyclyl moiety is substituted by one to five $R^8$, aryl or aryl substituted by one to five $R^8$, heterocyclyl or heterocyclyl substituted by one to five $R^8$;
or $R^1$ and $R^2$ together with the nitrogen atom to which they are bound form a 4- to 7-membered cycle containing carbon atoms as ring members and optionally containing one oxygen atom or one sulfur atom optionally oxidized as a ring member and wherein the cycle is optionally substituted by 1 to 5 groups independently selected from halogen, $C_1$-$C_4$alkyl and $C_1$-$C_4$alkoxy;
$R^3$ is $C_1$-$C_8$haloalkyl;
$R^4$ is aryl or aryl substituted by one to five $R^9$, or heteroaryl or heteroaryl substituted by one to five $R^9$;
each $R^{5a}$ is independently halogen, cyano, nitro, $C_1$-$C_8$alkyl, $C_1C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-;
$R^{5b}$ is halogen, $C_1$-$C_8$alkyl, $C_1$-$C_8$haloalkyl, $C_2$-$C_8$haloalkenyl, $C_2$-$C_8$alkynyl, $C_2$-$C_8$haloalkynyl, $C_3$-$C_{10}$cycloalkyl or $C_3$-$C_{10}$cycloalkyl substituted by one to five $R^7$, or $R^{5a}$ and $R^{5b}$ on adjacent carbon atoms together form a —CH=CH—CH=CH— bridge or a —N=CH—CH=CH— bridge;

each $R^6$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;

each $R^7$ is independently halogen, cyano, $C_1$-$C_8$alkyl or $C_1$-$C_8$haloalkyl;

each $R^8$ and $R^9$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{10}$ or heterocyclyl or heterocyclyl substituted by one to five $R^{10}$;

each $R^{10}$ is independently halogen, cyano, nitro, $C_1$-$C_4$alkyl, $C_1$-$C_4$haloalkyl, $C_1$-$C_4$alkoxy or $C_1$-$C_4$haloalkoxy;

or a salt or N-oxide thereof.

2. A compound according to claim 1, wherein $Y_1$—$Y_2$—$Y_3$ is —C=N—O—.

3. A compound according to claim 1, wherein $Y_1$—$Y_2$—$Y_3$ is —C=N—$CH_2$—.

4. A compound according to claim 1, wherein $Y_1$—$Y_2$—$Y_3$ is —C=CH—O—.

5. A compound according to claim 1, wherein $Y_1$—$Y_2$—$Y_3$ is —N—$CH_2$—$CH_2$—.

6. A compound according to claim 1, wherein $Y_1$—$Y_2$—$Y_3$ is —C=N—S—.

7. A compound according to claim 1, wherein $Y_1$—$Y_2$—$Y_3$ is —C=CH—S—.

8. A compound according to claim 1, wherein $R^{5b}$ is halogen or methyl.

9. A compound according to claim 1, wherein $R^2$ is $C_1$-$C_4$alkyl or $C_1$-$C_4$alkyl substituted by one to five groups independently selected from halogen, cyano, $C_1$-$C_4$alkoxy and $C_1$-$C_4$alkylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_6$cycloalkyl or $C_3$-$C_6$cycloalkyl substituted by one to five groups independently selected from halogen, methyl and halomethyl, phenyl-$C_1$-$C_2$alkylene or phenyl-$C_1$-$C_2$alkylene wherein the phenyl moiety is optionally substituted by one to three substituents independently selected from halogen, cyano, $C_1$-$C_4$alkyl, $C_1$-$C_4$haloalkyl, $C_1$-$C_4$alkoxy and $C_1$-$C_4$haloalkoxy, pyridyl-$C_1$-$C_2$alkylene or pyridyl-$C_1$-$C_2$alkylene wherein the pyridyl moiety is optionally substituted by one to three substituents independently selected from halogen, cyano, $C_1$-$C_4$alkyl, $C_1$-$C_4$haloalkyl, $C_1$-$C_4$alkoxy and $C_1$-$C_4$haloalkoxy, thietanyl, oxo-thietanyl, dioxo-thietanyl, oxetanyl, tetrahydrofuranyl, thietanyl-methyl, oxo-thietanyl-methyl, dioxo-thietanyl-methyl, and oxetanyl-methyl.

10. A compound according to claim 1, wherein $R^2$ is $C_1$-$C_4$alkyl or $C_1$-$C_4$alkyl substituted by one to five groups independently selected from halogen, cyano, methoxy and methylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_4$cycloalkyl or $C_3$-$C_4$cycloalkyl substituted by one to five groups independently selected from halogen, methyl and halomethyl, pyridylmethyl or pyridylmethyl wherein the pyridyl moiety is substituted with one to four groups selected from halogen, cyano, methyl, halomethyl, methoxy and halomethoxy.

11. A compound according to claim 1, wherein $R^1$ and $R^2$ together with the nitrogen atom to which they are bound form a 4- to 7-membered cycle containing carbon atoms as ring members and optionally containing one oxygen atom or one sulfur atom optionally oxidized as a ring member and wherein the cycle is optionally substituted by 1 to 5 groups independently selected from halogen, $C_1$-$C_4$alkyl and $C_1$-$C_4$alkoxy.

12. A compound according to claim 1, wherein $R^3$ is chlorodifluoromethyl or trifluoromethyl.

13. A compound according to claim 1, wherein $R^4$ is group A1

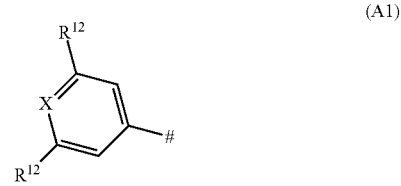

(A1)

wherein X is C—$R^{12}$ or nitrogen and each $R^{12}$ is independently hydrogen, halogen or trihalomethyl, wherein at least two $R^{12}$ are not hydrogen.

14. A compound according to claim 1, wherein $A^1$ is C—$R^{5b}$; $A^2$, $A^3$ and $A^4$ are C—H; $Y_1$—$Y_2$—$Y_3$ is —C=N—O—, —C=N—S—, —C=N—$CH_2$—, —C=CH—O—, —N—$CH_2$—$CH_2$— or C=CH—S—; $R^1$ is hydrogen; $R^2$ is $C_1$-$C_4$alkyl or $C_1$-$C_4$alkyl substituted by one to five groups independently selected from halogen, cyano, methoxy and methylthio, $C_2$-$C_4$alkenyl or $C_2$-$C_4$alkenyl substituted by one to five halogen, $C_2$-$C_4$alkynyl or $C_2$-$C_4$alkynyl substituted by one to five halogen, $C_3$-$C_4$cycloalkyl or $C_3$-$C_4$cycloalkyl substituted by one to five groups independently selected from halogen, methyl and halomethyl, pyridylmethyl or pyridylmethyl wherein the pyridyl moiety is substituted with one to four groups selected from halogen, cyano, methyl, halomethyl, methoxy and halomethoxy; or $R^1$ and $R^2$ together with the nitrogen atom to which they are bound form a 4- to 7-membered cycle containing carbon atoms as ring members and optionally containing one oxygen atom as a ring member; $R^3$ is trifluoromethyl; $R^4$ is group A1

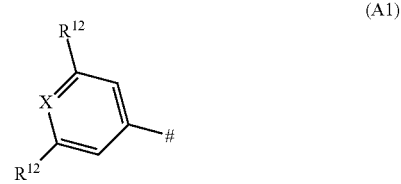

(A1)

wherein X is C—$R^{12}$ and each $R^{12}$ is independently hydrogen, halogen or trihalomethyl, wherein at least two $R^{12}$ are not hydrogen; $R^{5b}$ is halogen or methyl.

15. A compound according to claim 14, wherein $A^1$ is C—$R^{5b}$; $A^2$, $A^3$ and $A^4$ are C—H; $Y_1$—$Y_2$—$Y_3$ is —C=N—O—, —C=N—S—, —C=N—$CH_2$—, —C=CH—O— or —N—$CH_2$—$CH_2$— or C=CH—S—; $R^1$ is hydrogen; $R^2$ is methyl, ethyl, propyl, butyl, fluoroethyl, fluoropropyl, fluorobutyl, difluoroethyl, difluoropropyl, difluorobutyl, trifluoroethyl, trifluoropropyl, trifluorobutyl, cyclopropyl, cyclobutyl, allyl, propargyl, pyridylmethyl; $R^3$ is trifluoromethyl; $R^4$ is group A1, wherein X is C—$R^{12}$ and each $R^{12}$ is independently hydrogen, halogen or trihalomethyl, wherein at least two $R^{12}$ are not hydrogen; $R^{5b}$ is chloro, bromo or methyl.

16. A mixture comprising a compound of formula I* and a compound of formula I**

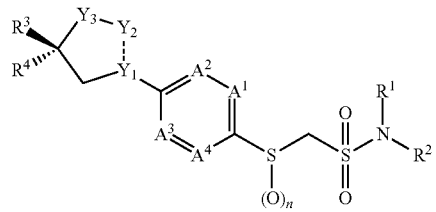

I*

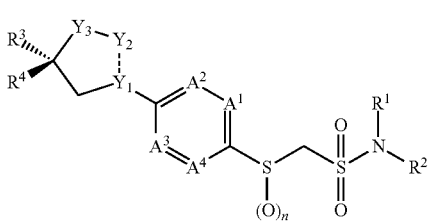

I** wherein $Y_1$—$Y_2$—$Y_3$ is —C=N—O—, —C=N—S—, —C=N—CH$_2$—, —C=CH—O—, —N—CH$_2$—CH$_2$— or —N—CH$_2$—CH$_2$—; and $A^1$, $A^2$, $A^3$, $A^4$, $R^1$, $R^2$, $R^3$, $R^4$ and n are as defined in claim 1, and wherein the molar proportion of the compound of formula I** compared to the total amount of both the compound of formula I* and I** is greater than 50%.

17. A mixture according to claim 16, wherein $A^1$, $A^2$, $A^3$, $A^4$, $Y^1$, $Y^2$, $Y^3$, $R^1$, $R^2 R^3$, $R^4$ and n are as defined in claim 13, and wherein the molar proportion of the compound of formula I** compared to the total amount of both the compound of formula I* and I** is greater than 70%.

18. A mixture according to claim 16, wherein $A^1$, $A^2$, $A^3$, $A^4$, $Y^1$, $Y^2$, $Y^3$, $R^1$, $R^2$, $R^3$, $R^4$ and n are as defined in claim 14, and wherein the molar proportion of the compound of formula I** compared to the total amount of both the compound of formula I* and I** is greater than 70%.

19. A compound of formula Int-I

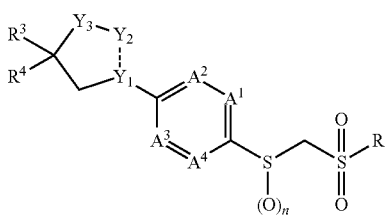

(Int-I)

wherein $Y_1$—$Y_2$—$Y_3$ is —C=N—O—, —C=N—S—, —C=N—CH$_2$—, —C=CH—O—, or —N—CH$_2$—CH$_2$— or —N—CH$_2$—CH$_2$—; and $A^1$, $A^2$, $A^3$, $A^4$, $R^3$, $R^4$ and n are as defined for the compound of formula I in claim 1, and R is OH or halogen, or a salt of N-oxide thereof; or a compound of formula Int-II

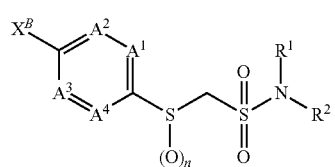

(Int-II)

wherein $A^1$, $A^2$, $A^3$, $A^4$, $R^1$, $R^2$ and n are as defined for the compound of formula I in claim 1 provided that not both of $R^1$ and $R^2$ are H, and $X^B$ is a leaving group or $X^B$ is cyano, formyl or acetyl, or a salt of N-oxide thereof; or a compound of formula Int-III

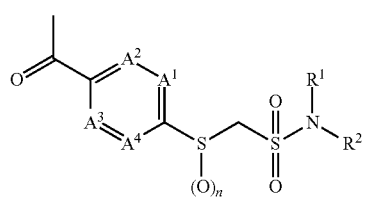

(Int-III)

wherein $A^1$, $A^2$, $A^3$, $A^4$, $R^1$, $R^2$ and n are as defined for the compound of formula I in claim 1, or a salt of N-oxide thereof; or a compound of formula Int-IV

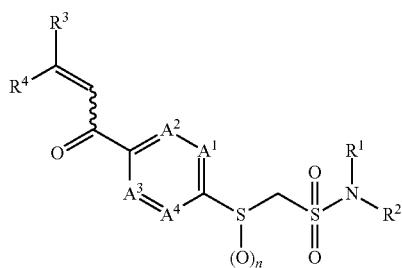

(Int-IV)

wherein $A^1$, $A^2$, $A^3$, $A^4$, $R^1$, $R^2$, $R^3$, $R^4$ and n are as defined for the compound of formula I in claim 1, or a salt of N-oxide thereof.

20. An insecticidal, acaricidal, nematicidal or molluscicidal composition comprising an insecticidally, acaricidally, nematicidally or molluscicidally effective amount of a compound of formula (I) as defined in claim 1 and optionally at least one additional compound having biological activity.

21. A combination product comprising a pesticidally effective amount of a component A and a pesticidally effective amount of component B, wherein component A is a compound of formula (I) as defined in claim 1, and component B is at least one compound selected from the group consisting of imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene, S-methoprene, clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone and tebufenozide.

* * * * *